United States Patent
Ma et al.

(10) Patent No.: US 11,590,234 B2
(45) Date of Patent: Feb. 28, 2023

(54) HYPERBRANCHED POLYMERS AND POLYPLEXES AND DNA OR RNA DELIVERY SYSTEMS INCLUDING THE SAME

(71) Applicant: THE REGENTS OF THE UNIVERSITY OF MICHIGAN, Ann Arbor, MI (US)

(72) Inventors: Peter X. Ma, Ann Arbor, MI (US); Xiaojin Zhang, Wuhan (CN)

(73) Assignee: The Regents of the University of Michigan, Ann Arbor, MI (US)

( * ) Notice: Subject to any disclaimer, the term of this patent is extended or adjusted under 35 U.S.C. 154(b) by 195 days.

(21) Appl. No.: 15/720,542

(22) Filed: Sep. 29, 2017

(65) Prior Publication Data

US 2018/0021441 A1 Jan. 25, 2018

Related U.S. Application Data

(63) Continuation of application No. PCT/US2016/025670, filed on Apr. 1, 2016.

(60) Provisional application No. 62/142,433, filed on Apr. 2, 2015.

(51) Int. Cl.
| | |
|---|---|
| *A61K 47/00* | (2006.01) |
| *A61K 47/50* | (2017.01) |
| *A61K 47/59* | (2017.01) |
| *C08G 83/00* | (2006.01) |
| *C08G 73/02* | (2006.01) |
| *C08F 210/02* | (2006.01) |
| *C08G 63/66* | (2006.01) |
| *A61K 47/69* | (2017.01) |
| *A61K 47/60* | (2017.01) |
| *A61L 27/18* | (2006.01) |
| *A61L 27/26* | (2006.01) |
| *A61L 27/44* | (2006.01) |
| *A61L 27/52* | (2006.01) |
| *A61L 27/54* | (2006.01) |
| *A61L 27/56* | (2006.01) |
| *A61L 27/58* | (2006.01) |
| *C08G 81/00* | (2006.01) |
| *C12N 15/113* | (2010.01) |

(52) U.S. Cl.
CPC ............ *A61K 47/593* (2017.08); *A61K 47/50* (2017.08); *A61K 47/60* (2017.08); *A61K 47/6937* (2017.08); *A61L 27/18* (2013.01); *A61L 27/26* (2013.01); *A61L 27/44* (2013.01); *A61L 27/52* (2013.01); *A61L 27/54* (2013.01); *A61L 27/56* (2013.01); *A61L 27/58* (2013.01); *C08F 210/02* (2013.01); *C08G 63/66* (2013.01); *C08G 73/024* (2013.01); *C08G 73/0206* (2013.01); *C08G 81/00* (2013.01); *C08G 83/00* (2013.01); *C08G 83/005* (2013.01); *C12N 15/113* (2013.01); *A61L 2300/258* (2013.01); *A61L 2300/604* (2013.01); *A61L 2430/02* (2013.01); *C08G 2210/00* (2013.01); *C08G 2230/00* (2013.01); *C12N 2310/14* (2013.01); *C12N 2310/141* (2013.01); *C12N 2310/351* (2013.01); *C12N 2310/51* (2013.01); *C12N 2310/52* (2013.01)

(58) Field of Classification Search
None
See application file for complete search history.

(56) References Cited

U.S. PATENT DOCUMENTS

| | | |
|---|---|---|
| 2008/0312174 A1 | 12/2008 | Yu et al. |
| 2011/0305685 A1 | 12/2011 | Tseng et al. |

FOREIGN PATENT DOCUMENTS

| | | |
|---|---|---|
| WO | WO 2005/075527 | 8/2005 |

OTHER PUBLICATIONS

Tu et al., Polymer, 2013, 54: 2020-2027.*
Cao et al., Biomaterials, 2011, 32: 2222-2232.*
Han et al., Biomaterials, 2013, 34: 4680-4689.*
Cao, Supplementary Information, 2011.*
Shuai, Macromolecules, 2003, 36: 5751-5759.*
Liu, Macromol. Rapid Commun., 2010, 31: 1509-1515.*
Liu et al., J. Control. Rel., 2011, 152: e157-e159.*
Liu, Biotechnology Advances, online Dec. 3, 2013, 32: 693-710.*
Park, Macromol. Rapid. Commun., 2010, 31: 1122-1133.*
Nisha et al., Langmuir, 2004, 20: 2386-2396.*
Prabaharan, Biomaterials, 2009, 30: 5757-5766.*
Deng et al., Biomaterials, online Jan. 17, 2014, 35: 4333-4344.*
Ando et al. (J. Gen. Med., 2013, 15: 20-27).*
Aryal, Int. J. Biol. Macromol., 2009, 44: 346-352.*
International Search Report and Written Opinion for International Application No. PCT/US2016/025670 dated Jul. 25, 2016, 11 pages.
Shuai, X. et al., Novel Biodegradable Ternary Copolymers hy-PEI-g-PCL-b-PEG: Synthesis, Characterization, and Potential as Efficient Nonviral Gene Delivery Vectors, Macromolecules, 2003, vol. 36, No. 15, pp. 5751-5759.
Reul, R. et al., Amine-modified hyperbranched polyesters as non-toxic, biodegradable gene delivery systems, Biomaterials, 2009, vol. 30, No. 29, pp. 5815-5824.
Zhang, X. et al., Miktoarm copolymers bearing one poly (ethylene glycol) chain and several poly (ε-caprolactone) chains on a hyperbranched polyglycerol core, Macromolecules, 2010, vol. 43, No. 16, pp. 6671-6677.

(Continued)

*Primary Examiner* — Ileana Popa
(74) *Attorney, Agent, or Firm* — Dierker & Kavanaugh, P.C.

(57) ABSTRACT

A hyperbranched polymer includes a hyperbranched, hydrophobic molecular core, respective low molecular weight polyethyleneimine chains attached to at least three branches of the hyperbranched, hydrophobic molecular core, and respective polyethylene glycol chains attached to at least two other branches of the hyperbranched, hydrophobic molecular core. Examples of the hyperbranched polymer may be used to form hyperbranched polyplexes, and may be included in DNA or RNA delivery systems.

11 Claims, 28 Drawing Sheets

(56) References Cited

OTHER PUBLICATIONS

Zhang, X. et al., Cell-free 3D scaffold with two-stage delivery of miRNA-26a to regenerate critical-sized bone defects, Nature Communications, 2016, vol. 7, DOI: 10.1038/ncomms10376 (published Jan. 14, 2016).
Liu, Yu et al., "A new synthesis method and degradation of hyper-branched polyethylenimine grafted polycaprolactone block mono-methoxyl poly (ethylene glycol) copolymers (hy-PEI-g-PCL-b-mPEG) as potential DNA delivery vectors", Polymer 50 (2009), pp. 3895-3904.
Shuai, Xintao et al., "Novel Biodegradable Ternary Copolymers hy-PEI-g-PCL-b-PEG: Synthesis, Characterization, and Potential as Efficient Nonviral Gene Delivery Vectors", Macromolecules 2003, 36, pp. 5751-5759.
Petersen, Holger et al., "Star-Shaped Poly(ethylene glycol)-block-polyethylenimine Copolymers Enhance DNA Condensation of Low Molecular Weight Polyethylenimines", Biomacromolecules 2002, 3, pp. 926-936.

* cited by examiner

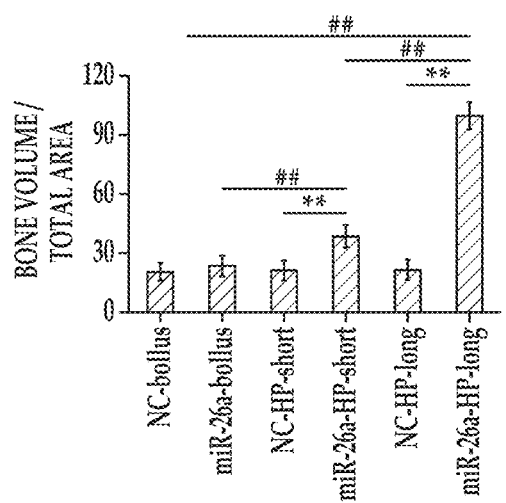
FIG. 20D
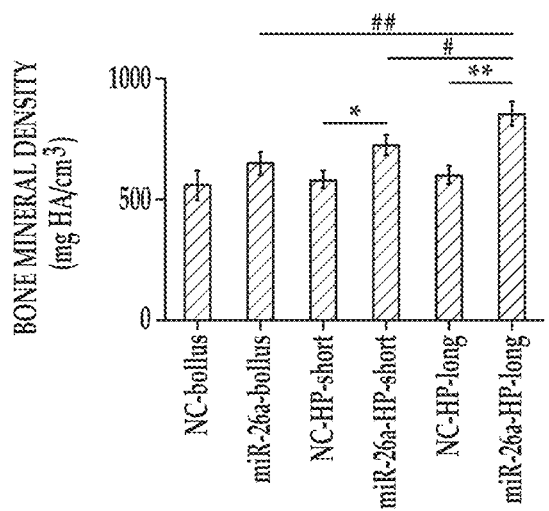
FIG. 20E
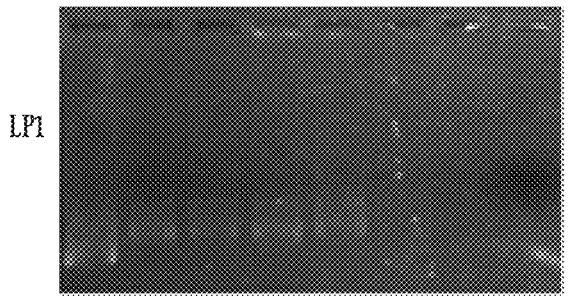
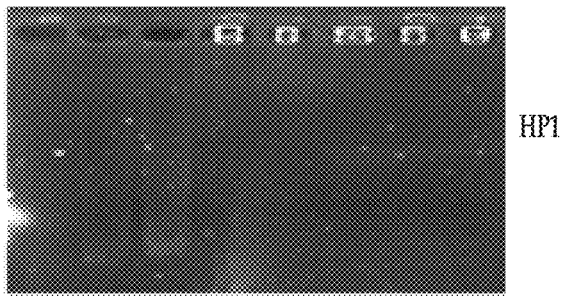
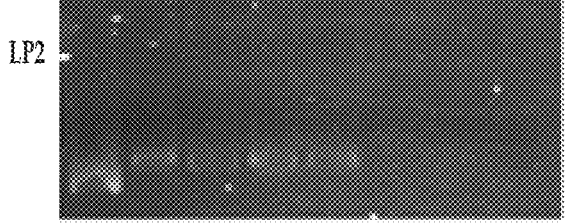
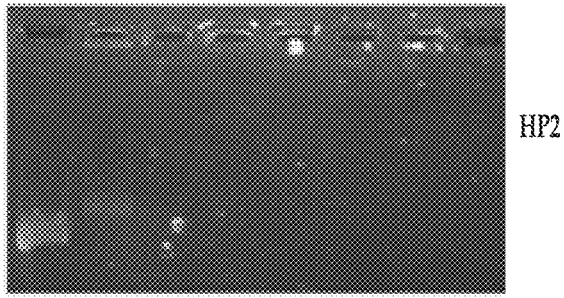
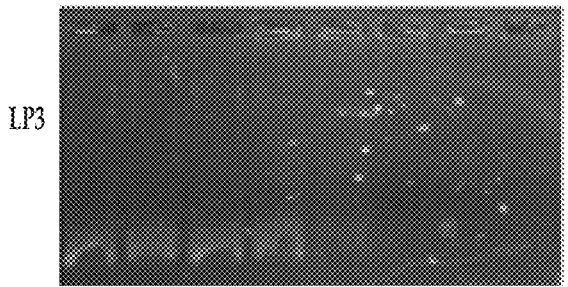
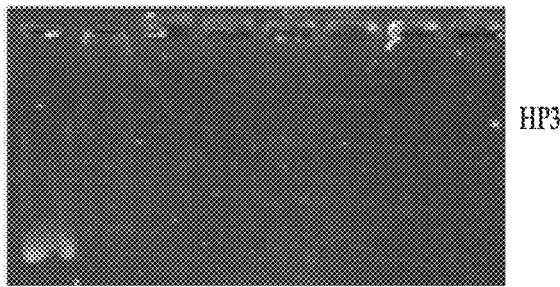
FIG. 21

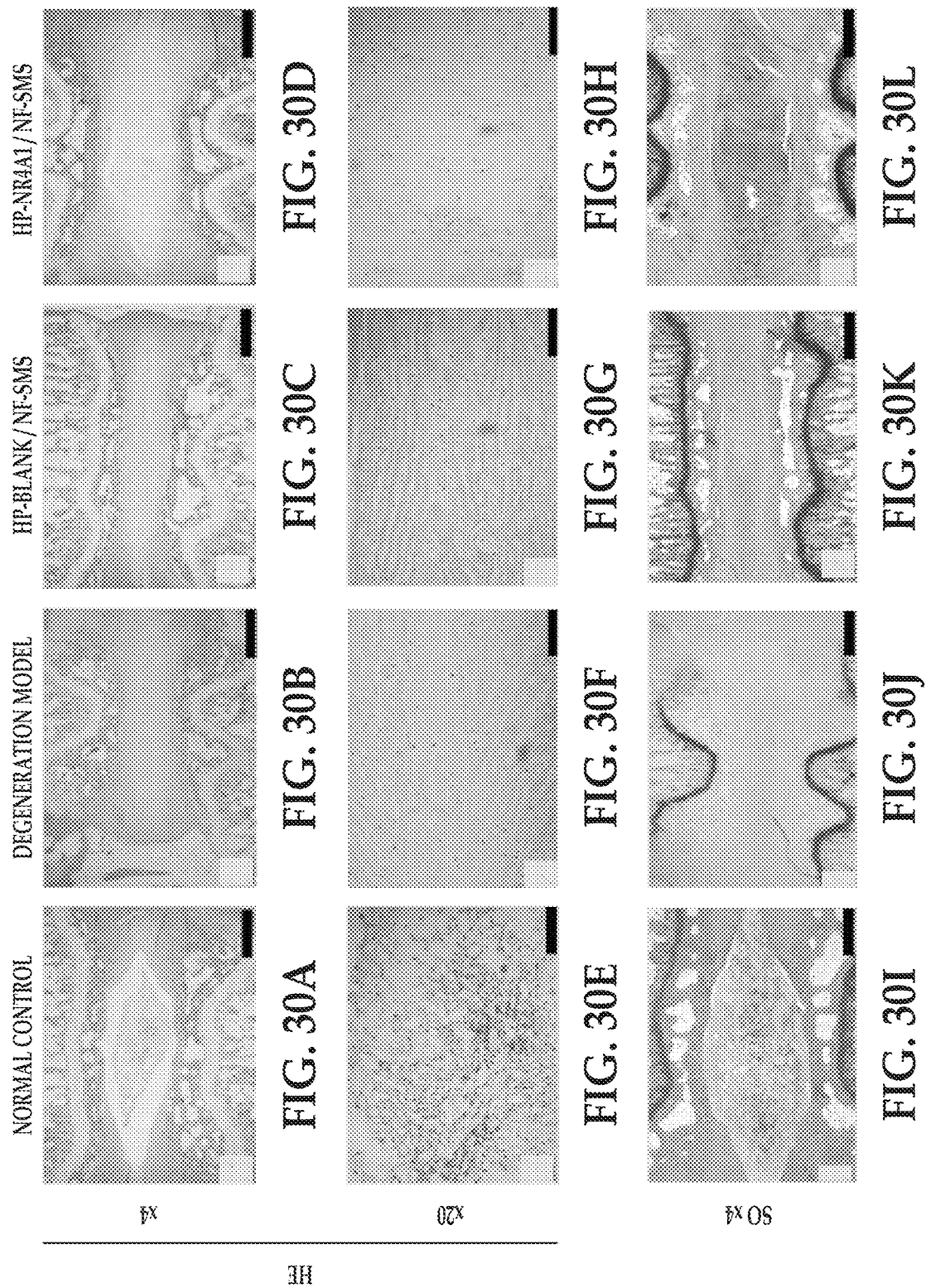

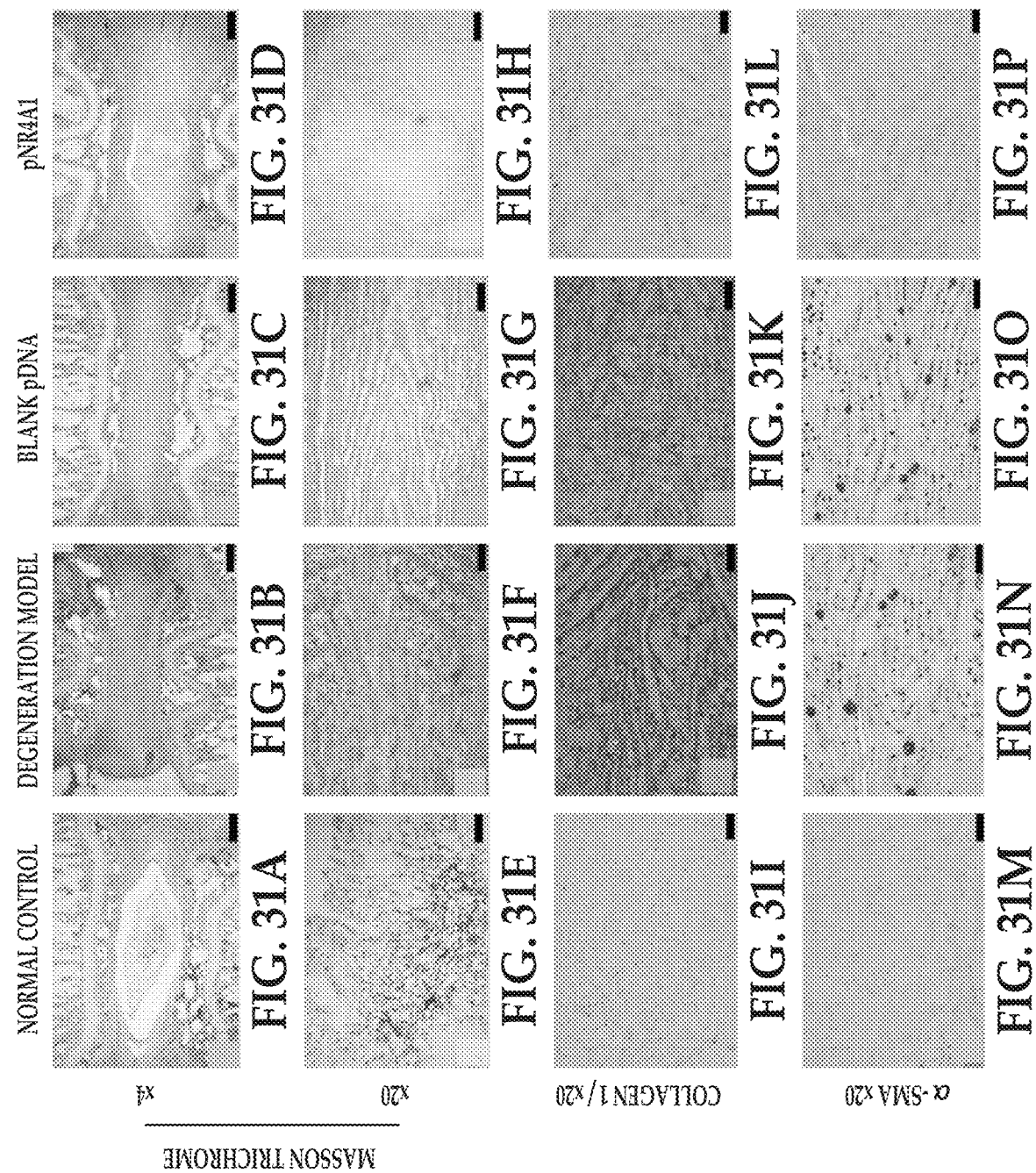

TGF-β(-)      TGF-β(+)      TGF-β(+)/ANTI-miR-199a

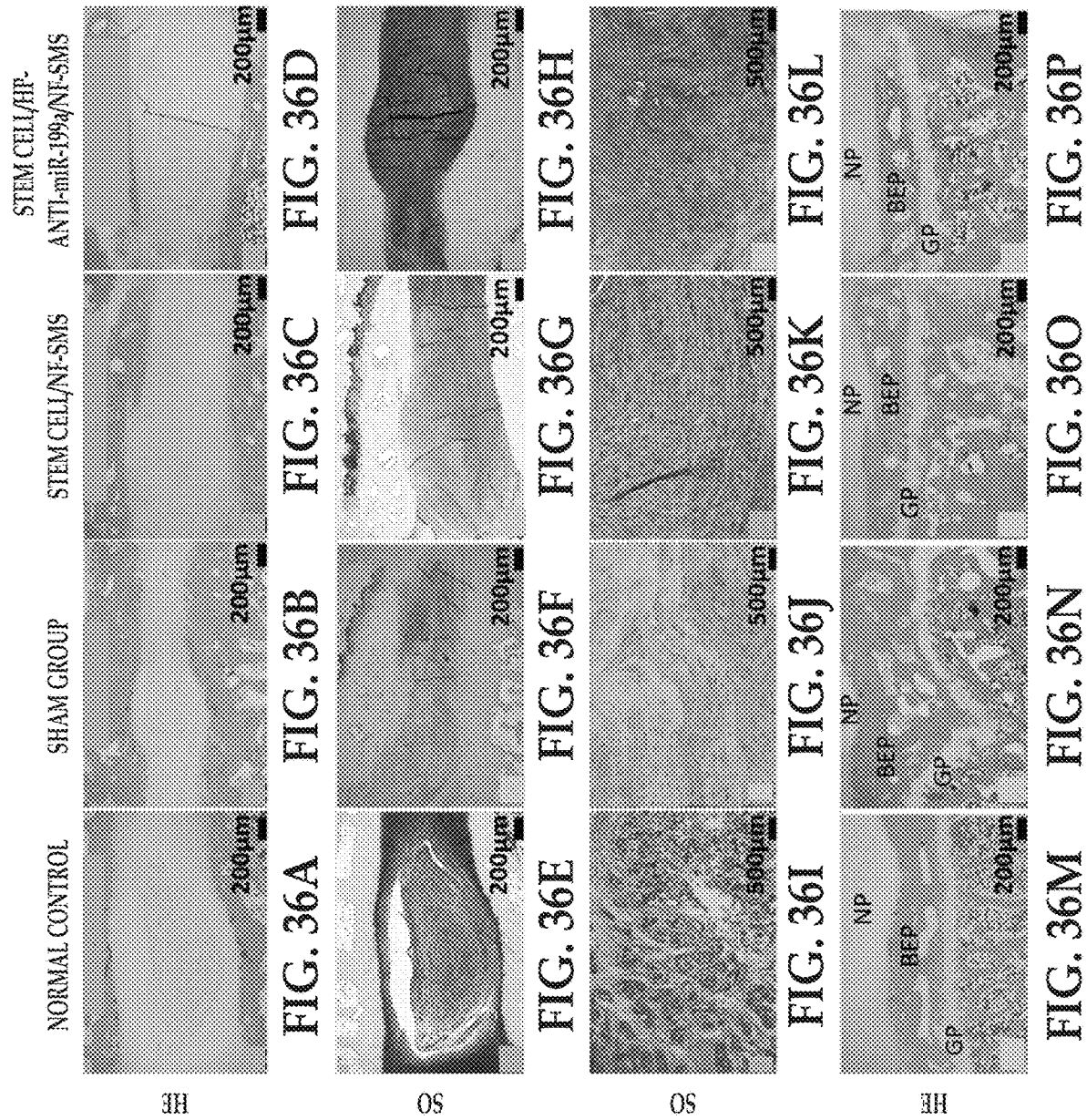

HYPERBRANCHED POLYMERS AND POLYPLEXES AND DNA OR RNA DELIVERY SYSTEMS INCLUDING THE SAME

CROSS-REFERENCE TO RELATED APPLICATIONS

This application is a continuation of co-pending international application S.N. PCT/US2016/025670, filed Apr. 1, 2016, which itself claims the benefit of U.S. Provisional Application Ser. No. 62/142,433, filed Apr. 2, 2015, each of which is incorporated by reference herein in its entirety.

STATEMENT REGARDING FEDERALLY SPONSORED RESEARCH OR DEVELOPMENT

This invention was made with government support under Grant Nos. DE015384, DE017689 and DE022327 awarded by the National Institutes of Health (NIH) and the National Institute of Dental and Craniofacial Research (NIDCR), and under Grant No. DMR-1206575 awarded by the National Science Foundation (NSF). The government has certain rights in the invention.

BACKGROUND

Some DNA and RNA (e.g., microRNA or miRNA, messenger RNA or mRNA, and small interfering RNA or siRNA) have been found to have surprising roles in some human diseases, such as cancer, diabetes, heart disease, and fibrotic disc degeneration (in which the TGF-β signaling pathway plays a central role). However, delivery of DNA or RNA in vivo may be challenging due to properties of the DNA or RNA, or of the carrier system for the DNA or RNA.

For example, miRNAs and their mimics or inhibitors (all negatively charged) cannot easily cross the cell membrane (which is also negatively charged) to enter cells and accomplish targeted gene regulations due to the coulomb repulsion of like charges. miRNAs also rapidly degrade in vivo. While viral vectors can efficiently deliver miRNAs into cells, there may be adverse immune response to viral factors. Some non-viral vectors form liposome vesicles, composed of a lipid bilayer to encapsulate the RNAs inside (called lipoplexes), that efficiently transport RNAs into cells in vitro. However, the transfection efficiency of lipoplexes is low in vivo. Chemical modifications may improve the stability and transfection efficiency of miRNA mimics or their inhibiting anti-sense oligoribonucleotides (miRNA inhibitors). However, each miRNA or its inhibitor needs to be specifically modified to form the so-called "agomirs" or "antagomirs", resulting in low availabilities and high costs. Polymer vectors have also been explored for carriers of DNA and siRNA. For example, polyethylenimine (PEI) and linear copolymers thereof may be utilized to mediate the delivery of miR-145 and/or miR-33a. However, it has been found that PEI with a high molecular weight (e.g., 25000 g/mol) is toxic to cells even though it is efficacious for transfection, and PEI with a low molecular weight is low in toxicity, but also is low in transfection efficiency. As used herein, "low molecular weight" means 2000 g/mol or less. Some specific examples of low molecular PEI include 1000 g/mol or 800 g/mol.

For another example, the orphan nuclear receptor 4A1 (NR4A1, also known as NUR77) may be administered to treat a variety of diseases, including fibrosis. However, oral administration of NR4A1 may result in the inhibition of TGF-β signaling in normal cells (as well as cells affected by fibrosis), which can lead to nonspecific toxicity (i.e., side effects on unintended cells).

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 20D and 20E are graphs depicting, respectively, the quantitative analysis showing the amount of bone formation and bone mineral density from the groups used in FIGS. 20A-20C, where *P<0.05; **P<0.01; #P<0.05; ##P<0.01 (for FIGS. 20A-20E, all experiments were done in triplicate; n=5 per group; Data are mean±s.d. Scale bars, 5 mm (in microCT images of FIGS. 20A-20C), 2.0 mm (in H&E images at right of FIGS. 20A-20C), and 200 μm (in higher magnifications H&E images at far right of FIGS. 20A-20C);

FIG. 21 is a graph illustrating the agarose gel electrophoresis retardation assay for DNA polyplexes of linear polymers (left) and hyperbranched polymers (right) at various polymer/pDNA N/P ratios;

FIGS. 30A through 30H are hematoxylin and eosin (H&E) stained disc images (at 4× and 20× magnification) of (30A, 30E) the normal control rat caudal spine, (30B, 30F) the rat caudal spine punctured and not treated (degeneration model group), (30C, 30G) the rat caudal spine punctured and treated with NF-SMS attaching blank vectors of a hyperbranched polymer, and (30D, 30H) the rat caudal spine punctured and treated with NF-SMS attaching PLGA nanospheres having embedded therein polymer/NR4A1 polyplexes (scale bar: 30A-30D=250 µm and 30E-30H=100 µm);

FIGS. 30I through 30L are Safranin-O stained disc images (at 4× magnification) of (30I) the normal control rat caudal spine, (30J) the rat caudal spine punctured and not treated (degeneration model group), (30K) the rat caudal spine punctured and treated with NF-SMS attaching blank vectors of a hyperbranched polymer, and (30L) the rat caudal spine punctured and treated with NF-SMS attaching PLGA nanospheres having embedded therein polymer/NR4A1 polyplexes (scale bar: 30I-30L=250 µm);

FIGS. 31A through 31H are Masson Trichrome stained disc images (at 4× and 20× magnification) of (31A, 31E) the normal control rat caudal spine, (31B, 31F) the rat caudal spine punctured and not treated (degeneration model group), (31C, 31G) the rat caudal spine punctured and treated with NF-SMS attaching blank vectors of a hyperbranched polymer, and (31D, 31H) the rat caudal spine punctured and treated with NF-SMS attaching PLGA nanospheres having embedded therein polymer/NR4A1 polyplexes (scale bar: 31A-31D=150 µm and 31E-31H=60 µm);

FIGS. 31I through 31L are immunohistochemical stained (for Collagen I) disc images (at 20× magnification) of (31I) the normal control rat caudal spine, (31J) the rat caudal spine punctured and not treated (degeneration model group), (31K) the rat caudal spine punctured and treated with NF-SMS attaching blank vectors of a hyperbranched polymer, and (31L) the rat caudal spine punctured and treated with NF-SMS attaching PLGA nanospheres having embedded therein polymer/NR4A1 polyplexes (scale bar: 31I-31L=60 µm);

FIGS. 31M through 31P are immunohistochemical stained (for α-SMA) disc images (at 20× magnification) of (31M) the normal control rat caudal spine, (31N) the rat caudal spine punctured and not treated (degeneration model group), (31O) the rat caudal spine punctured and treated with NF-SMS attaching blank vectors of a hyperbranched polymer, and (31P) the rat caudal spine punctured and treated with NF-SMS attaching PLGA nanospheres having embedded therein polymer/NR4A1 polyplexes (scale bar: 31M-31P=60 µm);

FIGS. 36A through 36P are H&E stained images (FIGS. 36A-36D and FIGS. 36M-36P) and Safranin-O stained images (FIGS. 36E-36L) of the normal control rabbit lumbar spine (FIGS. 36A, 36E, 36I, and 36M), the rabbit lumbar spine punctured and not treated (FIGS. 36B, 36F, 36J, and 36N), the rabbit lumbar spine punctured and treated with NF-SMS and blank vectors of a hyperbranched polymer (FIGS. 36C, 36G, 36K, and 36O), and the rabbit lumbar spine punctured and treated with NF-SMS and PLGA nanospheres having embedded therein polymer/anti-miR199a polyplexes (FIGS. 36D, 36H, 36L, and 36P).

DETAILED DESCRIPTION

Disclosed herein are linear and hyperbranched polymers that are capable of acting as polymer vectors for DNA or RNA delivery to cells in vivo and in vitro. Both the linear and hyperbranched polymers are copolymers which combine low molecular weight cationic PEI, linear or hyperbranched polyester, and polyethylene glycol (PEG) chains. Both the linear and hyperbranched polymers are capable of complexing with DNA or RNA, as well as self-assembling into spherical structures (i.e., polyplexes). The spherical structures can be embedded in biodegradable polymers to form biodegradable microspheres or nanospheres, which exhibit controlled release of the DNA or RNA. The embedded microspheres or nanospheres provide a two-stage gene delivery strategy, in which the polyplex releases from the sphere during the first stage and the polyplex enters the cell(s) during the second stage. This two-stage gene delivery strategy enables both controllable duration and high transfection efficiency.

The biodegradable microspheres or nanospheres can also be mixed with or immobilized on a biodegradable or erodible support system or structure (e.g., nanofibrous scaffolds, nanofibrous spongy microspheres, other porous materials, or hydrogels). Localizing the biodegradable microspheres or nanospheres on biodegradable support systems or structures can activate endogenous cells in a spatially and temporally controlled fashion to regenerate bone, tissue, etc. without introducing exogenous cells. This can advantageously prevent unintended delivery of DNA or RNA on off-target cells.

Figure 1:
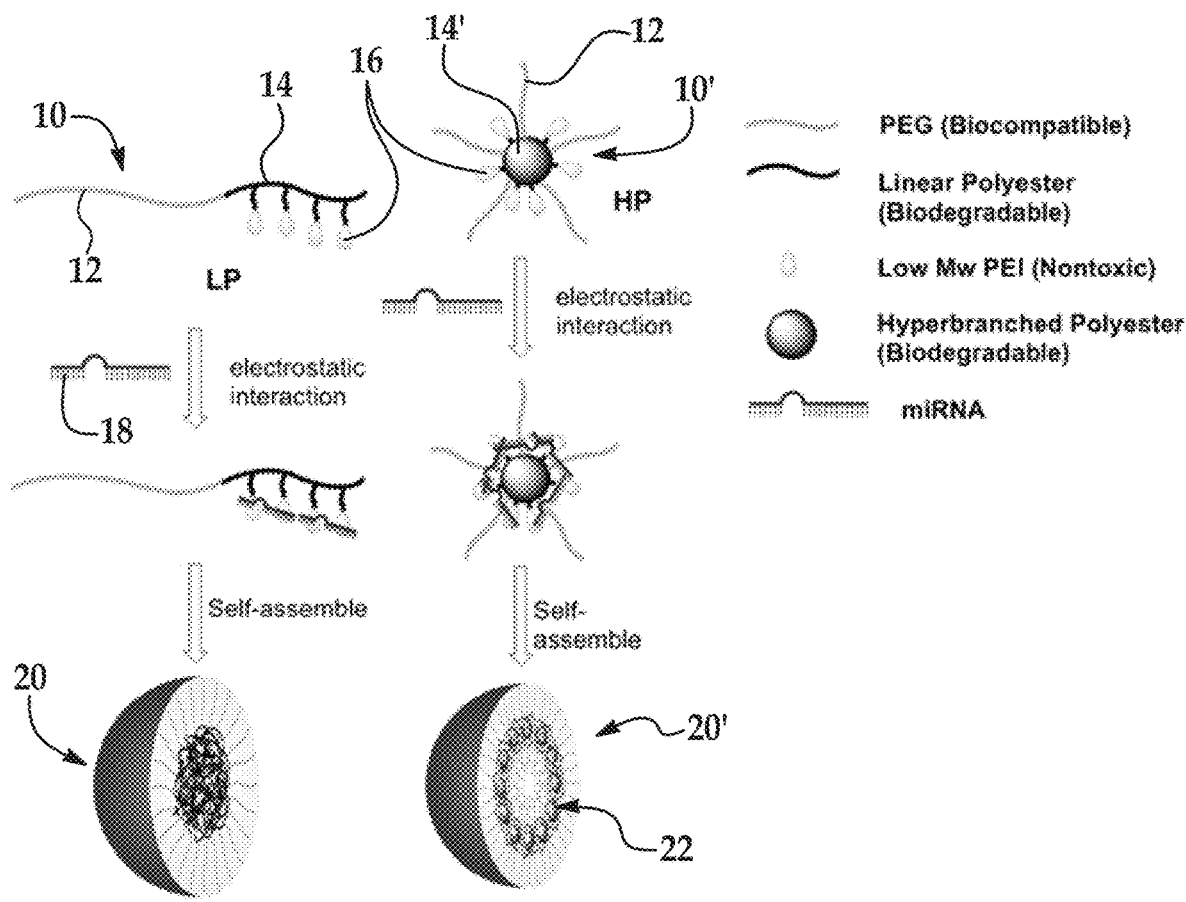
FIG. 1 is a schematic illustration of an example of a linear polymer and a hyperbranched polymer, the interaction of DNA or RNA with the linear polymer and the hyperbranched polymer to form complexes, and the self-assembly of the complexes to form respective polyplexes.

Referring now to FIG. 1, schematic illustrations of the linear polymer 10 and the hyperbranched polymer 10', as well as the polyplexes 20, 20' formed therefrom are depicted. The linear polymer 10 includes a hydrophilic PEG chain 12, a linear, hydrophobic chain 14 attached to the hydrophilic PEG chain 12, and low molecular weight PEI chains 16 attached to the linear, hydrophobic chain 14. The hyperbranched polymer 10' includes a hyperbranched, hydrophobic molecular core 14', respective low molecular weight PEI chains 16 attached to two or more branches of the hyperbranched, hydrophobic molecular core 14', and respective hydrophilic PEG chains 12 attached to two or more other branches of the hyperbranched, hydrophobic molecular core 14'.

The hydrophilic PEG chain 12 may include from 2 to 50,000 repeating ethylene oxide units. In an example, the hydrophilic PEG chain 12 may include from 2 to 1,000 repeating ethylene oxide units.

The linear, hydrophobic chain 14 is a biodegradable polyester. Some examples of biodegradable polyesters include polylactide, polycaprolactone, polycarbonate, poly(phosphoesters), polyanhydrides, and polyglycolic acid.

The hyperbranched, hydrophobic molecular core 14' is a hyperbranched aliphatic polyester including at least 4 terminal hydroxyl groups. Several examples of the hyperbranched, hydrophobic molecular core 14' are shown below:

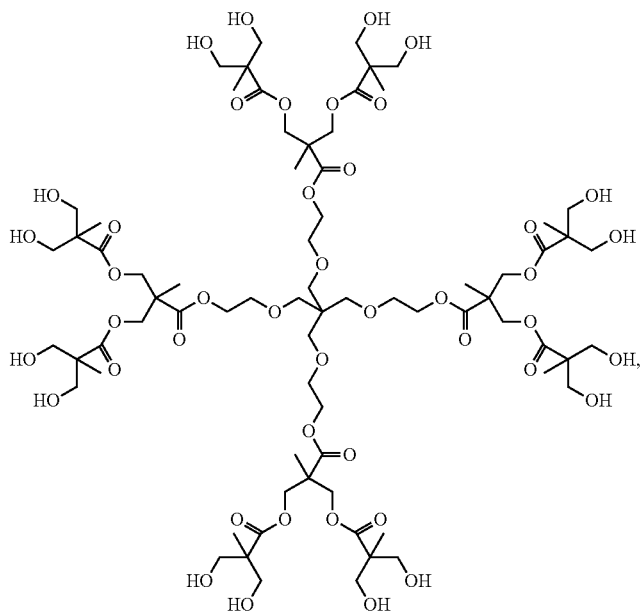

hyperbranched bis-MPA polyester-16-hydroxyl, generation 2

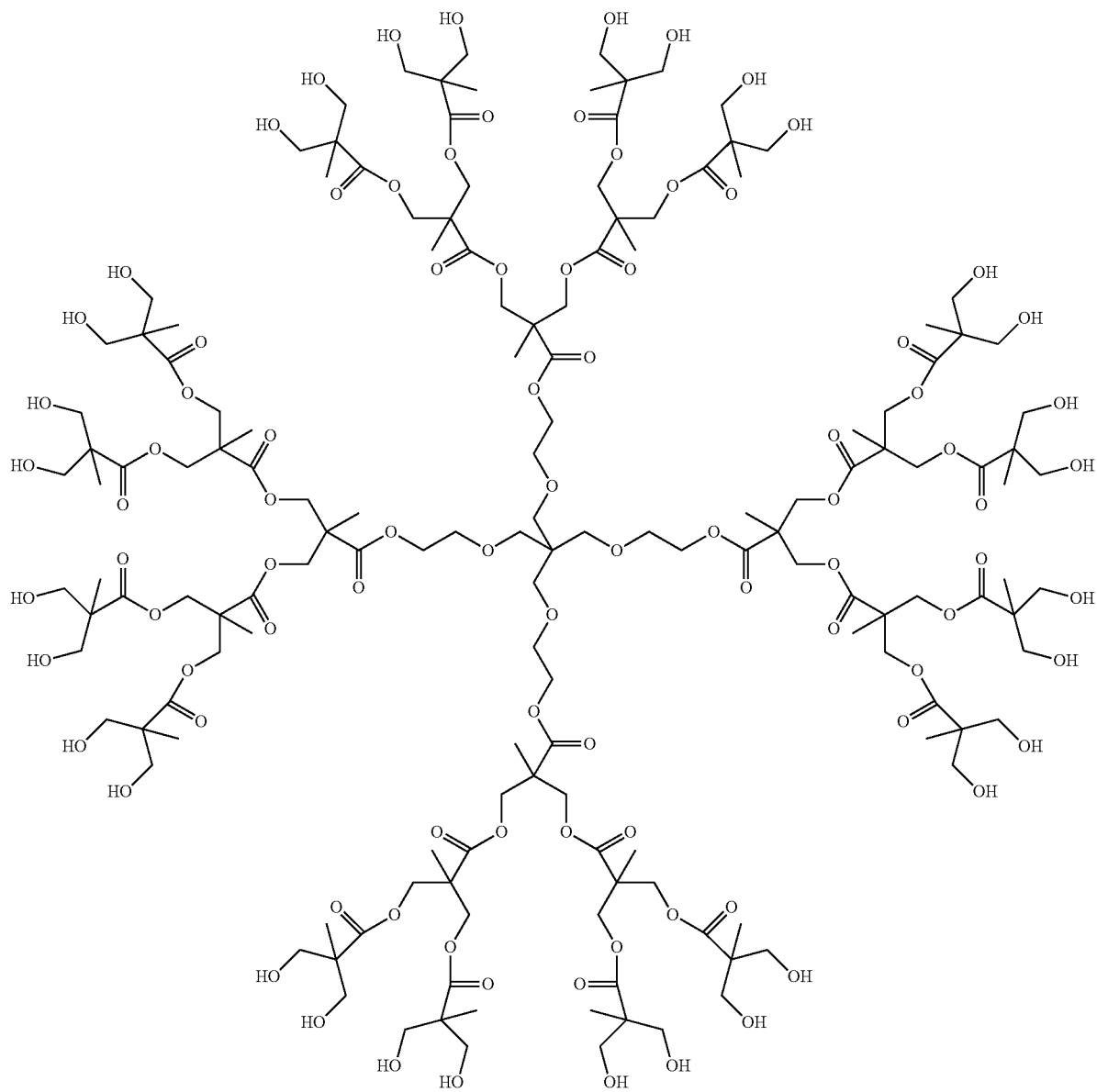
hyperbranched bis-MPA polyester-32-hydroxyl, generation 3, and

-continued

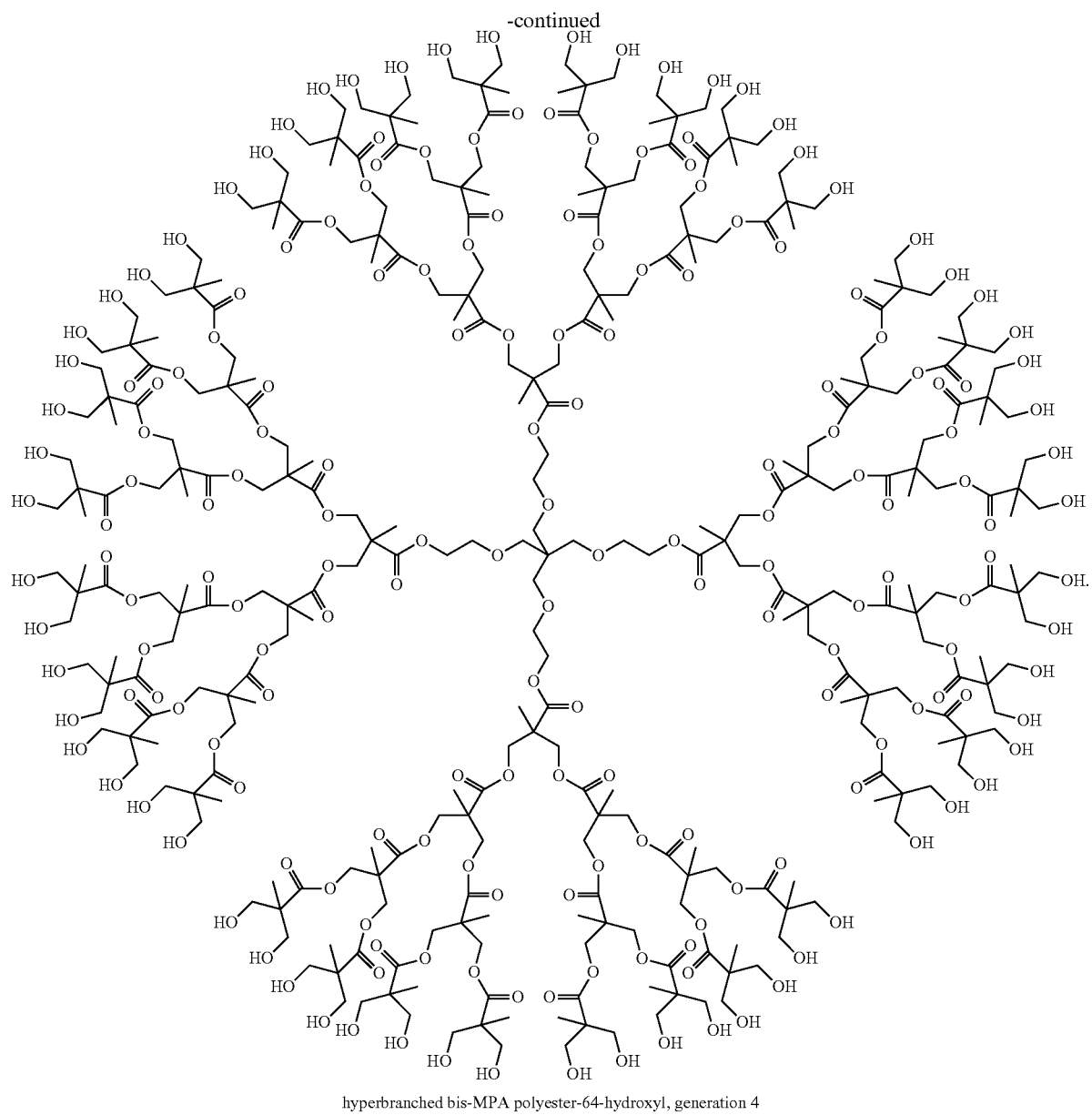

hyperbranched bis-MPA polyester-64-hydroxyl, generation 4

Another example of the hyperbranched, hydrophobic molecular core 14' is hyperbranched bis-MPA polyester-8-hydroxyl, generation 1.

The low molecular weight PEI (polyethyleneimine) chains 16 have a molecular weight ranging from about 400 g/mol to about 5,000 g/mol. In an example, the low molecular weight of the PEI chain 16 is about 800 Da (i.e., 800 g/mol).

Figure 2:
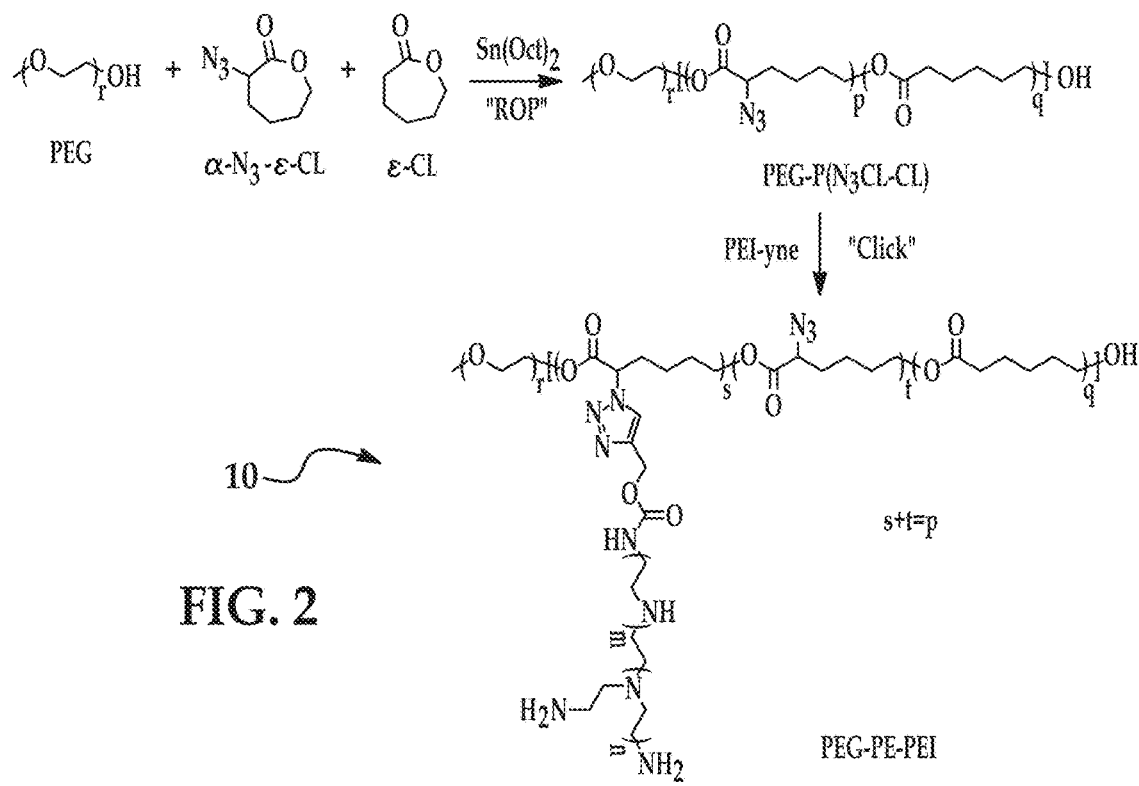
FIG. 2 illustrates one example of the synthesis of an example of the linear polymer (PEG-PE-PEI) disclosed herein.

An example of the method for forming the linear polymer 10 is shown in FIG. 2. In this example, PEG-P(N$_3$CL-CL) (where CL is caprolactone) is synthesized by ring-opening polymerization (ROP) of α-N$_3$-ε-CL and ε-CL with PEG as an initiator and Sn(Oct)$_2$ as a catalyst in bulk. Then, PEG-P(N$_3$CL-CL) is conjugated with PEI-yne (PEI attached to a nitrile end group) via click chemistry (Click) to obtain PEG-PE-PEI (one example of the linear polymer 10). In FIG. 2, r=2 to 50,000, p=2 to 20,000, q=2 to 20,000, s=1 to 20,000, t=1 to 20,000, m=2 to 200, and n=2 to 200.

Figure 3A:
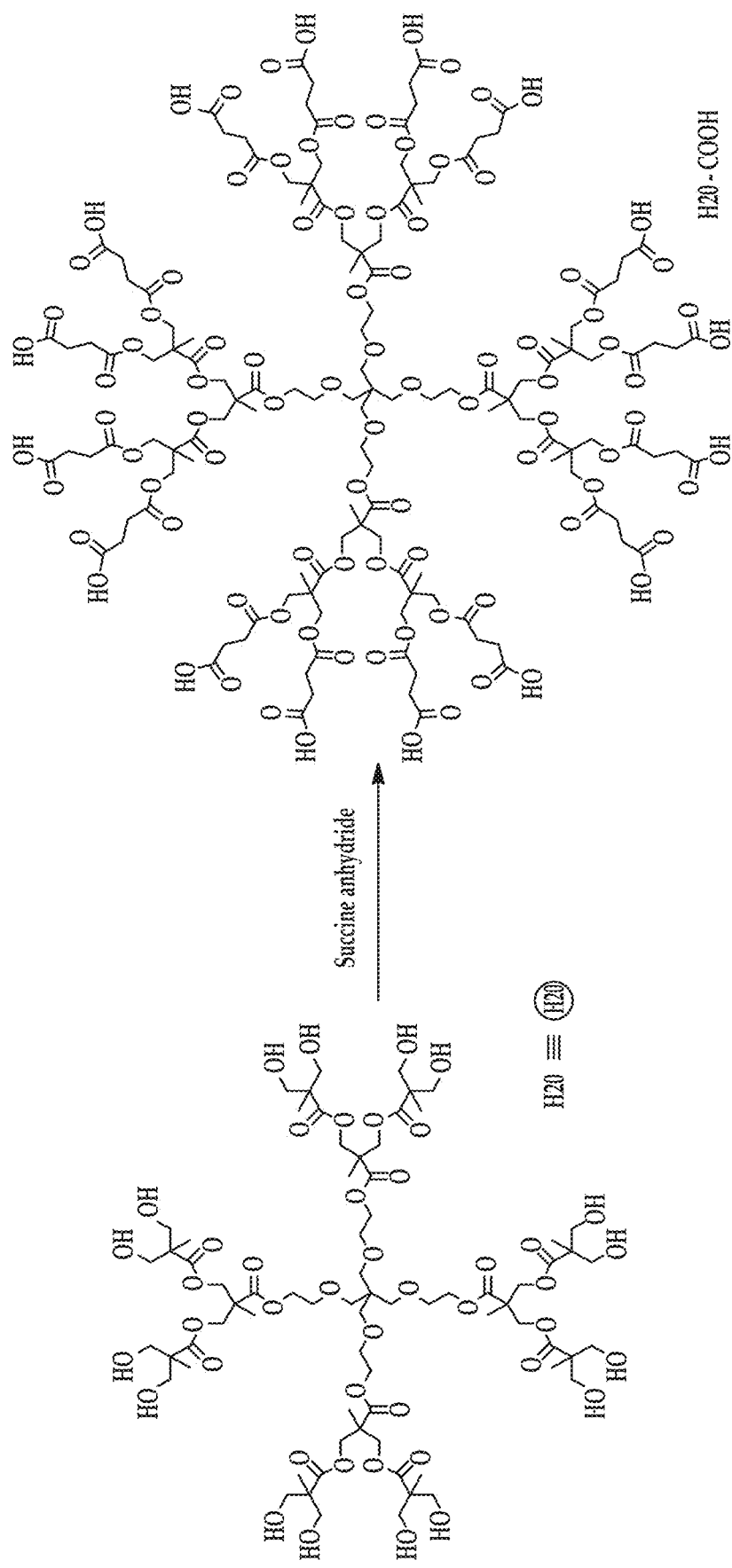
FIGS. 3A through 3C together illustrate one example of the synthesis of an example of the hyperbranched polymer (PEG-H20-PEI) disclosed herein.
Figure 3B:
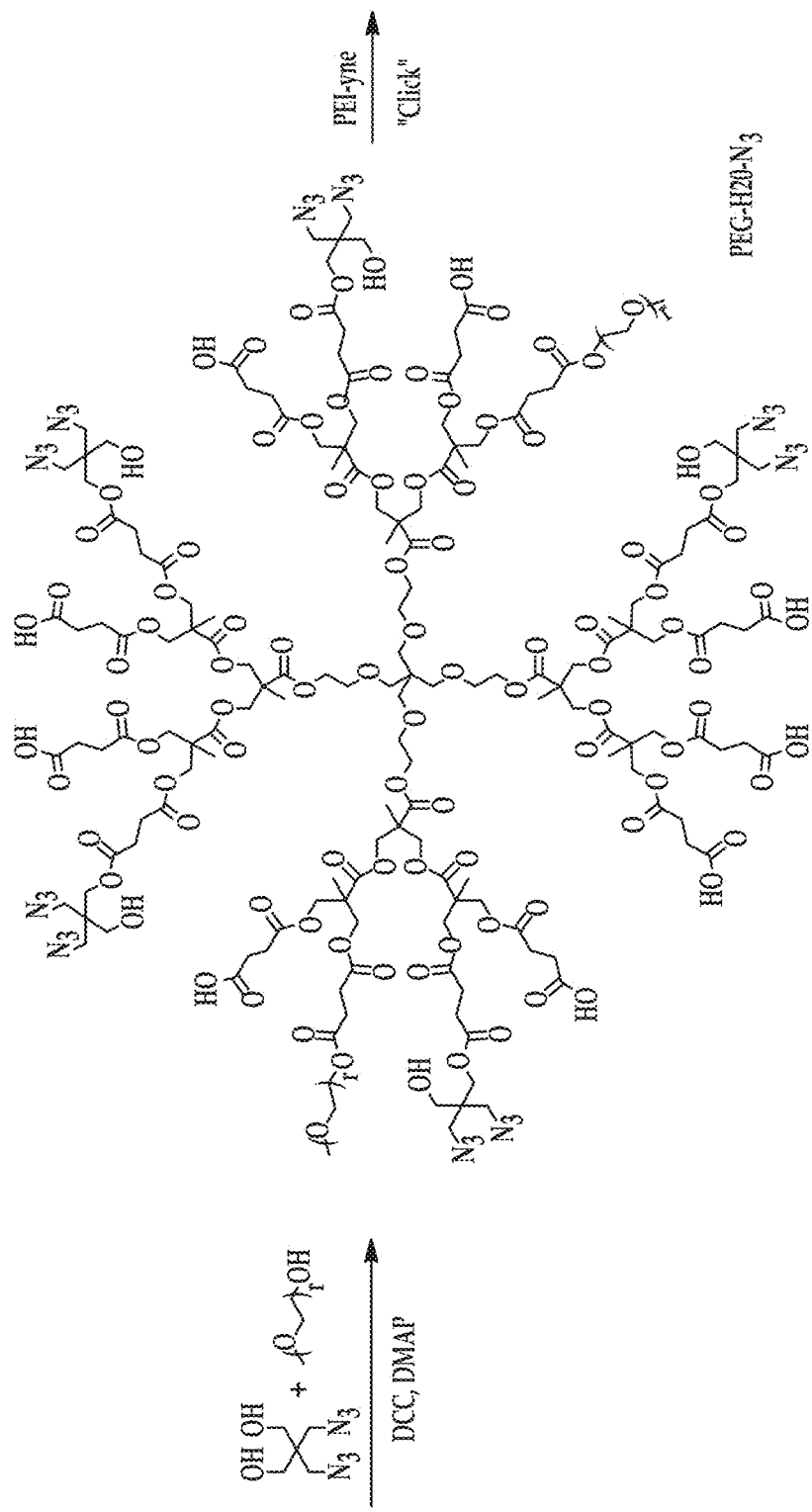
Figure 3C:
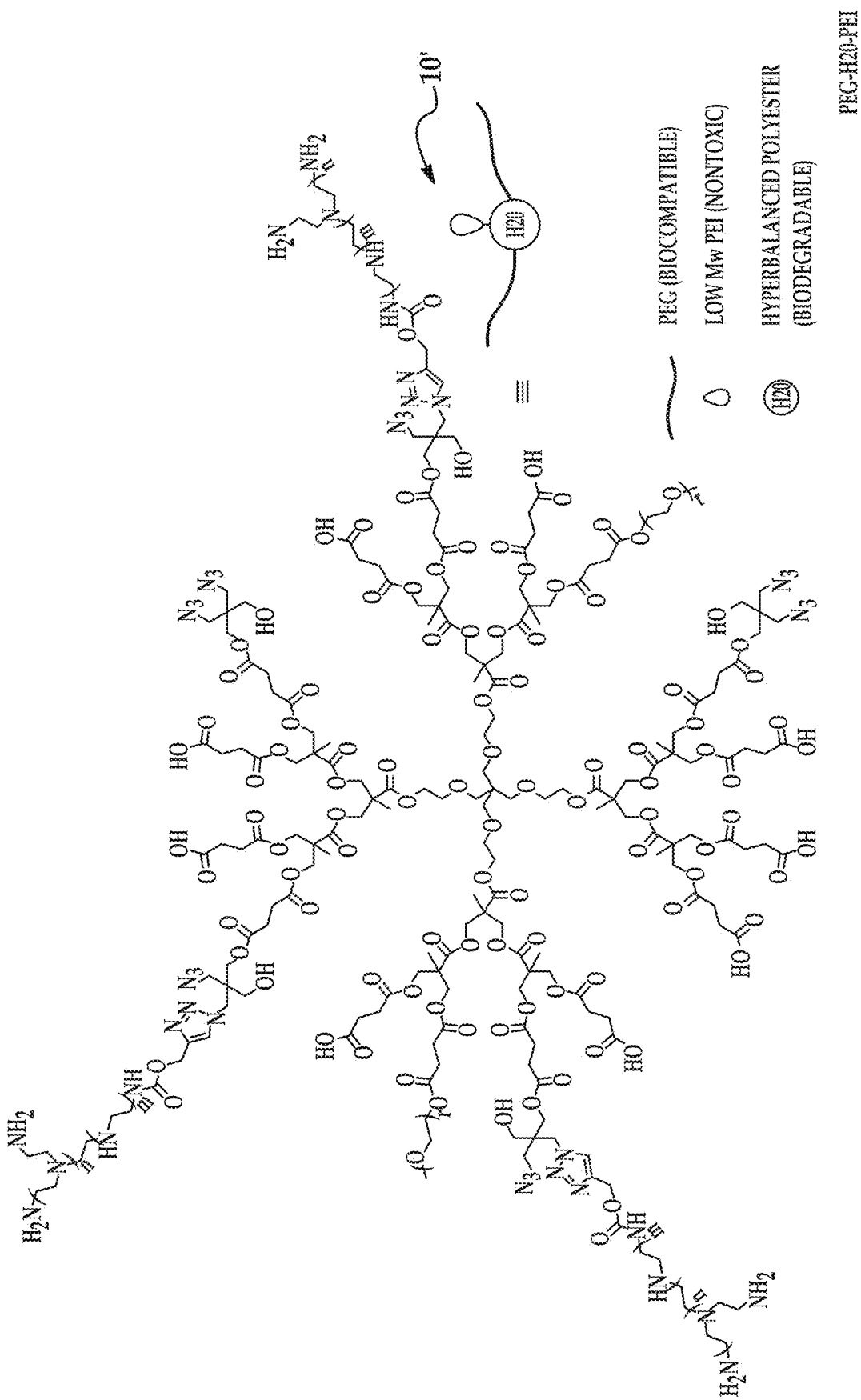

An example of the method for forming the hyperbranched polymer 10' is shown in FIGS. 3A through 3C. In this example, the hydroxyl groups of hyperbranched bis-MPA polyester (H20: 16 hydroxyls) are transferred to carboxyl groups through a reaction with succinic anhydride at room temperature (FIG. 3A). Then, azido (i.e., azide) groups and PEG chains are connected to the modified H20 (H-20-COOH) via a condensation reaction (in N,N'-dicyclohexyl-carbodiimide (DCC) and p-Dimethylaminopyridine (DMAP)) of the carboxyl groups of H20-COOH and the hydroxyl groups of 2,2-bis(azidomethyl)propane-1,3-diol and PEG at room temperature (e.g., from about 18° C. to about 25° C.). This forms PEG-H20-N$_3$ as shown in FIG. 3B. PEI-yne is conjugated to PEG-H20-N$_3$ via click chemistry (Click) to obtain PEG-H20-PEI (one example of the hyperbranched polymer 10'), as shown in FIG. 3C. In FIGS. 3A through 3C, r=2 to 50,000, m=2 to 200, and n=2 to 200. The formed hyperbranched polymer 10' may be made up of from about 20% to about 80%, or from about 30% to about 70%, of the hydrophilic PEG chains 12.

Figure 4:
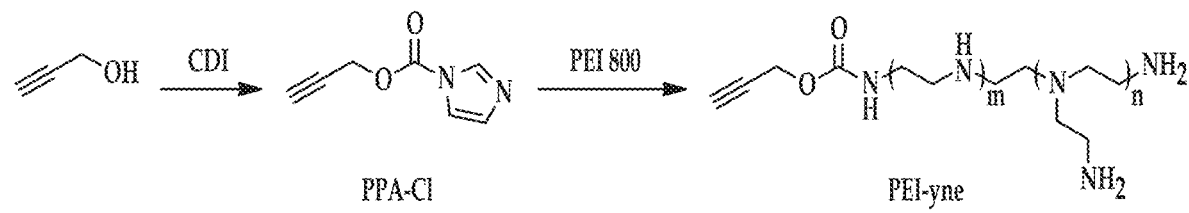
FIG. 4 illustrates one example of the synthesis of PEI-yne.

PEI-yne used in the synthesis of either the linear polymer 10 or the hyperbranched polymer 10' may be formed via the method shown in FIG. 4. In this example, propargyl alcohol is reacted with 1,1'-carbonyldiimidazole (CDI) at room temperature to obtain a propargyl ester of carbonylimidazole (PPA-CI). Then, polyethyleneimine (PEI, Mw 800 Da) is reacted with PPA-CI to generate PEI-yne. It is to be understood that polyethyleneimine of other molecular weights within the range provided herein may be used.

Polyesters are unstable and can degrade if reacted with the amino compound PEI, and thus the combined syntheses shown in FIGS. 4 and 2 and FIGS. 4 and 3 have been designed using mild reaction conditions via click chemistry. The mild conditions include room temperature and stirring. The mild reaction conditions enable the conjugation of the cationic polymer PEI to the polyesters without the undesired polymer degradation.

Referring back to FIG. 1, the linear polymer 10 or the hyperbranched polymer 10' may be complexed with DNA or RNA 18. Examples of the RNA include miRNA, mRNA, and/or siRNA. Examples of the DNA include pDNA, cDNA, cpDNA, gDNA, msDNA, mtDNA, and/or rDNA. The DNA or RNA 18 attaches to the low molecular weight PEI 16 of the linear polymer 10 or the hyperbranched polymer 10' via electrostatic interaction.

As depicted in FIG. 1, the linear polymer polyplex 20 and the hyperbranched polymer polyplex 20' may be formed via self-assembly of the linear polymers 10 or the hyperbranched polymers 10' and the DNA or RNA 18. The polyplexes 20, 20' may be formed by adding a solution of the linear polymer 10 or the hyperbranched polymer 10' to a solution of the DNA or RNA 18. Both solutions may be water based solutions. The combined mixture is allowed to incubate at room temperature (e.g., from about 18° C. to about 25° C.) for a predetermined time (e.g., at least about 30 minutes). As illustrated in FIG. 1, the polyplexes 20, 20' may be in the form of spheres. The polyplex 20 may be a solid sphere surrounded by the PEG chains 12, while the polyplex 20' may be a spherical center portion sandwiched between inner and outer PEG chains 12.

More specifically, when the linear polymer 10 and DNA or RNA 18 self-assemble, the biocompatible, hydrophilic PEG chains 12 and can form a sheathing shell to protect the inner portion of the polyplex 20. The inner portion of the polyplex 20 includes the linear hydrophobic (e.g., polyester) chain 14, the low molecular weight PEI chains 16, and the complexed DNA or RNA 18. Additionally, when the hyperbranched polymer 10' and DNA or RNA 18 self-assemble, the hyperbranched, hydrophobic molecular core 14', the low molecular weight PEI chains 16, and the complexed DNA or RNA 18 form the central section 22 that is sandwiched between a first plurality of the hydrophilic PEG chains 12 (which make up a hydrophilic inner section of the polyplex 20') and a second plurality of the hydrophilic PEG chains 12 (which make up a hydrophilic outer section of the polyplex 20').

The self-assembled hyperbranched polymers 10' form a double shell-like charge distribution that may lower toxicity (charge density) and increases charge accessibility to the DNA or RNA 18. As such, the hyperbranched polymers 10' (in the form of the polyplex 20') may advantageously serve as a DNA or RNA 18 delivery carrier.

The polyplexes 20, 20' may be encapsulated in a biodegradable polymer matrix to form biodegradable spheres. Encapsulation may overcome the disadvantage of uncontrolled duration of current DNA or RNA delivery systems, in part because the encapsulating material enables controlled release durations.

These biodegradable spheres may have nanoscale dimensions (1 nm up to 1000 nm) or micron scale dimensions (e.g., from 1 μm to about 100 μm). Encapsulation may be performed via a double emulsion technique, such as a water-in-oil-in-water double emulsion. Encapsulation may also be performed, for example, by a simple emulsion technique, extrusion, phase separation, spray-drying, etc.

Any suitable biodegradable or erodible material may be used as the biodegradable polymer matrix, such as, for example poly(lactic-co-glycolic acid) (also known as poly (lactide-co-glycolide) (PLGA)). Other suitable examples of the biodegradable polymer include, but are not limited to poly(L-lactic acid) (PLLA), polyglycolic acid (PGA), polyanhydrides, poly(ortho ethers), polycaprolactone, poly(hydroxy butyrate), poly(phosphoesters), poly(propylene fumarate), polyphosphazenes, polycarbonates, polyethylene glycol (PEG), polyvinyl alcohol (PVA), polyurethane, collagen, gelatin, alginate, chitin, chitosan, pectin, copolymers thereof, and combinations thereof.

The biodegradable spheres may be used as is, or they may be mixed with or immobilized on a support structure. An example of the support structure includes a scaffold formed of a plurality of nano-fibers aggregated together and pores defined between at least some of the nano-fibers. The nano-fibers mimic the structure of the extracellular matrix (ECM), and thus may promote tissue regeneration. Additionally, the scaffold likely increases gene delivery vehicle-loading efficiency, decreases the amount of degradation product, facilitates cell-cell and cell-matrix interactions, and provides an easy path for nutrient and metabolic waste transfer, which together synergistically enhance tissue regeneration and integration with the host.

One specific example of the scaffold is referred to as a nanofibrous scaffold. The nanofibrous scaffold is characterized as a multi-level porous structure with regular spherical macro-scale pores (ranging from about 250 μm to about 425 μm in diameter), micro-scale interpore openings (i.e., openings that connect one macro-scale pore to another macro-scale pore) of about 100 μm, and spaces (less than 2 μm in diameter) between the nanofibers. While the pores of the scaffold are on the macro-scale or smaller, the scaffold itself has larger dimensions. For example, the thickness of the scaffold may be 1 mm or more, and the length and/or width of the scaffold may be 3 mm or more.

Another specific example of the scaffold is referred to as a nanofibrous hollow microsphere (NF-HMS). The nanofibrous hollow microsphere is characterized as a hollow structure having a single hollow core surrounded by a nanofibrous shell, and one or more openings formed in the nanofibrous shell. The entire hollow structure has a diameter ranging from about 5 μm to about 1000 μm, and the diameter of the opening ranges from about 5 μm to about 50 μm. The nanofibrous shell also includes spaces (less than 2 μm in diameter) that are present between the nanofibers.

Still another specific example of the scaffold is referred to as a nanofibrous spongy microsphere (NF-SMS). The NF-SMS are similar to the nanofibrous scaffolds and the nanofibrous hollow microspheres because they also include a nanofibrous architecture or a partially nanofibrous architecture, and have diameter ranging from about 5 μm to about 1000 μm. However, the NF-SMS are unlike the nanofibrous scaffolds and nanofibrous hollow microspheres because they are spongy. By "spongy," it is meant that the NF-SMS have a sponge-like architecture throughout the entirety of the microsphere. The sponge-like architecture includes interconnected porous walls and micro-scale pores formed among the interconnected porous walls.

The sponge-like architecture includes the porous walls that extend through an interior of the NF-SMS and also define an exterior of the NF-SMS. The porous walls consist of interconnected nanofibers and spaces (less than 2 µm in diameter) formed between the interconnected nanofibers. The sponge-like architecture also includes a plurality of micro-scale pores (ranging from about 1 µm to about 100 µm in diameter), interpore openings (i.e., openings that connect one micro-scale pore 20 to another micro-scale pore 20), and, as previously mentioned, spaces between the nanofibers.

The micro-scale pores are at least partially defined by the porous walls and are formed throughout the NF-SMS. As such, some of the micro-scale pores are positioned at the exterior of the NF-SMS and others are positioned within the interior of the NF-SMS. Each micro-scale pore has at least one interpore opening. The interpore opening connects two adjacent micro-scale pores. In other words, the interpore opening opens up one micro-scale pore to another micro-scale pore. Each interpore opening of the NF-SMS ranges from about 2 µm to about 80 µm in diameter. Some of the micro-scale pores also have an additional opening that opens the micro-scale pore to the environment surrounding the NF-SMS. It is to be understood that the micro-scale pores positioned within the interior of the NF-SMS include the interpore opening(s) but do not include the additional opening(s).

The scaffolds may be formed of any of the previously described biodegradable polymer matrix materials, and may be formed by any suitable technique. As an example, the nanofibrous scaffold and the NF-HMS may be formed via a combination of phase separation and sugar leaching. Examples of the NF-SMS may be formed via a reverse emulsification technique using a highly glycerol-philic polymer, such as i) a star-shaped poly(L-lactic acid) having X number of hydroxyl groups, where X≥4, and having an original hydroxyl density of 1/Y, where Y is the feed ratio of a monomer used to form the polymer to the number of hydroxyls on an initiator used to form the polymer and where Y is ≥100; or ii) a star shaped poly(L-lactic acid)-block-poly(L-amino acid) having an amino acid (e.g., lysine) content or a peptide content (e.g., RGD (Arg-Gly-Asp)) greater than or equal to 5%; or iii) a graft copolymer with poly(L-lactic acid) (e.g., poly((hydroxyethyl)methacrylate)-graft-poly(L-lactic acid) (PHEMA-g-PLLA), poly((hydroxyethyl)propylmethacrylate)-graft-poly(L-lactic acid), poly((hydroxyethyl)butyl acrylate)-graft-poly(L-lactic acid), etc.). Other examples of the NF-SMS may be formed via a traditional emulsification technique using a star-shaped poly(L-lactic acid) having X number of hydroxyl groups, where X>16, and an original hydroxyl density, 1/Y, ranging from about 1/150 to 1/100.

Other suitable materials for the scaffold or other support structures include inorganic materials or polymer/inorganic material composites. The support structure may also be another highly porous (e.g., having from about 80% to about 99% pores) structure or a hydrogel.

The biodegradable spheres may be mixed with the support structure. The weight ratio of biodegradable spheres to support materials ranges from 0.01% (1:10000) to 100% (1:1). As one example, the weight ratio of biodegradable spheres to support materials may be 1% (1:100).

Immobilization of the biodegradable spheres on the scaffold may be accomplished via a post seeding method. In an embodiment, the biodegradable spheres are dispersed in a non-solvent or a poor solvent of both the biodegradable spheres and the scaffold. The dispersion may be seeded onto the scaffold dropwise. The seeded scaffold may be exposed to a mixed solvent vapor for a predetermined time to strongly adhere the biodegradable spheres to the scaffold. Generally, the mixed solvent vapor does not dissolve either the scaffold or the biodegradable spheres, rather it causes them to adhere by partially dissolving one or both of the scaffold or the biodegradable spheres. The mixed solvent vapor may include vapors of hexane/tetrahydrofuran (THF), in a ratio ranging from 0:1 to 1:0 by volume. As one example, the hexane/tetrahydrofuran ratio may be about 9:1 by volume. The scaffold may then be dried to remove any solvent(s). Other examples of immobilizing the biodegradable spheres on the scaffold(s) include high temperature treatments, (partial) solvent exposure, or combinations thereof.

Immobilization and localization of the biodegradable spheres onto the scaffold may help to prevent unintended delivery of DNA or RNA to off-target cells.

Figure 5:
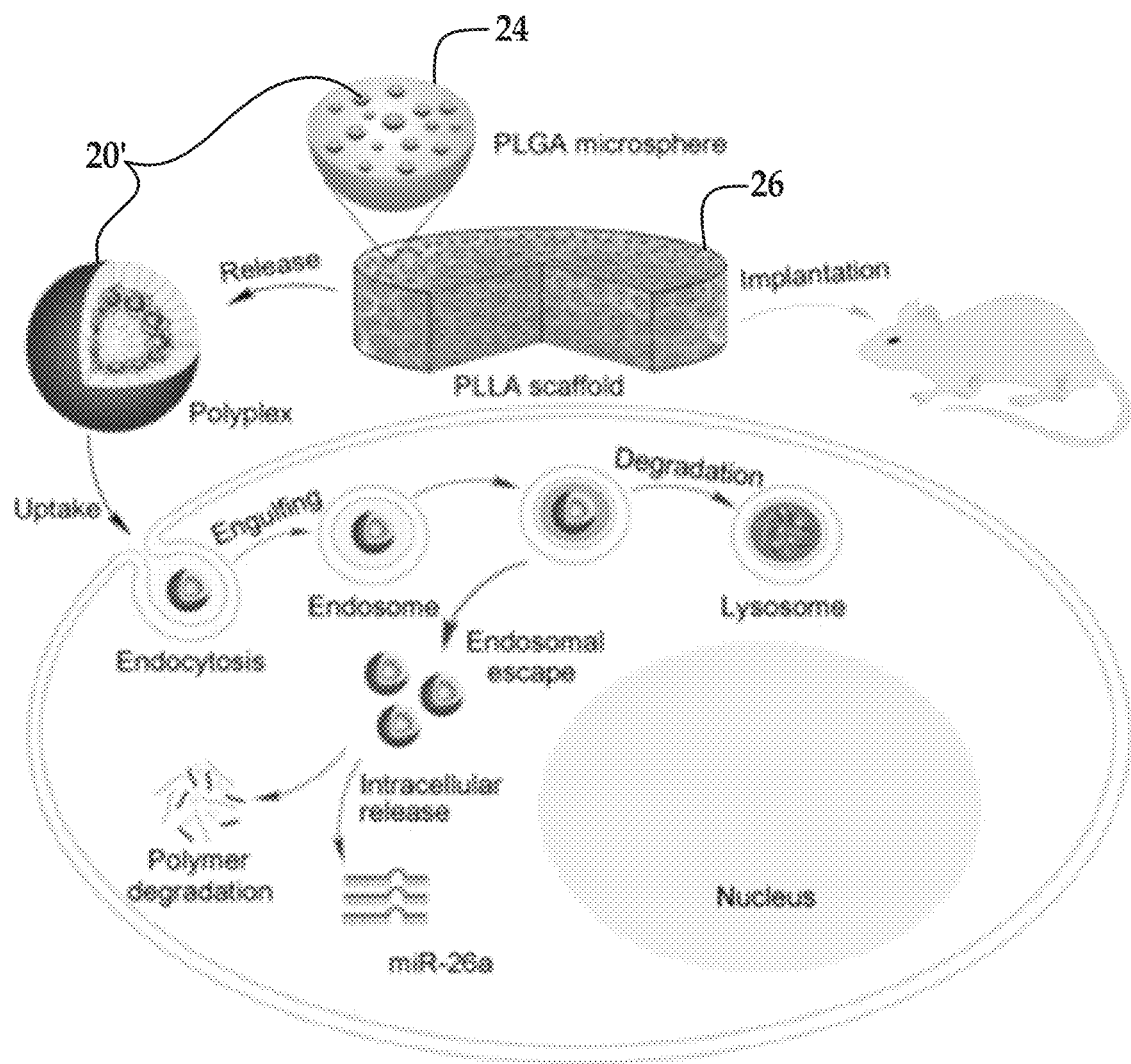
FIG. 5 is a schematic illustration of the two-stage delivery of miRNA from polyplex-embedded poly(lactide-co-glycolide) (PLGA) microspheres immobilized on a nanofibrous scaffold.

FIG. 5 schematically depicts an example of the biodegradable spheres 24 (including a plurality of the polyplexes 20' encapsulated therein) immobilized on and throughout a polymer scaffold 26. FIG. 5 also illustrates the two-stage delivery of miRNA (one example of RNA 18) from PLGA microspheres 24 immobilized on a PLLA nanofibrous scaffold 26 into cells in vitro and in vivo. The cationic polyplexes disclosed herein may be utilized to protect miRNAs (or other RNA or DNA) from extracellular degradation in the long journey into cells. As shown in FIG. 5, the PLGA microsphere-incorporated PLLA scaffold may be subcutaneously implanted into a mouse or rat. In an example, the microsphere-incorporated scaffold may be injected into the nucleus pulposus area of the mouse or rat tail. The polyplexes 20' released from the PLGA microspheres 24 (on the PLLA scaffold 26) may be taken into the cell through endocytosis. The polyplexes 20' are engulfed to an endosome. ATP-mediated proton accumulation increases the acidity of the endosome to a pH ranging from about 5.0 to about 6.2, which is significantly lower than the pH value in the cytosol or intracellular space (pH 7.4). The polyplex 10' has the ability to buffer the endosomal vesicle through the proton buffering effect of PEI. In other words, after the polymer/miRNA polyplexes 20' go across the cell membrane and are enwrapped in endosomes, the cationic PEI component can buffer the acidic environment in the endosomal vesicles, preserving the biological activity of the miRNAs and causing endosomal swelling and lysis, thus releasing the polyplex 20' into the cytoplasm. Intracellular release of the DNA or RNA 18 (shown as miR-26a in FIG. 5) in the cytosol after polymer degradation allows its regulation of gene expression.

To further illustrate the present disclosure, examples are given herein. It is to be understood that these examples are provided for illustrative purposes and are not to be construed as limiting the scope of the present disclosure.

EXAMPLES

Example 1

Materials
Polyethyleneimine (PEI, Mw 800 Da and 25 kDa), polyethylene glycol methyl ether (PEG, Mw 2000, 5000, 10000, and 20000 Da), and hyperbranched bis-MPA polyester (referred to in this example as Hx, where Hx is H20: 16 hydroxyl, H30: 32 hydroxyl, or H40: 64 hydroxyl) were purchased from Sigma-Aldrich and used as received. The fluorescent analog, NBD cholesterol, is a probe that localizes in the membrane's interior and is useful for investigating lipid transport processes as well lipid-protein interactions. This analog was purchased from life technologies. α-Azido-ε-caprolactone (α-$N_3$-ε-CL) was synthesized as described in Fuhrmann, K., et al. "PEG nanocages as non-sheddable stabilizers for drug nanocrystals" ACS nano 6, 1667-1676 (2012). A commercial miR-26a mimic was used as the miRNA in this example.

Synthesis of PEI-yne 1,1'-Carbonyldiimidazole (CDI, 7.30 g, 45 mmol) was dissolved in 50 mL of dichloromethane. Propargyl alcohol (1.50 mL, 26 mmol) was added dropwise. The reaction mixture was stirred at room temperature for about 1 hour and was washed with 40 mL of water three times. The organic phase was dried by anhydrous magnesium sulfate and the filtrate was concentrated under reduced pressure to obtain the propargyl ester of carbonylimidazole (PPA-CI) as a white solid. Yield: 89%. $^1$H NMR (400 MHz, $CDCl_3$, ppm): 8.17 (s, 1H, NCHN), 7.46 (s, 1H, NCHCHN), 7.10 (s, 1H, NCHCHN), 5.01 (s, 2H, OCH2C), 2.65 (s, 1H, C≡CH).

Polyethyleneimine (PEI, Mw 800 Da, 2.40 g, 3.0 mmol) was dissolved in a mixture of chloroform (25 mL) and methanol (5 mL). A solution of PPA-CI (0.45 g, 3.0 mmol) in 4.5 mL of chloroform was added dropwise over a period of 30 minutes at an ice-cooled temperature. After the mixture was refluxed for about 6 hours, the solvents were removed by rotary evaporation. The residue was dissolved in 10 mL of water. Then, the solution was neutralized by 1 M hydrochloric acid standard solution and washed with 5 mL of chloroform three times. The aqueous phase was lyophilized to obtain PEI-yne as a yellow solid. Yield: 85%. FT-IR (KBr, $cm^{-1}$): 2130 ($v_{C≡CH}$). $^1$H NMR (400 MHz, $D_2O$, ppm): 4.68 (s, 2H, $OCH_2C$), 3.81-2.60 (m, 74H, $NCH_2$), 2.47 (s, 1H, C≡CH).

Synthesis of PEG-Hx-$N_3$

Hx (2.00 g) and triethylamine (0.5 mL) were dissolved in 50 mL of THF. Succinic anhydride (3.50 g, two-fold molar excess) was added. The reaction mixture was stirred at room temperature for about 24 hours and the obtained floc-like solid precipitated from the solution was washed with THF and diethyl ether to remove the residual succinic anhydride. The residue was dried under vacuum to give Hx-COOH as a white solid. Yield: 62-73%. FT-IR (KBr, $cm^{-1}$): 1740 ($v_{C=O}$). $^1$H NMR (400 MHz, $D_2O$, ppm): 4.29 (br s, $CH_2O$), 2.84-2.51 (m, $CH_2CH_2COOH$), 1.27 (s, $CH_3$).

Hx-COOH (3.2 mmol of carboxyl groups), N,N'-dicyclohexylcarbodiimide (0.990 g, 4.8 mmol), and 4-dimethylaminopyridine (0.586 g, 4.8 mmol) were dissolved in 50 mL of dimethylformamide. 2,2-bis(azidomethyl)propane-1,3-diol (0.300 g, 1.6 mmol) and PEG (Mw 2000 Da, 3.200 g, 1.6 mmol) were added. The reaction was stirred at room temperature for 24 hours. The reaction mixture was filtered and concentrated. The residue was then transferred into a dialysis bag (MWCO 3500 Da) and dialyzed against a continuous flow of deionized water for 2 days, during which the water was renewed every 8 hours. The product was obtained by lyophilization to give a flocculent solid. Yield: 34-46%. FT-IR (KBr, $cm^{-1}$): 2105 ($v_{N3}$), 1742 ($v_{C=O}$). $^1$H NMR (400 MHz, $CDCl_3$, ppm): 4.22 (br s, $CH_2O$ of Hx), 4.06 (br s, $CCH_2OH$ and $CCH_2OOC$), 3.88-3.56 (m, $OCH_2CH_2$ of PEG), 3.46 (br s, $CH_2N_3$), 3.38 (s, $CH_3$ of PEG), 2.78-2.56 (m, $CH_2CH_2COO$ of Hx), 1.25 (s, $CH_3$ of Hx).

Synthesis of PEG-Hx-PEI (Hyperbranched Polymer 10') Via Click Chemistry

PEG-Hx-$N_3$ (1 equiv. $N_3$), PEI-yne (2 equiv. alkynyl), copper(I) bromide (2 equiv.), and triethylamine (2 equiv.) were dissolved in THF-water mixture (1:1 by volume). The mixture was stirred for about 3 hours at 35° C. The solution was then transferred into a dialysis bag (MWCO 3500 Da) and dialyzed against a continuous flow of deionized water for 2 days, during which the water was renewed every 8 hours. The product was obtained by lyophilization to give a flocculent solid. Yield: 44-60%. FT-IR (KBr, $cm^{-1}$): 2106 ($v_{N3}$). 1743 ($v_{C=O}$), 1635 ($v_{triazole}$). $^1$H NMR (400 MHz, $D_2O$, ppm): 3.79-3.58 (m, $OCH_2CH_2$ of PEG), 3.58-2.60 (m, $NCH_2$ of PEI). $^1$H NMR (400 MHz, DMSO-$d_6$, ppm): 4.15 (br s, $CH_2O$ of Hx), 3.99 (br s, $CCH_2OH$ and $CCH_2OOC$), 3.73-3.46 (m, $OCH_2CH_2$ of PEG), 2.72-2.54 (m, $CH_2CH_2COO$ of Hx), 1.18 (s, $CH_3$ of Hx).

Synthesis of PEG-P($N_3$CL-CL) Via Ring-Opening Polymerization

A round bottom flask pretreated with trimethylchlorosilane was charged with 1.0 g of PEG (Mw 5000, 10000 or 20000 Da) and heated at 100° C. under reduced pressure (oil pump) for about 4 hours. α-$N_3$-ε-CL (0.33 g, 2.0 mmol), ε-caprolactone (ε-CL, 0.456 g, 4.0 mmol), and 60 μL of 0.1 M Sn(Oct)$_2$ solution in anhydrous toluene were added. The flask was evacuated and charged with nitrogen three times, and then sealed under vacuum with a magnetic stirring bar inside. After the mixture was stirred at 130° C. for about 24 hours, the polymerization was quenched by immersing the flask in a cool water bath. The product was purified by precipitation from chloroform with cold methanol-diethyl ether mixture (1:1 by volume) three times and dried under vacuum to give a white solid. Yield: 84-88%. FT-IR (KBr, $cm^{-1}$): 2111 ($v_{N3}$), 1749 ($v_{C=O}$). $^1$H NMR (400 MHz, $CDCl_3$, ppm): 4.22-4.11 (t, $OCOCH(N_3)CH_2CH_2CH_2CH_2$), 4.08-3.96 (t, $OCOCH_2CH_2CH_2CH_2CH_2$), 3.88-3.80 (t, $OCOCH(N_3)CH_2CH_2CH_2CH_2$), 3.74-3.58 (br s, $OCH_2CH_2$ of PEG), 3.38 (s, $CH_3$ of PEG), 2.38-2.22 (t, $OCOCH_2CH_2CH_2CH_2CH_2$), 1.83-1.58 (m, $CH_2CH_2CH_2CH_2O$ of $N_3CL$ and CL), 1.45-1.28 (m, $CH_2CH_2CH_2CH_2O$ of $N_3CL$ and CL).

Synthesis of PEG-PE-PEI (Linear Polymer 10) Via Click Chemistry

PEG-P($N_3$CL-CL) (0.16 mmol of $N_3$), PEI-yne (0.162 g, 0.55 mmol of alkynyl), copper(I) bromide (0.066 g, 0.46 mmol), and triethylamine (0.047 g, 0.46 mmol) were dissolved in THF-water mixture (1:1 by volume). The mixture was stirred for about 3 hours at 35° C. The solution was then transferred into a dialysis bag (MWCO 3500 Da) and dialyzed against a continuous flow of deionized water for 2 days, during which the water was renewed every 8 hours. The product was obtained by lyophilization to give a flocculent solid. Yield: 68-75%. FT-IR (KBr, $cm^{-1}$): 2109 ($v_{N3}$), 1750 ($v_{C=O}$), 1637 ($v_{triazole}$). $^1$H NMR (400 MHz, $D_2O$, ppm): 3.88-3.60 (m, $OCH_2CH_2$ of PEG), 3.60-2.72 (m, $NCH_2$ of PEI). $^1$H NMR (400 MHz, DMSO-$d_6$, ppm): 4.14-4.03 (m, $OCOCH_2CH_2CH_2CH_2$), 3.62 (br s, $OCH_2CH_2$ of PEG), 2.35-2.20 (t, $OCOCH_2CH_2CH_2CH_2$), 1.84-1.56 (m, CH$_2$CH$_2$CH$_2$CH$_2$O of N$_3$CL and CL), 1.47-1.30 (m, CH$_2$CH$_2$CH$_2$CH$_2$O of N$_3$CL and CL).

Polymer Characterization

The FT-IR spectra were recorded on a Perkin Elmer BX spectrometer. $^1$H NMR analyses were performed on a Varian INOVA-400 spectrometer operating at room temperature. Molecular weight and molecular weight distribution were determined by a Waters 440 gel permeation chromatograph (GPC) at 35° C. THF was used as an eluent at a flow rate of 1.0 mL/min. Polystyrene standards with narrow distributions were used to generate a calibration curve. Elemental analyses were carried out by Atlantic Microlab Inc. The PEI contents in the polymers were calculated from the nitrogen contents determined using elemental analysis. Then, the molecular weights of polymers were estimated using nuclear magnetic resonance (NMR), which were consistent with those determined using gel permeation chromatography (GPC).

Figure 6:
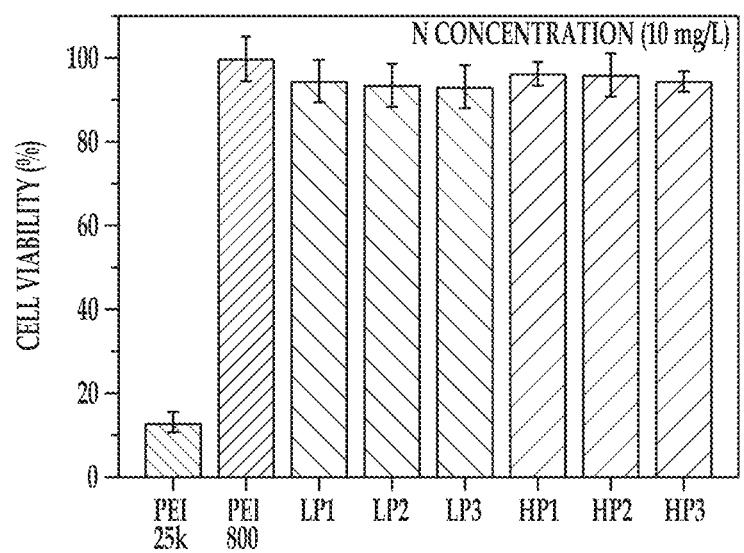
FIG. 6 is a graph depicting the cell viability (%) for a high molecular weight polyethyleneimine (PEI), a low molecular weight PEI, and several examples of the linear and hyperbranched polymers disclosed herein.

Table 1 illustrates the properties of the three linear polymers (LP) that were generated and the three hyperbranched polymers (HP) that were generated.

of the solution of the cells cultured with the medium only. The results are shown in FIG. 6. As depicted, PEI 25 kDa had a very high toxicity while PEI 800 was nontoxic. After PEI conjugation, both the linear polymers and the hyperbranched polymers had a very low cytotoxicity. The hyperbranched cationic polymers can degrade through the hydrolysis of their ester bonds.

General Preparation of Polymer/RNA Polyplexes

Designed polymer solutions (1.0 mg/mL) were added slowly to RNA solutions containing 60 pmol of RNA. The amount of polymer added was calculated on the basis of chosen N/P ratios of polymer/RNA (N nitrogen atoms of the polymer over P phosphates of RNA). The mixture was incubated at room temperature for 30 minutes for the complex formation.

Preparation and Characterization of Polymer/miRNA Polyplexes miRNA was labeled by the freshly prepared tungstic acid utilizing the coupling interactions between phosphorus (P)

TABLE 1

| No. | Sample[a] | Elemental Analysis | | | No. of PEI[b] | $W_{PEG}$ (%)[c] | $W_{PEI}$ (%)[c] | $M_n$ (NMR) | $M_n$ (GPC) | PDI (GPC)[d] |
| --- | --- | --- | --- | --- | --- | --- | --- | --- | --- | --- |
| | | C (%) | H (%) | N (%) | | | | | | |
| LP1 | PEG-PE$_{26}$-PEI$_{3.0}$ | 48.18 | 7.90 | 6.95 | 3.0 | 46.3 | 22.2 | 10800 | 15400 | 1.31 |
| LP2 | PEG-PE$_{52}$-PEI$_{5.8}$ | 48.08 | 8.25 | 6.83 | 5.8 | 46.7 | 21.7 | 21400 | 24500 | 1.27 |
| LP3 | PEG-PE$_{106}$-PEI$_{12.5}$ | 47.89 | 8.35 | 7.16 | 12.5 | 45.6 | 22.8 | 43900 | 45800 | 1.34 |
| HP1 | PEG$_2$-H20-PEI$_{2.9}$ | 49.72 | 7.90 | 7.20 | 2.9 | 39.2 | 22.7 | 10200 | 12800 | 1.41 |
| HP2 | PEG$_5$-H30-PEI$_{6.5}$ | 50.64 | 7.75 | 7.16 | 6.5 | 43.7 | 22.7 | 22900 | 27100 | 1.39 |
| HP3 | PEG$_9$-H40-PEI$_{11.7}$ | 48.64 | 7.67 | 7.18 | 11.7 | 43.8 | 22.8 | 41100 | 45300 | 1.29 |

[a]The molecular weights of PEG in LP1, LP2, and LP3 were 5000, 10000, and 20000 Da, respectively. The molecular weight of PEG in the hyperbranched polymers PEG-Hx-PEI was 2000 Da.
[b]The number of PEI in the polymers was calculated through the content of nitrogen atoms determined by element analysis.
[c]The weight ratios of PEG and PEI in the polymers were calculated when the molecular weight was determined from $^1$H NMR spectra.
[d]PDI = Polydispersity index Cytotoxicity Assay of Polymer A cytotoxicity assay was carried out on the basis of an MTT assay on osteoblasts. The osteoblasts were seeded in 96-well plates at an initial density of 5000 cells/well in 200 μL of DMEM complete medium. The cells were allowed to grow for 24 hours. The original medium was replaced with 100 μL of fresh medium. PEG-PE-PEI, PEG-Hx-PEI, PEI 800 Da, or PEI 25 kDa solution was added to the medium at 10 μg/mL of nitrogen atoms concentration in the medium. Each dosage was replicated in 4 wells. Treated cells were incubated at 37° C. under a humidified atmosphere of 95% air and 5% CO$_2$ for 24 hours. MTT reagent (20 μL in PBS, 5 mg/mL) was added to each well, and the cells were incubated for another 4 hours at 37° C. 100 μL of DMSO were added to each well until all crystals dissolved.

The absorbance at 570 nm of the solution in each well was recorded using a ThermoElectron 3001 Varioskan Flash Spectral Scanning Microplate Reader. Cell viability was calculated according to the following equation: cell viability (%)=(ODsample−ODblank)/(ODcontrol−ODblank)×100, where ODsample is the absorbance of the solution of the cells cultured with the polymer or PEI; ODblank is the absorbance of the medium; and ODcontrol is the absorbance atoms in miRNA and tungsten (W) atoms in tungstic acid. W is a heavy element and can be used as a negative staining reagent for TEM imaging. 10 mL of sodium tungstate aqueous solution (0.15 mol/L) was added dropwise to 6 mL of HCl aqueous solution (0.8 mol/L) at room temperature. The precipitate was collected and washed to obtain the activated tungstic acid. The activated tungstic acid was added to miRNA aqueous solution with 3 of W/P molar ratio. The W-incorporated miRNA solution was purified by centrifugation and stored at −80° C.

The W-incorporated miRNA solution was used to prepare polymer/miRNA polyplexes with both the linear polymers (LP) and the hyperbranched polymers (HP). The polyplexes at N/P ratio of 10 were prepared by adding an appropriate volume of W-incorporated miRNA solution to an appropriate volume of polymer solution (1.0 mg/mL) and incubating at room temperature for 30 minutes. One drop of polymer/miRNA polyplex solution was added onto a carbon-coated copper grid. The grid was allowed to dry under ambient conditions. A JEOL JEM-3011 transmission electron microscope was used to characterize the morphology of polymer/miRNA polyplexes.

Figure 7A:
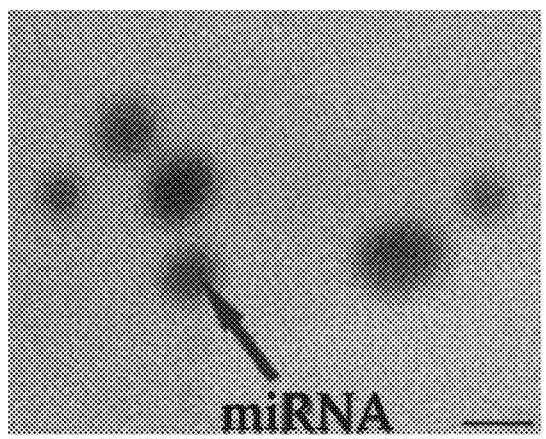
FIGS. 7A and 7B are transmission electron microscope (TEM) images of polyplexes formed form self-assembled complexes of a linear polymer and miRNA and polyplexes formed form self-assembled complexes of a hyperbranched polymer and miRNA, respectively.
Figure 7B:
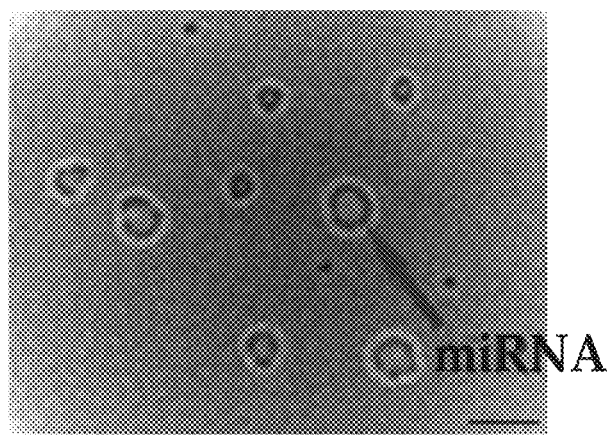

FIGS. 7A and 7B respectively illustrate the linear polymer (LP3)/miRNA and hyperbranched polymer (HP3)/miRNA TEM images. The TEM images show clear differences between the LP/miRNA polyplexes and the HP/miRNA polyplexes. The dark domains in the TEM images were W-labeled miRNA and the white areas were the polymers (PEG and polyesters). The miRNA in the LP/miRNA polyplexes aggregated into the spherical cores, which appeared as dark spheres under TEM (FIG. 7A). However, for the HPs, the miRNA first complexed with the PEI on the outer shell of the hyperbranched polyester cores. The HP molecular cores and PEI/miRNA shells together assembled into the hydrophobic shell between the outer PEG chains and the inner PEG core of the 3-layer nanosphere. The HP molecular cores and PEI/miRNA shells together appeared as a dark hollow spherical circle under the TEM (FIG. 7B).

Figure 8:
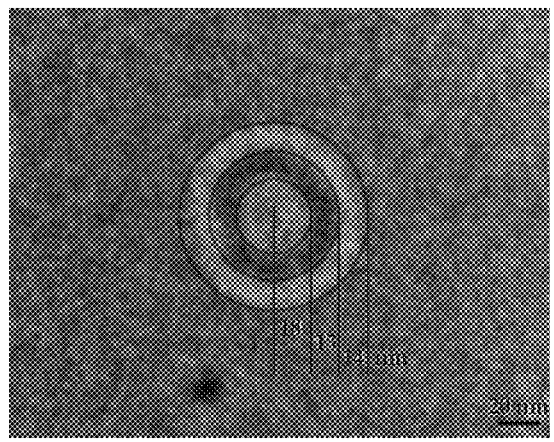
FIG. 8 is a TEM image of an example of a polyplex formed from the hyperbranched polymer (PEG-H40-PEI) with tungsten (W)-incorporated miRNA, where the thicknesses of the layers/sections of the polyplex are shown.

The thickness of the outer layer/section and the radius of the inner core/section were found to be on the same order of magnitude, approximately the theoretical length of the PEG chains. The thickness of the different layers from the TEM image of HP3 with W-incorporated miRNA is shown in FIG. 8. There are two C—O (143 μm) and a C—C (154 μm) bond in each repeating unit of PEG. The bond angles of C—C—O and C—O—C are both about 110°. So, the length of PEG (Mw 2000) was calculated according to the following equation:

$$L=(2\cdot 143\cdot \sin 55 + 154\cdot \sin 55)\cdot 45 = 16 \text{ nm}.$$

As depicted in FIG. 8, the thickness of the outer section and the inner section were around 16 nm (±2), which indicates that the outer section and the inner section were both hydrophilic sections composed of PEG. The hydrophobic polyester and polyplexes were in between the outer section and the inner section. These results indicate that HP3 with miRNA forms a 3-layer nanoparticle.

Agarose Gel Retardation

The double shell-like charge (PEI) distribution may have lowered local charge density (compared with the high molecular weight PEI) and therefore achieved lower cytotoxicity, and may also have imparted the higher accessibility of the PEI for miRNA binding and therefore achieved the higher complexing efficiency than that of cationic groups in the linear polymers. To test this hypothesis, the complexing capacity of these cationic polymers with RNA was examined using agarose gel electrophoresis. When a cationic polymer and RNA form a stable polyplex with positive surface potential, the RNA band would stay in the original position after being electrophoresed, i.e., the cationic polymer retarded the RNA migration.

Figure 9:
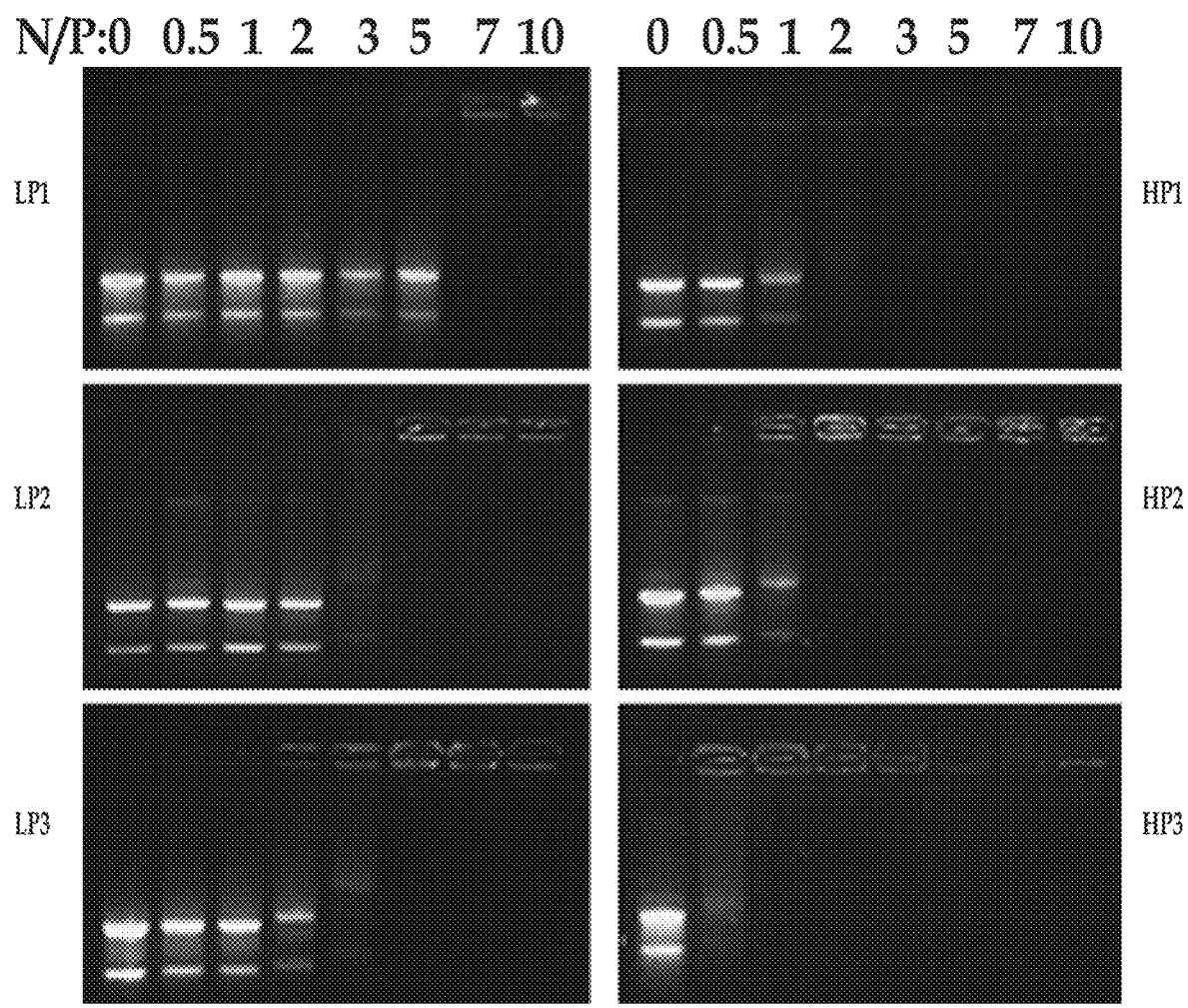
FIG. 9 is a photograph of UV visualized (254 nm) RNA bands of several example linear polymer polyplexes (left three images) and hyperbranched polymer polyplexes (right three images) that were electrophoresed on a 0.7% agarose gel containing GelRed with Tris-acetate (TAE) running buffer (pH 8) at 80 V for 45 minutes.

A 10 μL sample of the polyplex solution mixed with 4 μL of 1× loading buffer was loaded to agarose gel. The polyplexes were electrophoresed on a 0.7% agarose gel containing GelRed with Tris-acetate (TAE) running buffer (pH 8) at 80 V for 45 minutes. RNA bands were visualized by an UV (254 nm) illuminator and photographed with a BioSpectrum Imaging System (USA). The images are shown in FIG. 9. The hyperbranched polymers (HP1, HP2, HP3) were found to retarded RNA migration at less polymer quantity than linear polymers when they have similar molecular weight and nitrogen content.

Comparison of HP Polyplexes with Lipoplexes and with LP Polyplexes

The stabilities of the HP/miRNA polyplexes and the commercial product lipofectamine 2000/miRNA lipoplexes were examined side-by-side using dynamic light scattering (DLS) and TEM. The results for the lipofectamine 2000/miRNA lipoplexes are shown in FIGS. 10A through 10D, and the results for the HP/miRNA polyplexes are shown in FIGS. 11A through 11D.

Figure 10A:
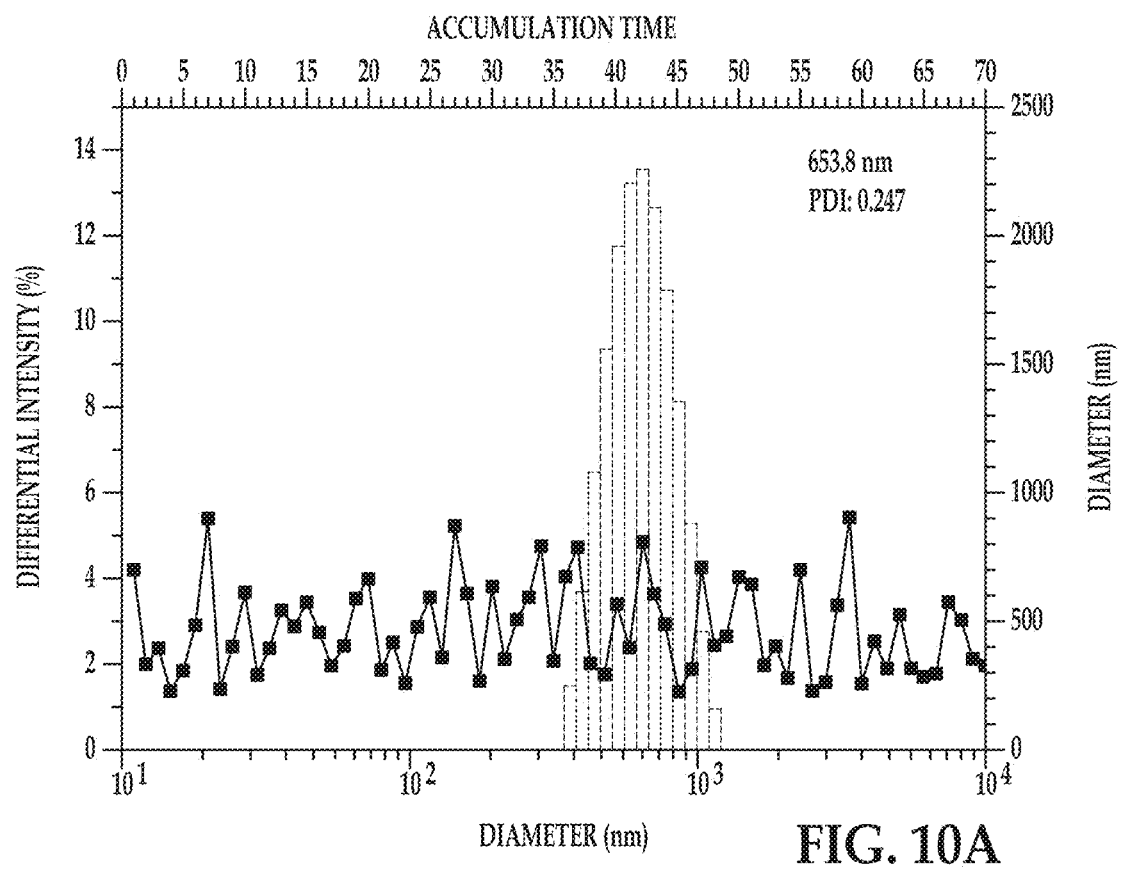
FIGS. 10A and 10B are size distribution profiles determined by dynamic light scattering (DLS) for lipofectamine/miRNA lipoplexes before sonication (10A) and after sonication (10B)
Figure 10B:
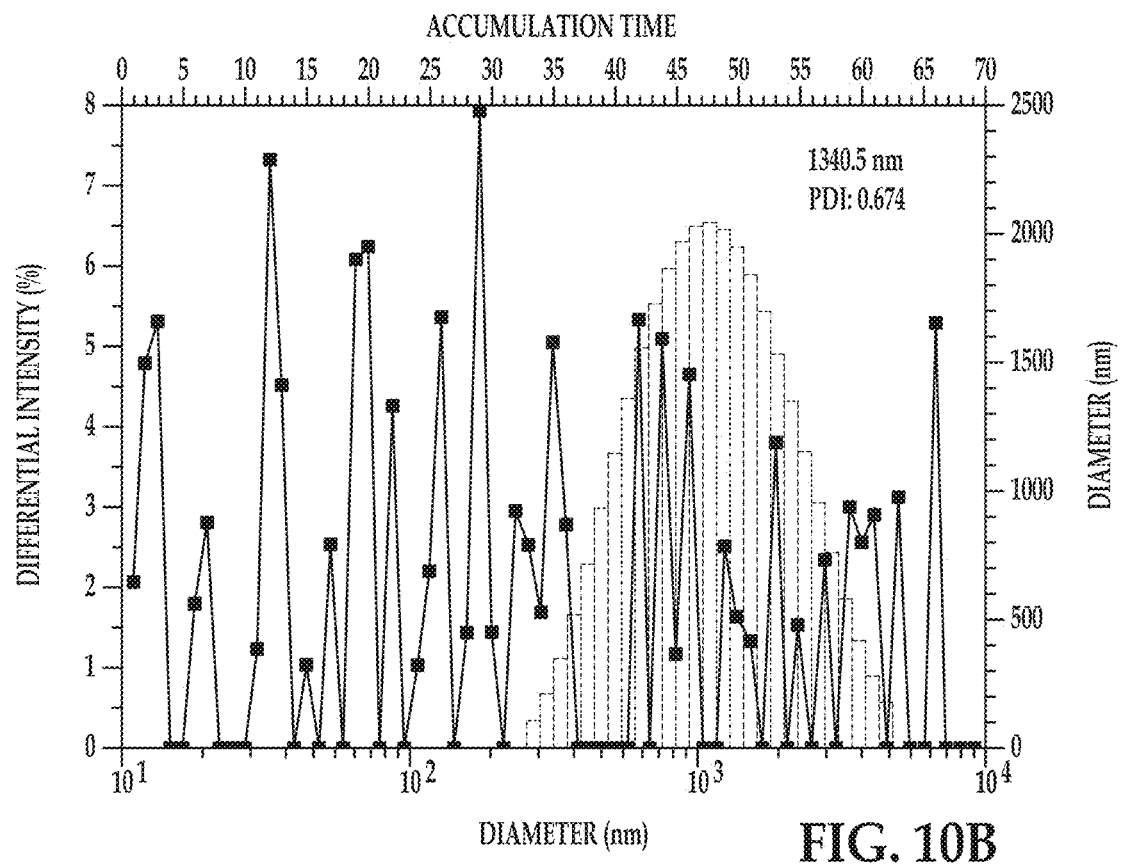
Figure 10C:
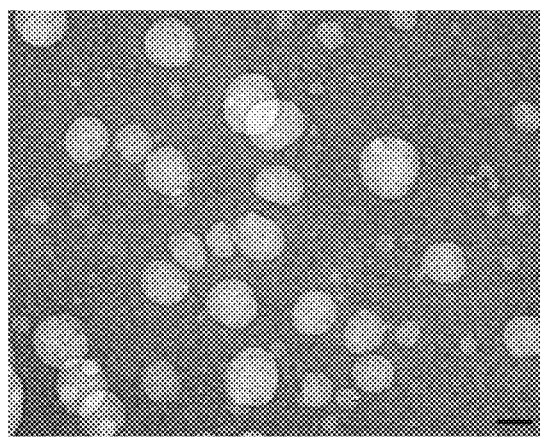
FIGS. 10C and 10D are morphology images of the lipofectamine/miRNA lipoplexes before sonication (10C) and after sonication (10D), as characterized by TEM (scale bar, 200 nm)
Figure 10D:
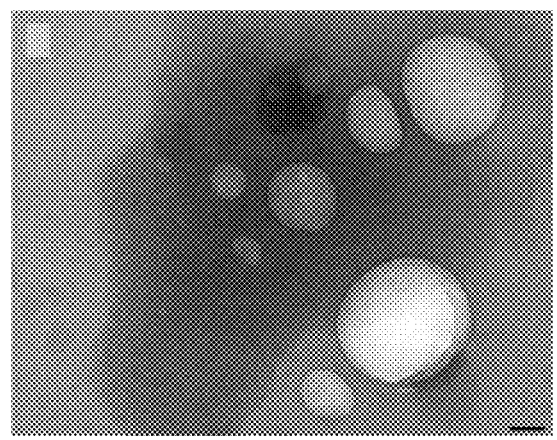

In FIGS. 10A and 10B, respectively, the size distribution profiles determined by DLS for lipofectamine/miRNA lipoplexes are shown before sonication and after sonication. Morphology images (characterized by TEM (scale bar, 200 nm)) of the lipofectamine/miRNA lipoplexes before sonication are shown in FIG. 10C, and after sonication are shown in FIG. 10D. The lipoplexes became bigger and wider after sonication, which indicated that lipoplexes were unstable under sonication. More particularly, the lipoplexes were larger in size with an average diameter of about 653 nm and were unstable under sonication, resulting in a broader size distribution and size increase to 1341 nm due to fragmentation and aggregation.

Figure 11A:
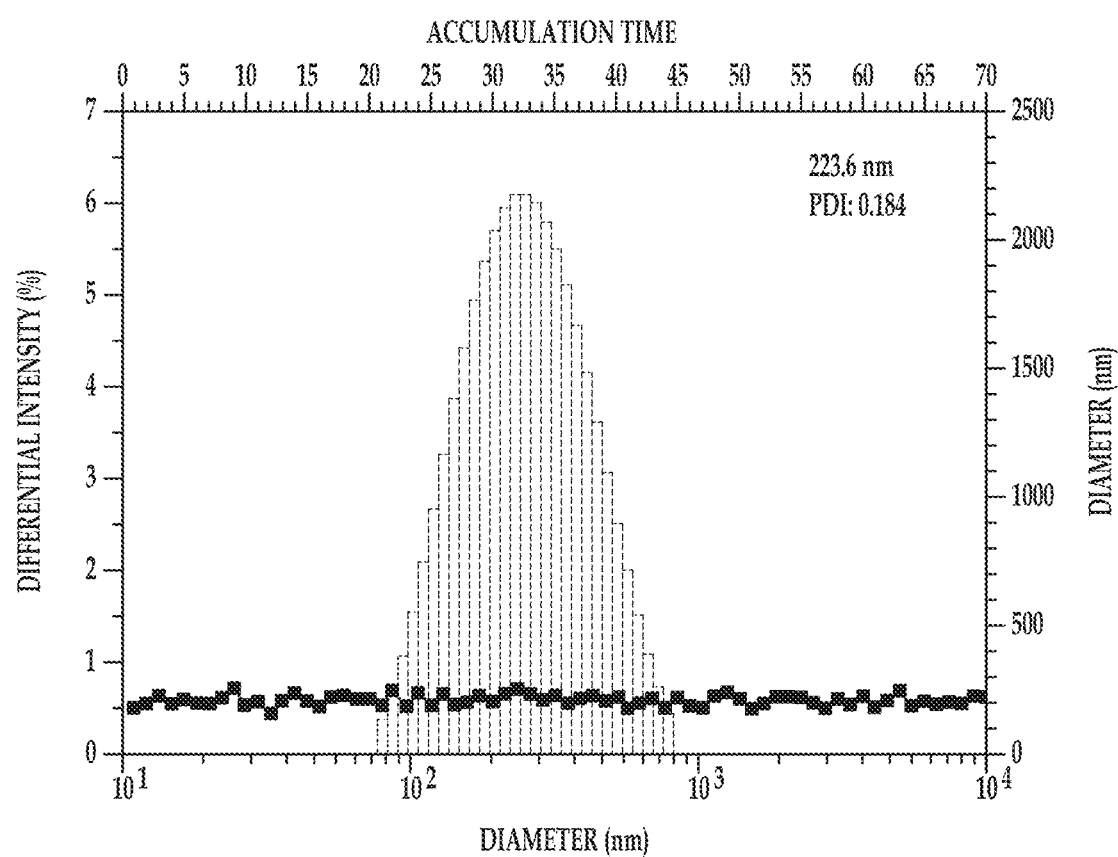
FIGS. 11A and 11B are size distribution profiles determined by dynamic light scattering (DLS) for HP3/miRNA polyplexes before sonication (11A) and after sonication (11B)
Figure 11B:
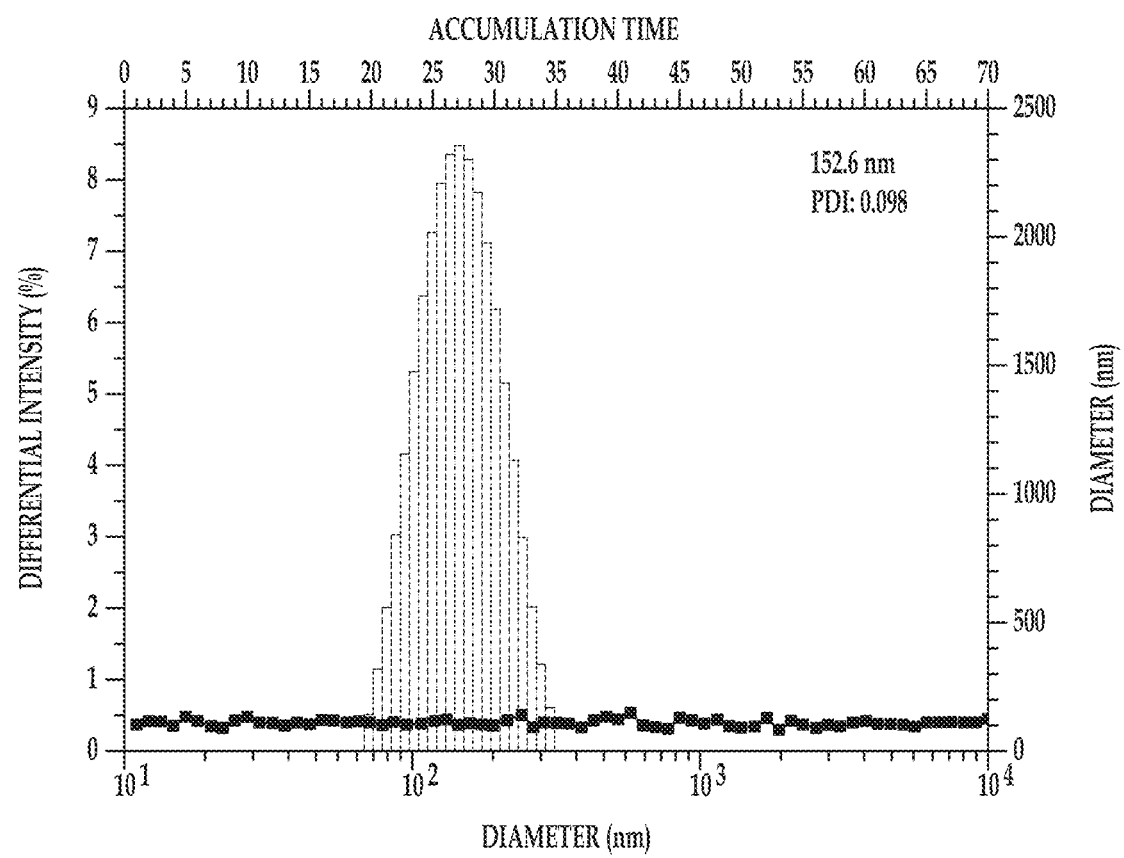
Figure 11C:
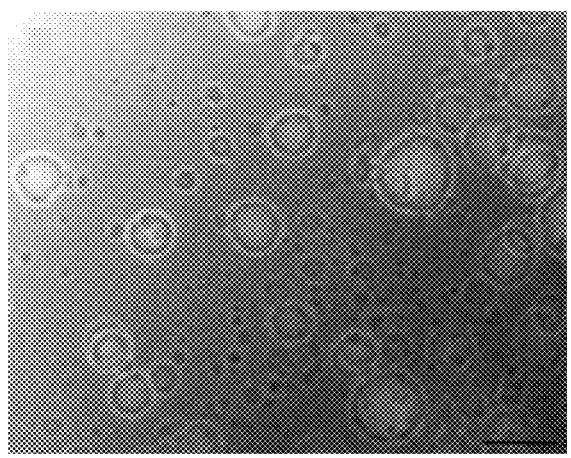
FIGS. 11C and 11D are morphology images of the HP3/miRNA polyplexes before sonication (11C) and after sonication (11D), as characterized by TEM (scale bar, 100 nm)
Figure 11D:
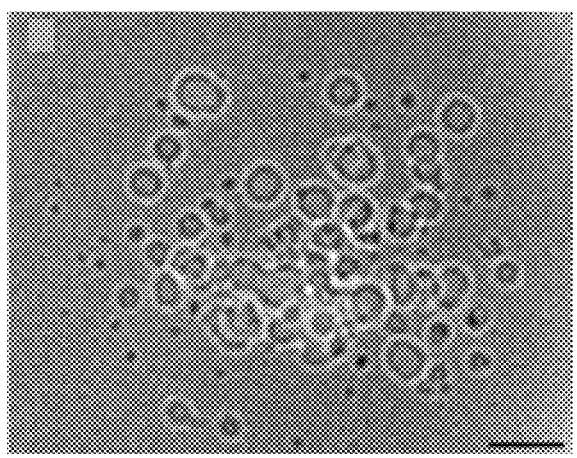

In FIGS. 11A and 11B, respectively, the size distribution profiles determined by DLS for HP/miRNA polyplexes are shown before sonication and after sonication. Morphology images (characterized by TEM (scale bar, 100 nm)) of the HP/miRNA polyplexes before sonication are shown in FIG. 11C, and after sonication are shown in FIG. 11D. In contrast to the lipoplexes, the size of the HP3/miRNA polyplexes and the PDI had little discernible change under sonication, which indicated that the HP3/miRNA polyplexes were very stable. More particularly, HP/miRNA polyplexes were smaller in size with an initial average diameter of about 224 nm and were stable under sonication, resulting in a narrower size distribution and a slightly reduced average size to 152 nm under sonication likely due to mechanically-induced denser packing.

The HP/miRNA polyplexes and LP/miRNA polyplexes were also compared. In particular, the particle size and zeta potential of the polyplexes were measured by dynamic light scattering (DLS) on a Beckman Coulter DelsaNano C Submicron Particle Size Analyzer at room temperature. As described above, the polyplexes at N/P ratios of 10 were prepared by adding appropriate volume of RNA solution to appropriate volume of polymer solution (1.0 mg/mL) and incubated at room temperature for 30 minutes. For these measurements, the polyplexes were then diluted with RNase-free water to 1.0 mL volume prior to measure. High molecular weight PEI 25 kDa and low molecular weight PEI 800 Da were also tested.

Figure 12A:
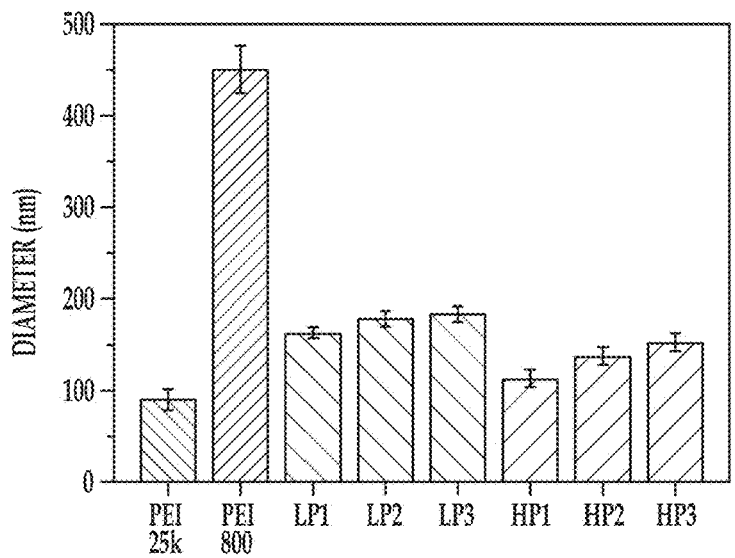
FIGS. 12A and 12B are graphs depicting the particle size (12A) and zeta potential (12B), as measured by DLS, of a high molecular weight polyethyleneimine (PEI), a low molecular weight PEI, and several examples of the linear polymer/RNA polyplexes and hyperbranched polymer/RNA polyplexes at N/P ratios of 10 (N nitrogen atoms of the polymer over P phosphates of RNA)

The particle size results are shown in FIG. 12A. The particle size results indicated that the diameters of the HP/miRNA polyplexes were smaller than those of linear polymer/miRNA polyplexes (when the ratios of PEG/polyesters were kept the same in the respective polymers). This may be due to the highly concentrated dendritic structure and the shorter PEG chain of HPs.

Figure 12B:
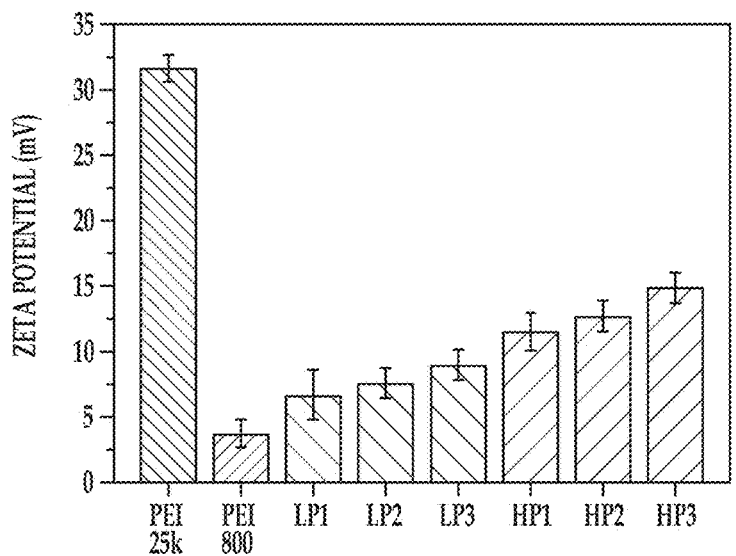

The Zeta potential results are shown in FIG. 12B. The Zeta potentials of HP/miRNA and LP/miRNA polyplexes were higher than the low PEI (PEI 800 Da), but lower than the high molecular weight PEI (PEI 25 kDa), increasing with increasing polyester molecular weight and degree of branching.

Together, the results in FIGS. 12A and 12B show that PEI 25 kDa could form about 100 nm of stable nanoparticles with RNA at high potential and PEI 800 had a large size at low potential. The diameters and zeta potential of linear or hyperbranched polymers/RNA polyplexes were in between those of PEI 25 kDa and PEI 800 Da.

Preparation of PLGA Microspheres (MS) Containing Polymer/miRNA Polyplex and MS-Incorporated PLLA Nano-Fibrous Scaffold (MS-Scaffold)

PLGA (poly(lactide-co-glycolide)) microspheres (MS) containing LP (LP1, LP2. Or LP3) or HP (HP1, HP2, HP3)

polymer/miRNA polyplexes were fabricated using a modified water-in-oil-in-water (w/o/w) double emulsion method. Briefly, 30 mg of PLGA was dissolved in 1 mL of dichloromethane. 100 µL aqueous solution of polymer/miRNA polyplex with an N/P of 10 containing 1.8 nmol of fluorescence miRNA was added into the above solution and emulsified with a probe sonicator at 50 W (Virsonic 100, Gardiner, N.Y.). This primary w/o emulsion was then emulsified into 10 mL of PVA solution (1% wt/vol) under sonication at 90 W to form the w/o/w emulsion. The resulting secondary emulsion was magnetically stirred at room temperature for about 12 hours to evaporate the solvents. The PLGA microspheres were collected by centrifugation and washed three times with water and freeze dried.

For comparison, PLGA microspheres with non-fluorescent miRNA polyplexes, PLGA microspheres containing fluorescence miRNA (i.e., naked), PLGA microspheres containing fluorescence argomir miRNA, and PLGA microspheres containing lipofectamine/miRNA lipoplexes were prepared in a similar manner to the PLGA microspheres containing LP or HP polymer/miRNA polyplexes.

It was noted that after centrifugation, the PLGA microspheres with non-fluorescent miRNA polyplexes formed a very clear solution. The fluorescence miRNA (i.e., naked) and the fluorescence argomir miRNA were entrapped into the PLGA microspheres with a low efficiency, as evidenced by a very light red color in the respective precipitates after centrifugation. In contrast, the HP3/miRNA polyplexes were entrapped into the PLGA microspheres with a high efficiency, as evidenced by a very strong red color in the precipitate after centrifugation.

Figure 13:
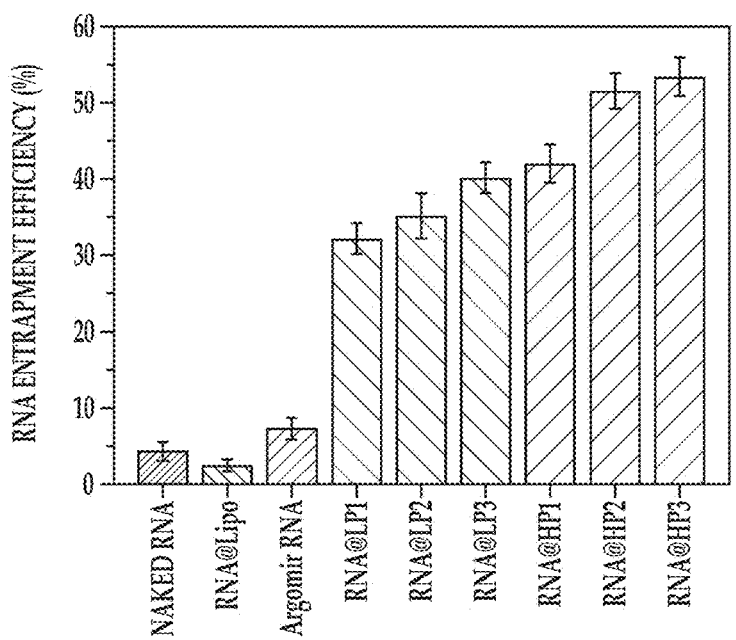
FIG. 13 is a graph depicting the RNA entrapment efficiency of PLGA microspheres with naked miRNA, lipofectamine/miRNA lipoplexes, argomir miRNA, linear polymer/miRNA polyplexes, and hyperbranched polymers/miRNA polyplexes.

The miRNA loading content and encapsulation efficiency were determined by UV spectrophotometric analysis. First, 1.0 mg of the respective PLGA microspheres was dissolved in 1.0 mL of dichloromethane. Then, 0.5 mL of RNase-free water was added to extract miRNA. The extraction process was repeated several times. The miRNA concentration was measured using a ThermoElectron 3001 Varioskan Flash Spectral Scanning Microplate Reader. The RNA entrapment efficiency of the comparative and example PLGA microspheres is shown in FIG. 13. In particular, FIG. 13 shows the RNA entrapment efficiency of naked miRNA, lipofectamine/miRNA lipoplexes, argomir miRNA, linear and hyperbranched polymers/miRNA polyplexes into the PLGA microspheres. The efficiencies of naked miRNA, lipofectamine/miRNA lipoplexes, and argomir miRNA were very low (<10%). In contrast, the linear polymer/miRNA polyplexes and the hyperbranched polymer/miRNA polyplexes had high RNA entrapment efficiencies. Furthermore, the efficiencies of miRNA polyplexes with hyperbranched polymers (especially HP2 and HP3) were substantially higher than those with linear polymers.

PLLA (poly(L-lactic acid)) nano-fibrous scaffolds with dimensions of 5 mm in diameter and 2 mm in thickness were prefabricated by a combination of phase separation and sugar leaching techniques. The PLGA MS were incorporated onto PLLA NF-scaffolds using a post seeding method. Briefly, PLGA MS were dispersed in hexane with 0.1% span 80 and were seeded onto NF-scaffolds dropwise. Then, the scaffolds were subject to vapor of a mixed solvent of hexane/THF (9:1 by volume) for 30 minutes. The scaffolds were dried under vacuum for 3 days to remove the solvents.

The morphology and size of the scaffolds before and after MS incorporation were characterized by scanning electron microscopy (Philips XL30 FEG SEM). The scaffolds were coated with gold using a sputter coater (DeskII, Denton vacuum Inc). During the process of gold coating, the gas pressure was 50 mtorr, and the current was 40 mA. The coating time was 120 seconds. Samples were analyzed at 15 kV.

Figure 14A:
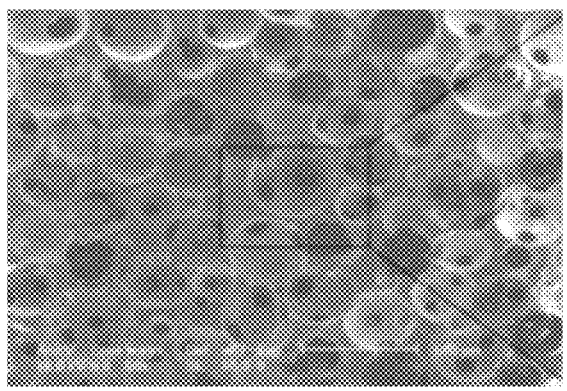
FIGS. 14A through 14D are scanning electron microscope (SEM) images of poly(L-lactic acid) (PLLA) scaffolds attaching examples of the PLGA microspheres having embedded therein the HP3/miRNA polyplexes, the black outlines identify the enhanced portion shown in the subsequent figure.
Figure 14B:
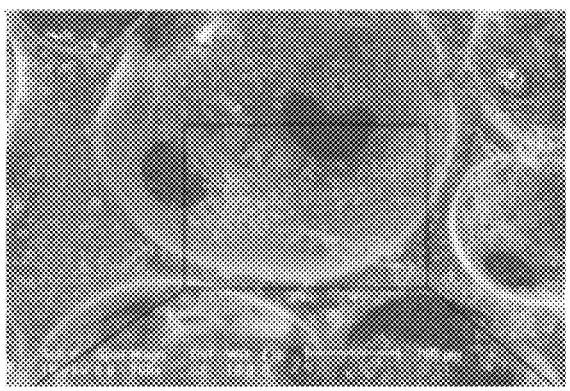
Figure 14C:
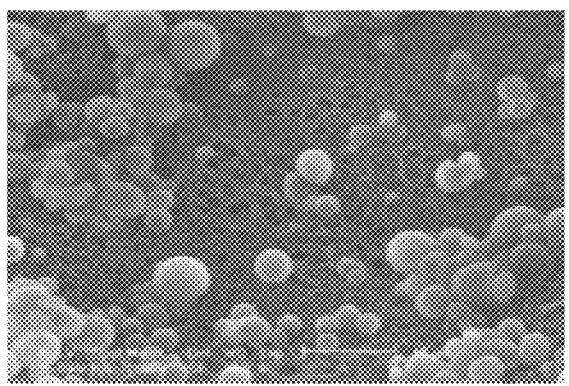
Figure 14D:
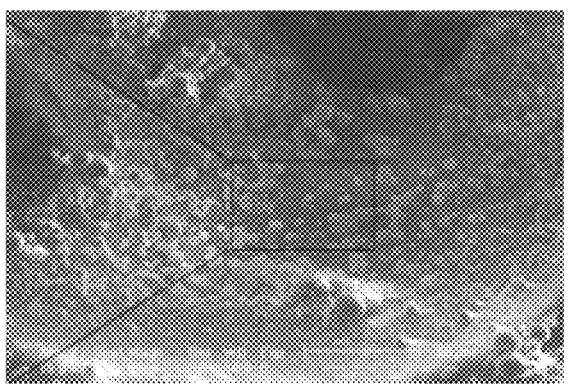

The SEM images of the PLLA nano-fibrous scaffold attaching the PLGA microspheres containing the HP3/miRNA polyplexes are shown in FIGS. 14A through 14D, where FIG. 14B is a higher magnified image of the portion outlined in FIG. 14A, FIG. 14C is a higher magnified image of the portion outlined in FIG. 14B, and FIG. 14D is a higher magnified image of the portion outlined in FIG. 14C. The diameter of PLLA nano-fibrous scaffold was 5 mm and the pore sizes ranged from about 250 µm to about 425 µm. The PLGA microspheres were around 3 µm. The PLGA microspheres were dispersed on the surface(s) and in the pores of the PLLA scaffold.

The SEM images showed that the interconnectivity between pores in the scaffold, which is advantageous for cell seeding or migration, and the nanofibrous morphology, which is advantageous for tissue regeneration, were retained after the PLGA MS immobilization procedure. Furthermore, these images confirmed that the PLGA MS were well distributed throughout the scaffolds.

In Vitro miRNA Release

The release profiles of HP3/miRNA polyplex-loaded PLGA MS-scaffolds were investigated in PBS (pH 7.4, 0.1 M). The scaffolds were placed in 0.2 mL of PBS and shaken at 50 rpm at 37° C. At predetermined time intervals, the release medium was withdrawn and replaced with prewarmed fresh PBS. The released amounts of miRNA from the microspheres on the scaffolds were analyzed using a ThermoElectron 3001 Varioskan Flash Spectral Scanning Microplate Reader.

Figure 15:
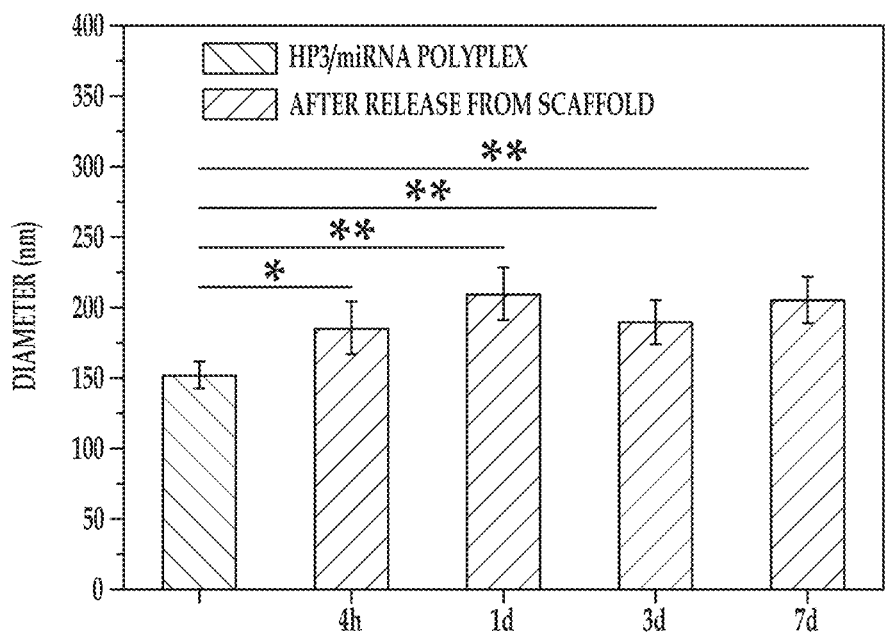
FIG. 15 is a graph depicting the diameters of HP3/miRNA polyplexes before and after release from the PLLA scaffold and the PLGA microspheres, *P<0.05 and **P<0.01.

The diameters of the HP3/miRNA polyplexes before and after release from the scaffold are shown in FIG. 15. After release, the HP3/miRNA polyplexes maintained the nanoparticle shape, and had little discernible change about the diameter. It was found that the released HP3/miRNA polyplexes had average diameter of about 200 nm, which was larger than those of the originally incorporated polyplexes (152 nm). These results indicated that the polyplexes were quite stable even when entrapped into the PLGA microspheres and released therefrom.

Figure 16:
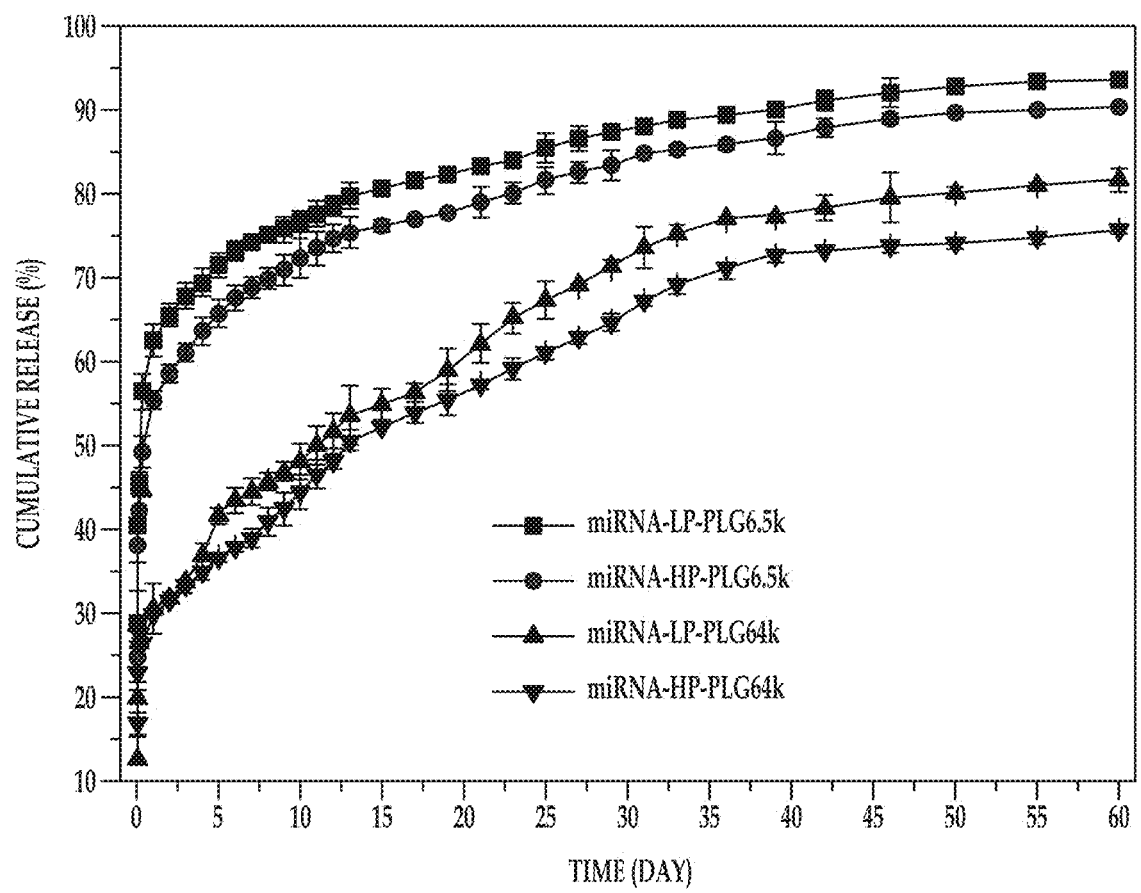
FIG. 16 is a graph depicting the release profile of miRNA from PLGA 6.5 k or 64 k microspheres containing the LP3/miRNA polyplexes or the HP3/miRNA polyplexes.

The release profiles of LP3/miRNA polyplex-loaded PLGA microspheres and HP3/miRNA polyplex-loaded PLGA microspheres were investigated with different molecular weight PLGAs, namely 6.5 k PLGA and 64 k PLGA. The release profiles were investigated in PBS (pH 7.4, 0.1 M, 37° C.) as described above. The results are shown in FIG. 16. As depicted, the MS made of PLGA with a molecular weight of 6.5 k achieved a shorter-term release, while the MS made of PLGA with a molecular weight of 64 k achieved a longer-term release. There was about a 60% burst release of either LP/miRNA or HP/miRNA polyplexes from the PLGA 6.5 k MS during the first day, followed by a sustained release of the polyplexes at a substantial level for approximately 2 weeks. In contrast, there was about a 25%-30% burst release of either LP/miRNA or HP/miRNA polyplexes from the PLGA 64 k MS during the first day, followed by a sustained release of the polyplexes for longer than one month.

In Vitro and/or In Vivo Cellular Uptake and miRNA Expression

For cellular uptake and miRNA expression analysis of the miRNA/polymer complexes and lipofectamine 2000/miRNA lipoplexes in vitro, the respective components were first labeled following standard protocols. miRNA and agomir were labeled by Cy3 (orange red), the polymers (vectors) were labeled by FITC (green), and cell (osteoblast) nucleus were stained with DAPI (blue). As an example, FITC (2.0 mg) and polymer (16.0 mg) in methanol (2 mL) were stirred overnight at room temperature. The solution was then transferred into a dialysis bag (MWCO 3500 Da) and dialyzed against a continuous flow of deionized water for 2 days, during which the water was renewed each 8 hours. The product was obtained by lyophilization to give a flocculent solid FITC-polymer. Osteoblasts were similarly stained with DAPI to show their nuclei. In order to label the lipofectamine 2000, NBD cholesterol (10% by weight) was added into the lipoplex solution.

The in vitro transfection efficiency of the polyplexes and lipoplexes was evaluated in the osteoblasts. The stained osteoblasts were seeded at a density of 4000 cells/well into 8 chambered coverglass (Nunc, USA) and incubated at 37° C. in a humidified atmosphere of 95% air and 5% $CO_2$ until the cells reached about 70% confluence. At the time of transfection, the medium in each well was replaced with 400 μL fresh DMEM medium. The FITC-labeled polymer or NBD cholesterol labeled liposome was combined with Cy3-labeled miRNA to form the polyplexes or lipoplexes (in the same manner previously described), and were then added and incubated with the cells at 37° C. The negative control was scrambled miRNA without biological activity.

Figure 17A:
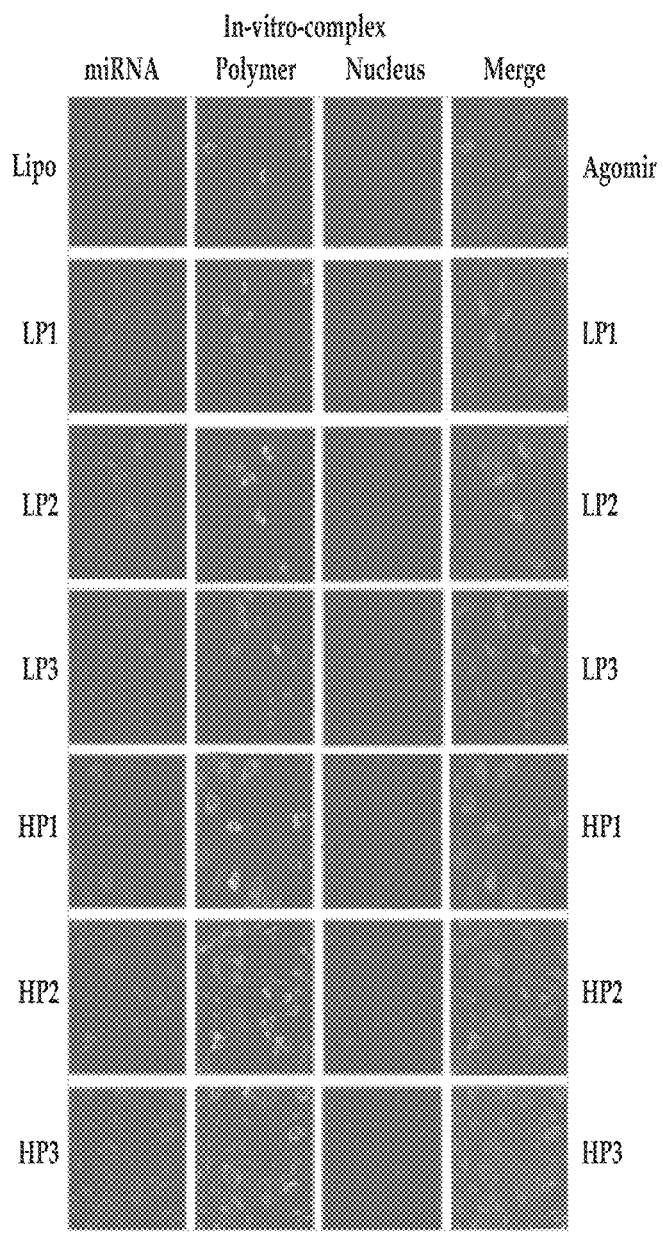
FIGS. 17A, 17B, and 17C illustrate black and white confocal laser scanning microscopy images (17A), the quantified fluorescence intensity (17B), and the miRNA expression level (17C) of cell and polyplex complexes and cell and lipoplex complexes in vitro.
Figure 17B:
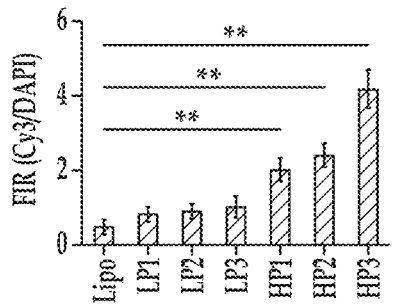
Figure 17C:
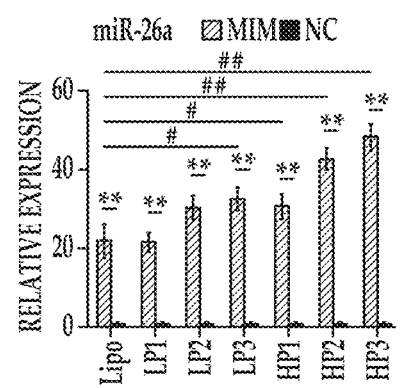

At 48 hours post-transfection, the cells were observed using confocal laser scanning microscopy (Nikon C1-si TE2000, Japan) (shown in black and white in FIG. 17A) and RNA were extracted for further real time RT-PCR test. The efficiency of bio-functional transfection of the polyplexes and lipoplexes in vitro was determined by quantifying the fluorescence intensity (FIG. 17B) and the miRNA expression level (FIG. 17C). In order to quantify the amount of polyplex or lipoplex into the cells, FITC/NBD/miRNA-derived fluorescence was captured and analyzed by Image-pro plus 6.0 image analysis software to measure the intensity of the FITC/NBD/miRNA-derived fluorescence in cells comparing with the area expressing DAPI-derived fluorescence in nuclei. These results are shown in FIG. 17B. The HPs had much higher transfection efficiency than LPs or lipofectamine 2000, as evidenced by the greatest amounts of miRNA polyplexes found inside the cells using confocal microscopy observation (FIG. 17A) and higher levels of the miRNA expression quantified using real time PCR (FIG. 17C). In these Figures, MIM refers to the miRNA-26a mimic and the NC refers to the negative control for mi-RNA-26a.

The labeled polyplexes and lipoplexes were incorporated into PLGA microspheres as previously described, and the embedded PLGA microspheres were immobilized on PLLA nanofibrous scaffolds as previously described. The scaffolds were placed in 0.2 mL of PBS and shaken at 50 rpm at 37° C. After 2 days, the release medium was collected and co-cultured with the osteoblasts under the conditions described above.

Figure 18A:
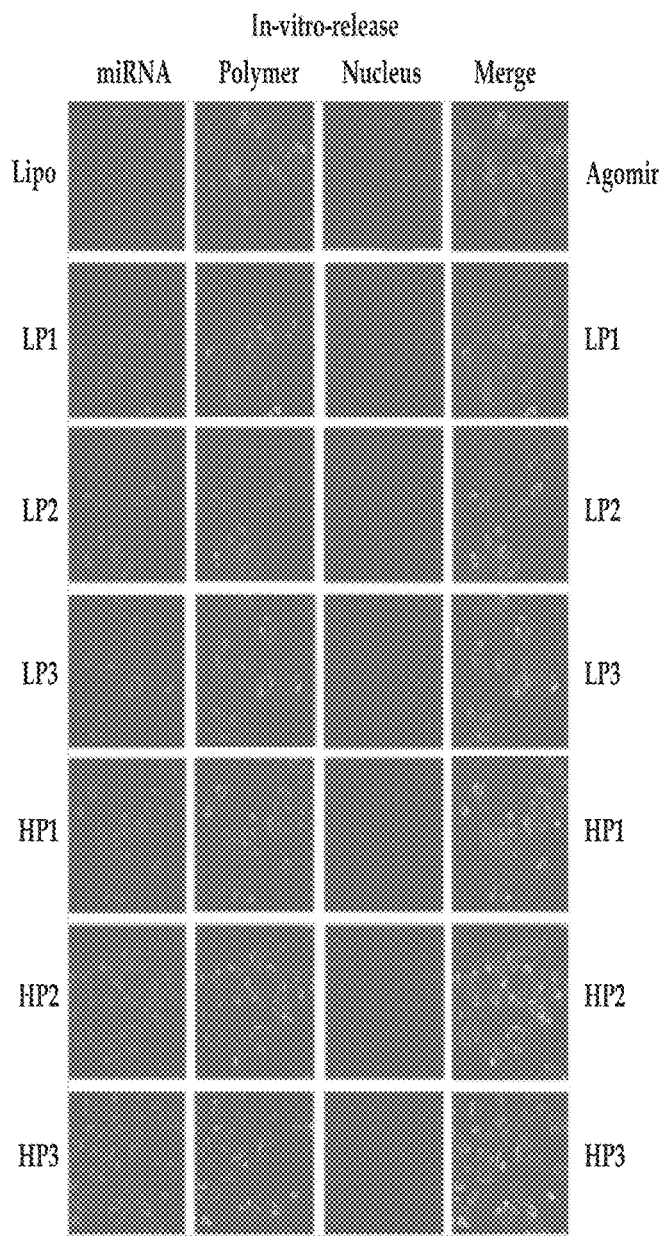
FIGS. 18A, 18B, and 18C illustrate black and white confocal laser scanning microscopy images (18A), the quantified fluorescence intensity (18B), and the miRNA expression level (18C) of the release media including cell and polyplex complexes and cell and lipoplex complexes released from PLGA microspheres in vitro.
Figure 18B:
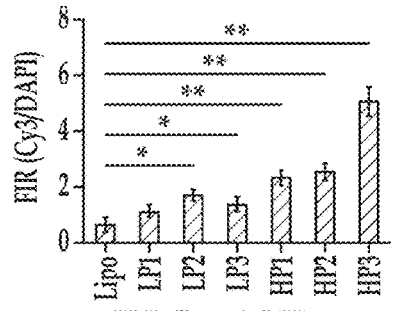
Figure 18C:
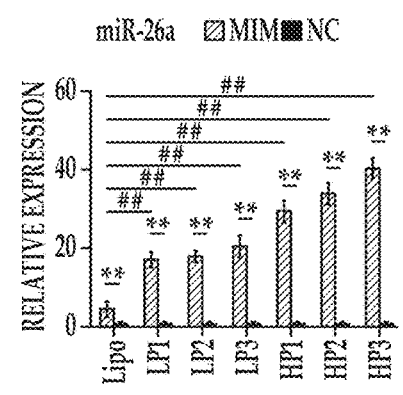

At 48 hours post-transfection, the cells were observed using confocal laser scanning microscopy (Nikon C1-si TE2000, Japan) (shown in black and white in FIG. 18A) and RNA were extracted for further real time RT-PCR test. The efficiency of bio-functional transfection of the released polyplexes and lipoplexes in vitro was determined by quantifying the fluorescence intensity as described above (results shown in FIG. 18B) and the miRNA expression level (results shown in FIG. 18C). The confocal images (FIG. 18A), the fluorescence intensity quantification (FIG. 18B), and the miRNA expression quantified using real time PCR (FIG. 18C) showed that HP/miRNA polyplex had higher transfection efficiency and resulted in higher miRNA expression in cells than LP/miRNA polyplex and lipofectamine 2000.

For cellular uptake and miRNA expression analysis of Cy3-labeled polyplexes or Cy3-labeled agomir in vivo, the PLLA scaffolds having immobilized thereon PLGA microspheres containing FITC-labeled polyplex or Cy3-labeled agomir were implanted into subcutaneous pockets of nude mice. At 2 weeks post-surgery, the implants were harvested for fluorescent images observed and RNA extraction.

Figure 19A:
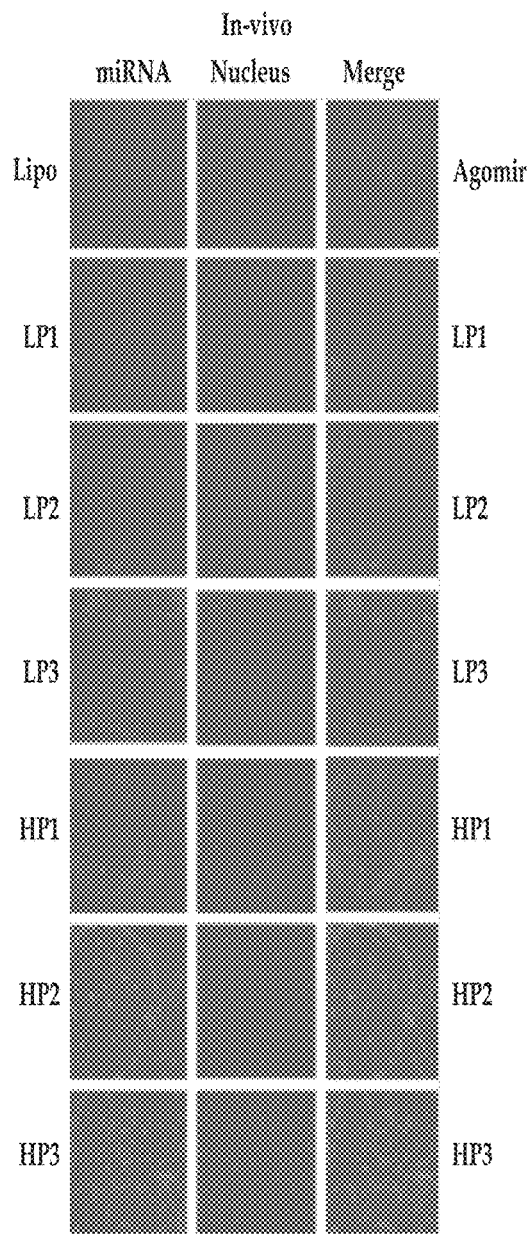
FIGS. 19A, 19B, and 19C illustrate black and white confocal laser scanning microscopy images (19A), the quantified fluorescence intensity (19B), and the miRNA expression level (19C) of cell and polyplex complexes and cell and lipoplex complexes tested in vivo.
Figure 19B:
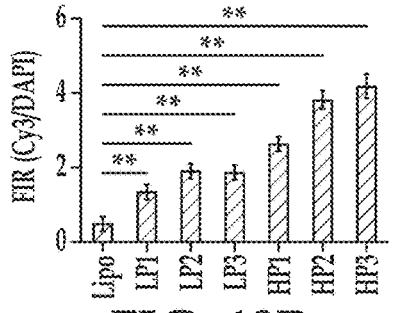
Figure 19C:
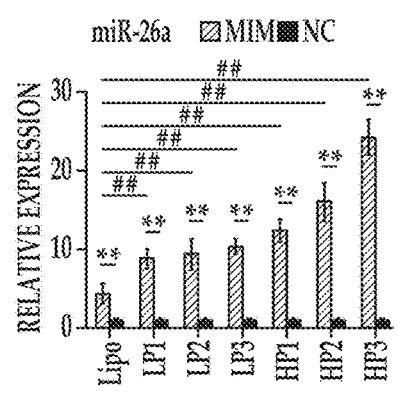

The extracted cells were observed using confocal laser scanning microscopy (Nikon C1-si TE2000, Japan) (shown in black and white in FIG. 19A) and RNA were extracted for further real time RT-PCR test. The efficiency of bio-functional transfection of the released polyplexes and lipoplexes in vivo was determined by quantifying the fluorescence intensity as described above (results shown in FIG. 19B) and the miRNA expression level (results shown in FIG. 19C). The confocal images (FIG. 19A), the fluorescence intensity quantification (FIG. 19B), and the miRNA expression quantified using real time PCR (FIG. 19C) showed that HP/miRNA polyplex had higher transfection efficiency and resulted in higher miRNA expression in cells than LP/miRNA polyplex and lipofectamine 2000.

Calvarial Bone Defect Model Construction

C57BL/6J mice were divided into three groups randomly. The animals were anesthetized with 2% inhalation of isofluorane. A linear scalp incision was made from the nasal bone to the occiput, and full-thickness flaps were elevated. The periosteum overlying the calvarial bone was completely resected. A trephine was used to create a 5-mm craniotomy defect centered on the parietal calvarial bone, and the wounds were copiously irrigated with Hanks' balanced salt solution while drilling. The calvarial disk was removed carefully to avoid injury to the underlying dura or brain.

After careful hemostasis, cell-free miRNA continuous delivery systems were placed into the defects. These delivery systems included PLLA scaffolds with non-embedded HP/miRNA polyplexes immobilized thereon, as well as PLLA scaffolds with HP/miRNA polyplex-embedded PLGA microspheres immobilized thereon. PLGA 6.5 k was used for short-term release, and PLGA 64 k was used for long-term release. The scaffolds filled the entire defect.

The incisions were closed with 4-0 Braided Absorbable Suture (Covidien, USA), and the mice recovered from anesthesia on a heating pad. All mice were sacrificed and calvaria were harvested at 8 weeks after the implantation.

MicroCT Analysis and Bone Histological Analysis

For the proximal tibia analysis using microCT, specimens were embedded in 1% agarose and placed in a 19 mm tube and scanned over the entire length of the tibia using a micro CT system (μCT100 Scanco Medical, Basserdorf, Switzerland). Scan settings were: voxel size 15 mm, 70 kVp, 114 mA, 0.5 mm AL filter, and integration time 500 ms. MicroCT analysis was performed using the manufacturer's evaluation software and a fixed global threshold of 28% (280 on a grayscale of 0-1000) for cortical bone and 18% for trabecular bone was used to segment bone from non-bone. A 0.75 mm region of trabecular bone was analyzed immediately below the growth plate, and a 0.5 mm cortical region was analyzed located 3 mm proximal of the tibiofibular joint. For the calvarial bone analysis, the region of the parietal calvarial bone was scanned with a fixed global threshold of 20% (200 on a grayscale of 0-1000). All the trabecular bone from each selected slice was segmented for three-dimension reconstruction to calculate the following parameters: bone mineral density (BMD, FIG. 20E), and relative bone volume (Bone volume/Total area, FIG. 20D).

For calvarial bone defect repair detection using microCT (Siemens AG, Germany), the specimens were fitted in a cylindrical sample holder with the coronal aspect of the calvarial bone in a horizontal position. Specimens were scanned with the scanning direction parallel to the coronal aspect of the calvarial bone at a fixed isotopic voxel size of 12 mm to cover the entire thickness of the calvarial bone. Analysis was performed using the manufacturer's evaluation software and a fixed global threshold of 25% (250 on a grayscale of 0-1000). A 5 mm round region of interest for analysis centered around the epicenter of the defect. On three-dimensional images of the specimen, bone volume (mm3) and BMD in the defect site were measured directly.

For bone histological analysis, the specimens (from subcutaneous implant and calvarial bone defect repair model) were fixed with 4% formalin, decalcified with 10% EDTA and subsequently embedded in paraffin. Coronal sections (6 μm thick) were stained with hematoxylin and eosin (H&E). For immunofluorescence analysis of OCN (osteocalcin) expression in new formed tissue in the defect area, the slides were de paraffinized, and then cooked in citrate buffer (2.1 M citric acid, pH 6.0) at 120° C. for 30 minutes for antigen retrieval. After blocked in serum, the sections were incubated overnight at 4° C. with rabbit polyclonal primary antibodies to OCN (1:100, Abcam). After three washes in PBS, the sections were incubated with FITC-conjugated donkey antibody to rabbit IgG (1:400, Santa Cruz) for 1 hour. Negative control experiments were performed by omitting the primary antibodies. The sections were mounted with the medium containing DAPI (Vector Laboratories) and then examined under a confocal microscope (Eclipse C1 Plus, Nikon, Japan).

The results of the microCT analysis and bone histological analysis indicate that the scaffolds disclosed herein significantly improved critical-sized calvarial bone defect repair through sustaining the osteogenic key factors expression at high levels for prolonged time periods.

Figure 20A:
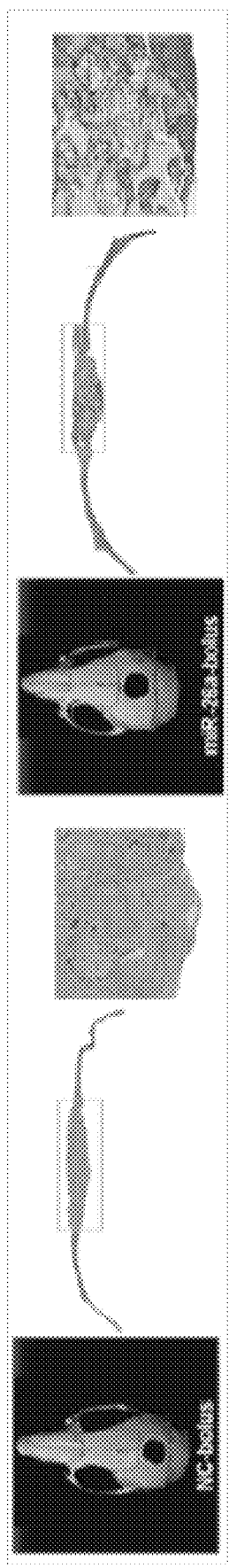
FIG. 20A through 20C are black and white microCT images and H&E staining images of cell-free PLLA scaffolds with directly attached HP3/miR-26a or negative control polyplexes (20A), cell-free PLLA scaffolds with attached HP3/miR-26a or negative control polyplexes loaded into PLGA 6.5 k microspheres (20B), and cell-free PLLA scaffolds with attached HP3/miR-26a or negative control polyplexes loaded into PLGA 64 k microspheres (20C)

FIG. 20A illustrates (in black and white) the microCT images and the H&E stained images at low magnification and high magnification of the PLLA scaffolds with non-embedded HP/miRNA polyplexes. Both the HP/miRNA polyplexes (labeled and referred to as "miR-26a-bolus") and the negative control polyplexes (labeled and referred to as "NC-bolus") results are shown.

Figure 20B:
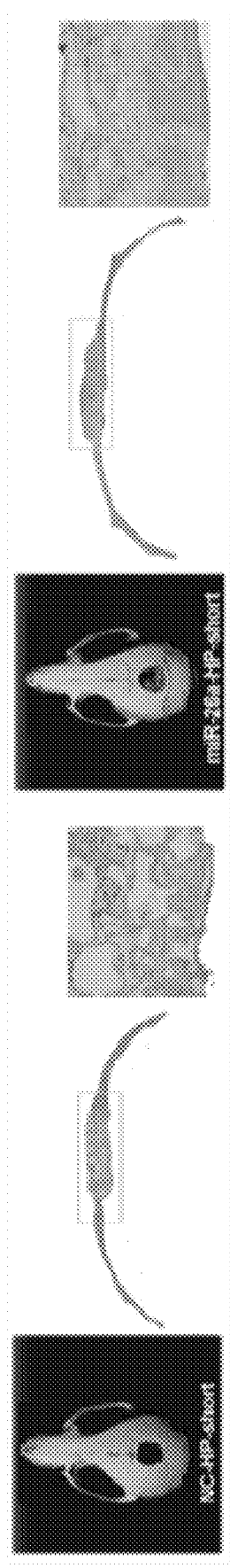

FIG. 20B illustrates (in black and white) the microCT images and the H&E stained images low magnification and high magnification of the PLLA scaffolds with HP/miRNA polyplex-embedded PLGA 6.5 k microspheres. Both the HP/miRNA polyplex-embedded PLGA 6.5 k microspheres (labeled and referred to as "miR-26a-HP-short") and the negative control polyplexes (labeled and referred to as "NC-HP-short") results are shown.

Figure 20C:
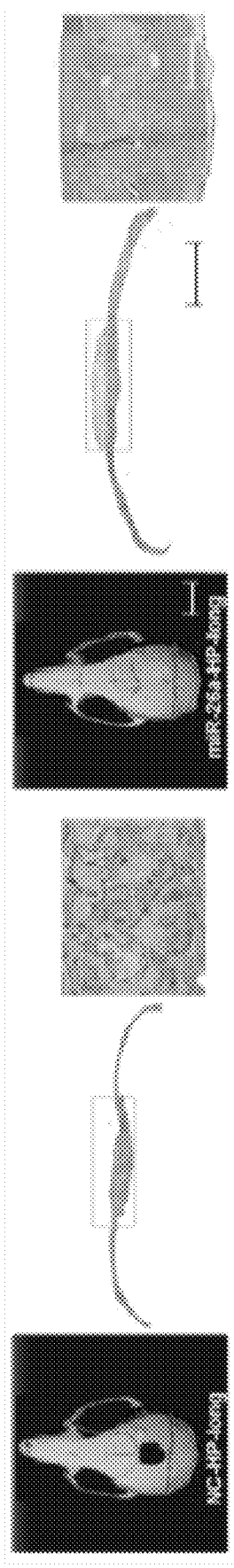

FIG. 20C illustrates (in black and white) the microCT images and the H&E stained images low magnification and high magnification of the PLLA scaffolds with HP/miRNA polyplex-embedded PLGA 64 k microspheres. Both the HP/miRNA polyplex-embedded PLGA 64 k microspheres (labeled and referred to as "miR-26a-HP-long") and the negative control polyplexes (labeled and referred to as "NC-HP-long") results are shown.

As noted above, FIGS. 20D and 20E are graphs depicting the relative bone volume (Bone volume/Total area) and bone mineral density (BMD, FIG. 20E) for each of the samples.

The microCT and HE stained histological images show that there were very small amounts of new bone formation in the calvarial defects in all NC delivery groups (FIGS. 20A-20E). The miR-26a bolus delivery improved new bone formation slightly, but not at a statistically significant level (FIGS. 20A, 20D, and 20E). The short-term sustained miR-26a delivery (i.e., miR-26a-HP-short) enhanced new bone formation at a statistically significant level (FIGS. 20B, 20D, and 20E). The long-term sustained miR-26a delivery (i.e., miR-26a-HP-long) resulted in complete repair of the defect (FIG. 20C) with dramatic bone volume increase (FIG. 20D).

The quantitative microCT analysis showed that consistent with significant neo bone volume increases, the bone mineral densities (BMD) of the short-term and long-term sustained miR-26a release groups were also increased (FIG. 20E).

RNA Extraction and Real Time (RT)-PCR for Example 1

RNA extraction and real time PCR was performed several times throughout Example 1. In each instance, the total miRNA from the collected cells was extracted using the miRNeasy Mini Kit (Qiagen, USA). Briefly, the cells were collected in a reaction tube, lysed with 700 μL QIAzol and mixed with 140 μL chloroform. After being centrifuged at 12,000 g for 15 minutes at 4° C., the upper aqueous phase was transferred to an RNeasy Mini spin column in a 2-mL collection tube and mixed with 100% ethanol. After being washed with 700 μL Buffer RWT and 500 μL Buffer RPE, the total miRNA was collected for real-time PCR analysis.

Complementary DNAs (cDNAs) were synthesized using a Geneamp PCR (Applied Biosystems) with TaqMan reverse transcription reagents and 10 minute incubation at 25° C., 30 minute reverse transcription at 48° C., and 5 minutes inactivation at 95° C. One microliter of cDNA was PCR amplified using Platinum Taq DNA Polymerase (Invitrogen). Two microliters of a 1:10 dilution of the synthesized cDNA were used for real-time PCR.

Statistical Analyses in Example 1

All numerical data in Example 1 were presented as means+s.d. All statistical analyses were performed with SPSS 13.0. Statistical differences among groups were analyzed by one-way ANOVA. Statistical differences between two groups were determined by the Student's t test. $P<0.05$ was considered statistically significant.

Example 2

HP and LP Affinity to DNA

Respective hyperbranched and linear polymer solutions (1.0 mg/mL) from Example 1 were added slowly to a DNA solution containing 1 μg of DNA (pUC18 DNA, Thermo Scientific). The amount of added polymer solution was calculated based on a chosen N/P ratio of the polymer/DNA mixture (N/P=nitrogen atom number of the polymer over phosphate atom number of the DNA). The mixture was incubated at room temperature for 30 minutes for polyplex formation.

A 10 μL sample of the polyplex solution mixed with 4 μL of 1× loading buffer was loaded to agarose gel. The polyplexes were electrophoresed on a 0.7% agarose gel containing GelRed with Tris-acetate (TAE) running buffer (pH 8) at 80 V for 45 minutes. DNA bands were visualized using an UV (254 nm) illuminator and photographed with a BioSpectrum Imaging System (USA). The results are shown in FIG. 21.

The binding affinity of the hyperbranched and linear polymers to the DNA was examined using the above-described agarose gel electrophoresis assay. The results in FIG. 21 indicated that hyperbranched polymers were able to retard DNA migration at lower N/P ratios than the corresponding linear polymers. These results demonstrate that the hyperbranched polymers have higher affinity to DNA than the corresponding linear polymers, allowing highly efficient loading of DNA in the hyperbranched polymer/DNA polyplexes. These results also demonstrate that the polymers with higher molecular weights have higher affinity to the DNA than the polymers with lower molecular weights. These conclusions are in agreement with higher binding affinity and higher loading efficiency of the RNAs in the hyperbranched polymers than in the linear polymers.

Example 3

HP Delivery of microRNA-140 Enhances Chondrogenesis of Stem Cells and Prevents Endochondral Hypertrophy $P_3$ human BMSCs (ATCC) were cultured with α-MEM supplemented with 10% fetal bovine serum (FBS) in Φ 100 mm dishes. When the cells reached 90% confluence, they were transfected with microRNA-140. In particular, 13.7 μL of HP3 polymer (1 mg/mL) was mixed with 12.5 μL of 20 μM miR-140, and one hour later, the transfection mixture was added to the cell culture. One day later, the cells transfected with miR-140 and a mock control were trypsinized and seeded into porous NF PLLA scaffolds with the pore size ranging from 150 nm to 225 nm in diameter. The cell/scaffold constructs were cultured with chondrogenic medium (HG-DMEM supplemented with 1% FBS, 0.1 mM ascorbic acid, 1×ITS Premix, 0.1 μM Dex, and 10 ng/mL TGF-31) for another five weeks. Then, the constructs were fixed with 4% paraformaldehyde overnight, and the paraffin-sectioning was performed to get 7-μm sections.

Figure 22:
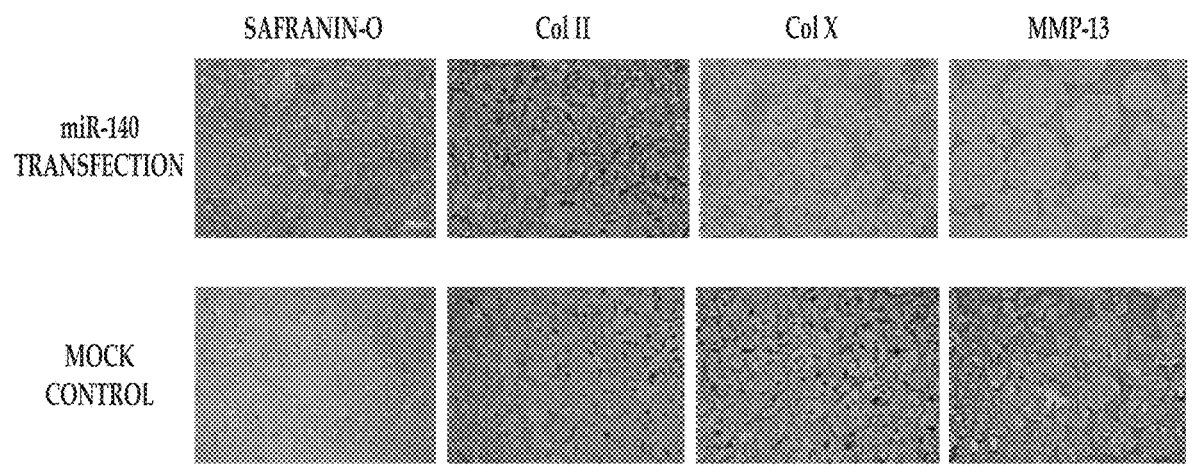
FIG. 22 are stained images, shown in black and white, of a mock control and cells transfected with miR-140 and seeded into porous NF PLLA scaffolds, where the cell/scaffold constructs were cultured with chondrogenic medium for five weeks.
Figure 23A:
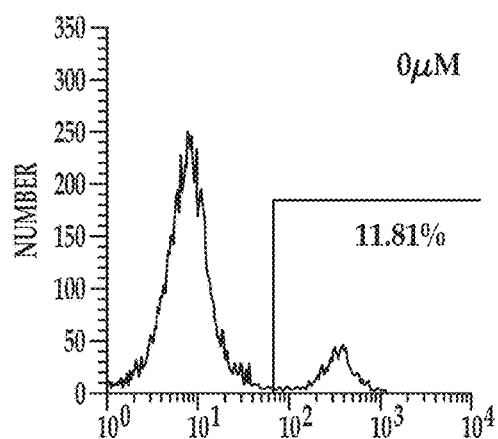
FIGS. 23A through 23D are graphs depicting the percentage of Foxp3$^+$ T cells as analyzed with flow cytometry, illustrating that miR-10a promoted the Tregs differentiation from 11.81±0.19% (23A) to 16.02±0.01% (23B), 15.96±0.21% (23C), and 15.74±0.21% (23D) in CD4$^+$ T cells at OpM (23A), 20 μM (23B), 40 μM (23C), and 80 μM (23D, respectively), where P<0.01.
Figure 23B:
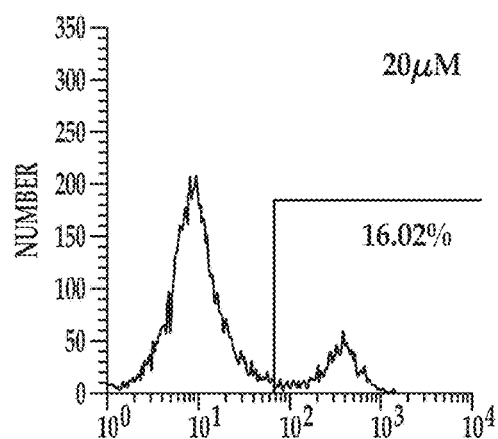
Figure 23C:
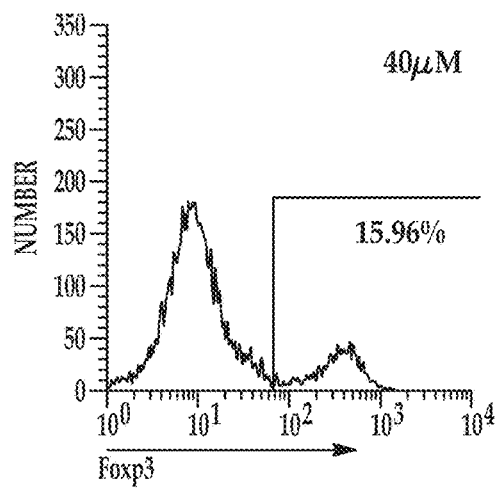
Figure 23D:
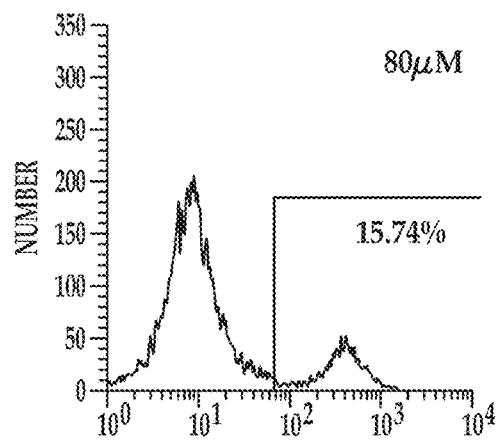

Safranin-O and fast-green, as well as immuno-histological (Col II, X and MMP-13) staining was carried out to appraise chondrogenesis and hypertrophic alteration. As shown in FIG. 22, compared with mock control, pre-transfection with miR-140 facilitated maintenance of cellular chondrogenesis (Safranin-O and fast-green, Col II), and prevented cellular hypertrophy to a certain extent. (Bar scale: 100 μm in FIG. 22).

Example 4 miR-10a Delivered by HP Polymer Enhances the In Vitro Differentiation of Foxp3+Regulatory T Cells in Mice Foxp3$^+$ regulatory T cells (Tregs) are a subpopulation of T cells that could mainly suppress immune reaction and inflammation caused by other immune cells. Tregs are considered to play an important role in the maintenance of immunological tolerance. Tregs can be differentiated from CD4$^+$ T cells with the induction of transforming growth factor-β (TGF-β) and interleukin-2 (IL-2). Enhancing the amount of Tregs may be a new method for treatment of autoimmune and inflammatory diseases. MicroRNAs (miRNAs) contribute to Tregs stability and function. miR-10a has been reported to express in Tregs but not in other T cells. In this example, it was hypothesized that miR-10a could enhance the differentiation of Tregs.

Figure 24:
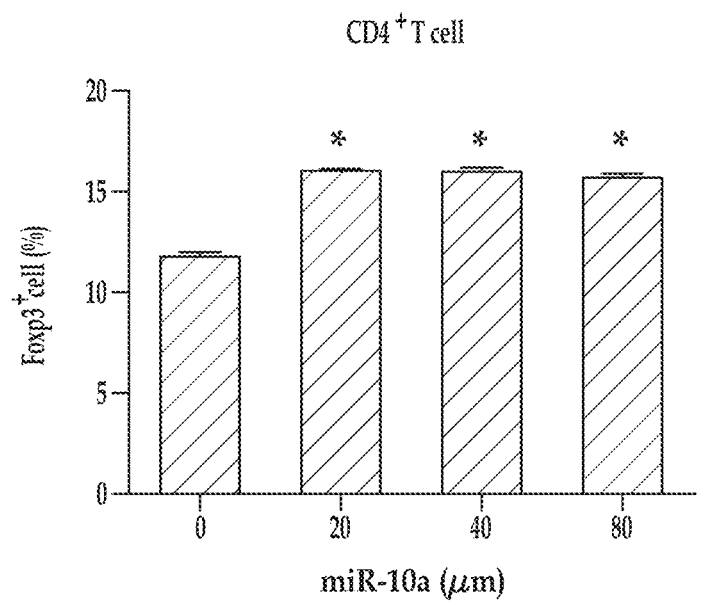
FIG. 24 is a graph illustrating the results of FIGS. 23A through 23D together.

For this in vitro study, CD4$^+$ T cells of mouse spleens were enriched with positive selection magnetic microbeads. The cells were cultured with RPMI 1640 medium containing 10% FBS in 96-well plates which contain plate-bound anti-CD3 and soluble anti-CD28 antibodies. For Tregs differentiation, 5 ng/ml TGF-β1 and 50 U/ml IL-2 were added in the medium.

miR-10a (20~80 μM) was incubated with HP3 polymer solution from Example 1 (1.0 mg/ml) for 30 minutes, and then the polyplex was used to transfect the CD4$^+$ T cells. After 4 days of induction, cells were collected and stained with 1 μg/ml Foxp3 antibody, and the percentage of Foxp3$^+$ T cells was analyzed with flow cytometry. The results showed that miR-10a promoted the Tregs differentiation from 11.81±0.19% (FIG. 23A) to 16.02±0.01% (FIG. 23B), 15.96±0.21% (FIG. 23C), and 15.74±0.21% (FIG. 23D) in CD4$^+$ T cells at 20 μM, 40 μM and 80 μM (P<0.01), respectively. These data suggest that miR-10a delivery using HP polymer with a dose of ≥20 μM improves the differentiation of regulatory T cells in vitro, reaching a level similar to existing drugs. The results of FIGS. 23A-23D are shown in the graph of FIG. 24. HP delivery of miR-10a is a potentially effective alternative for treating autoimmune and inflammatory diseases.

Example 5

Preparation of Polymer/NR4A1 Polyplexes

Hyperbranched polymers (HP) were formed in the same manner as described in Example 1. In this example, polyethyleneimine (PEI, Mw 800 Da), polyethylene glycol methyl ether (PEG, Mw 2000 Da), and hyperbranched bis-MPA polyester (H40: 64 hydroxyl) were used.

Designed H40 polymer solutions (1.0 mg/mL) were added slowly to DNA solutions containing 60 pmol of NR4A. The amount of polymer added was calculated on the basis of chosen N/P ratios of polymer/DNA (N nitrogen atoms of the polymer over P phosphates of DNA). The mixture was incubated at room temperature for 30 minutes for the polyplex formation.

The NR4A1 first complexed with the PEI on the outer shell of the hyperbranched polyester cores. The HP molecular cores and PEI/NR4A1 shells together assembled into the hydrophobic spherical shell sandwiched between the inner PEG core and the outer PEG chains of the 3-layer nanospheres.

Preparation of PLGA Nanospheres (NS) Containing Polymer/NR4AJ Polyplex and NS-Incorporated Nanofibrous Spongy Microsphere (NF-SMS)

PLGA (poly(lactide-co-glycolide), average molecular weight of 64,000) nanospheres (NS) containing the polymer/NR4A1 polyplex were fabricated using a modified water-in-oil-in-water (w/o/w) double emulsion method. Briefly, 30 mg of PLGA was dissolved in 1 mL of dichloromethane. 100 μL aqueous solution of polymer/NR4A1 polyplex with an N/P of 8 was added into the above solution and emulsified with a probe sonicator at 50 W (Virsonic 100, Gardiner, N.Y.). This primary w/o emulsion was then emulsified into 10 mL of PVA solution (1% wt/vol) under sonication at 90 W to form the w/o/w emulsion. The resulting secondary emulsion was magnetically stirred at room temperature for about 12 hours to evaporate the solvents. The PLGA NS (average diameter of 300 nm) were collected by centrifugation and washed three times with water and freeze dried.

While the data is not shown, the PLGA NS formed with the PLGA64 k exhibited sustained release of the polymer/NR4A1 polyplex for more than one month after a burst release on the first day.

Star-shaped poly(L-lactic acid)-co-polyHEMA (SS-PLLA-co-polyHEMA) was synthesized and assembled into nanofibrous spongy microspheres (NF-SMS) using emulsification and phase separation techniques. More specifically, the polymer (0.4 g) was dissolved in THF at 50° C. with a concentration of 2% w/v. Under rigorous mechanical stirring (Speed 9, Fisher Science Inc.), glycerol (50° C.) with three times the volume of star-shaped PLLA solution was gradually added into the polymer solution. After stirring for five minutes, the mixture was quickly poured into liquid nitrogen. After 10 minutes, a water-ice mixture (1 L) was added for solvent exchange for 24 hours. The microspheres were sieved and washed with distilled water eight times to remove residual glycerol on the sphere surfaces. The spheres were then lyophilized for three days.

The PLGA NS were immobilized on the NF-SMS using a post seeding method. Briefly, PLGA NS were dispersed in hexane with 0.1% span 80 and were seeded onto NF-SMS dropwise. Then, the NF-SMS were subject to vapor of a mixed solvent of hexane/THF (9:1 by volume) for 30 minutes. The NF-SMS were dried under vacuum for 3 days to remove the solvents.

The morphology and size of the PLGA NS and the NF-SMS before and after NS incorporation were characterized by scanning electron microscopy (Philips XL30 FEG SEM). The PLGA NS and the NF-SMS were coated with gold using a sputter coater (DeskII, Denton vacuum Inc). During the process of gold coating, the gas pressure was 50 mtorr, and the current was 40 mA. The coating time was 120 seconds. Samples were analyzed at 15 kV.

Figure 25A:
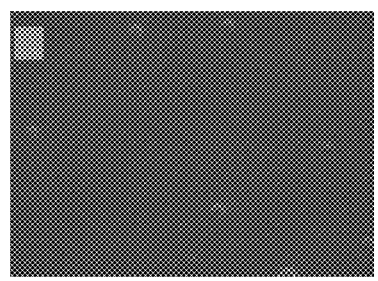
FIGS. 25A through 25E are SEM images of PLGA nanospheres having embedded therein polymer/NR4A1 polyplexes (25A), nanofibrous spongy microspheres (NF-SMS) (25B at 1000× magnification and 25C at 5000× magnification), and NF-SMS attaching the PLGA nanospheres having embedded therein polymer/NR4A1 polyplexes (25D at 2000× magnification and 25E at 5000× magnification)
Figure 25B:
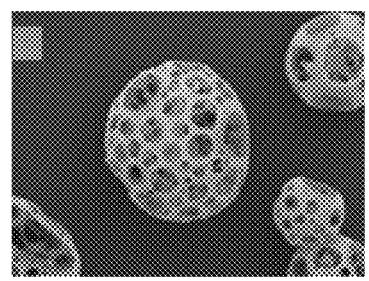
Figure 25C:
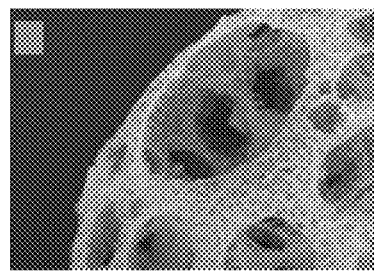
Figure 25D:
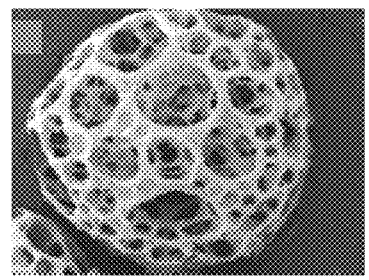
Figure 25E:
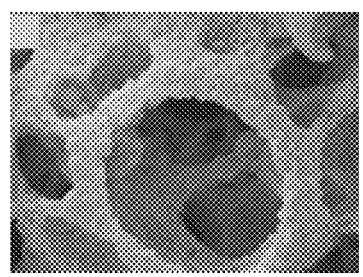

The SEM images of the PLGA NS and the NF-SMS before and after NS incorporation are shown in FIGS. 25A through 25E. FIG. 25A is the SEM of the PLGA NS containing the polymer/NR4A1 polyplex. FIGS. 25B and 25C are SEM images of the NF-SMS before PLGA NS incorporation, at 1000× and 5000× magnifications respectively. These images specifically illustrate the interconnected porous structure of the NF-SMS (FIG. 25B) and the nano-fibers (average diameter 100 nm) on the pore walls (FIG. 25C). FIGS. 25D and 25E are SEM images of the NF-SMS after PLGA NS incorporation, at 2000× and 5000× magnifications respectively.

The SEM images showed that the interpore openings and pore interconnectivity in the NF-SMS, which are advantageous for cell migration and mass transfer, and the nanofibrous morphology, which is advantageous for tissue regeneration, were retained after the PLGA NS immobilization procedure. Furthermore, these images confirmed that the PLGA NS were well distributed throughout the NF-SMS.

In Vitro Transfection Efficiency into Nucleus Pulposus (NP) Cells

Figures 26A, 26B, 26C:
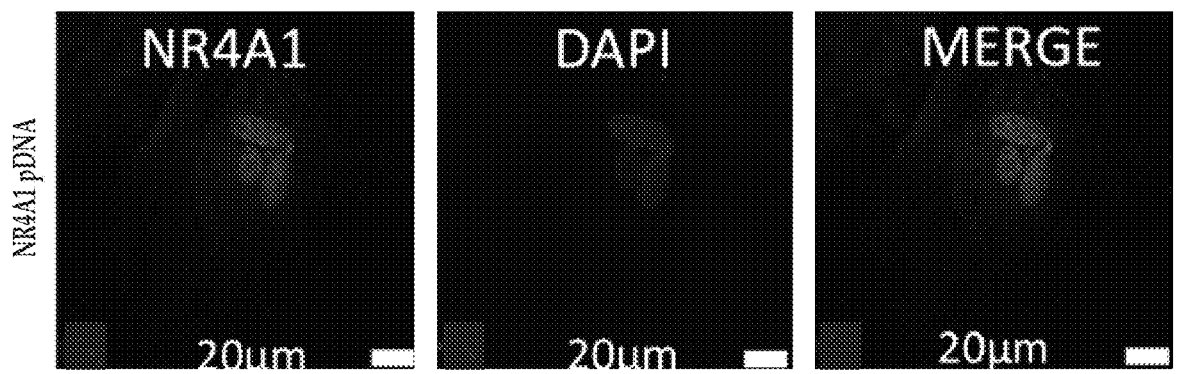
FIGS. 26A through 26F illustrate black and white confocal laser scanning microscopy images of nucleus pulposus (NP) cells transfected with polymer/NR4A1 polyplexes at 48 hours post-transfection (FIGS. 26A-26C), NP cells transfected with blank vectors of the hyperbranched polymer (FIGS. 26D-26F), where NR4A1 (originally green) and nuclei (originally blue) were stained by a fluorescein isothiocyanate (FITC)-labeled antibody and 4',6-diamidino-2-phenylindole (DAPI), respectively.
Figures 26D, 26E, 26F:
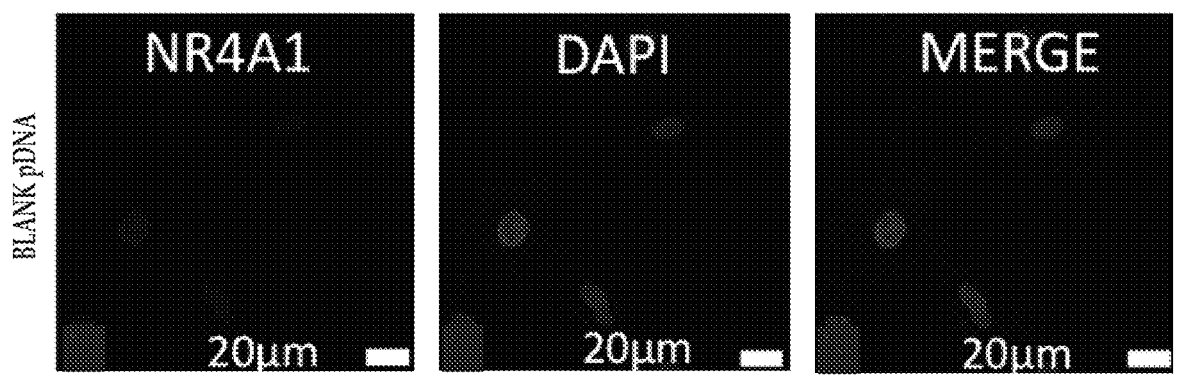
Figure 26G:
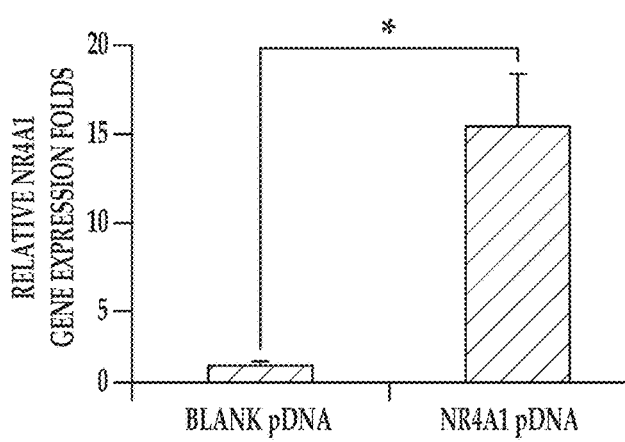
FIG. 26G is a graph depicting the real-time PCR of NR4A1 expression in the NP cells after transfection (error bars represent standard error of the mean, *P<0.05)
Figure 26H:
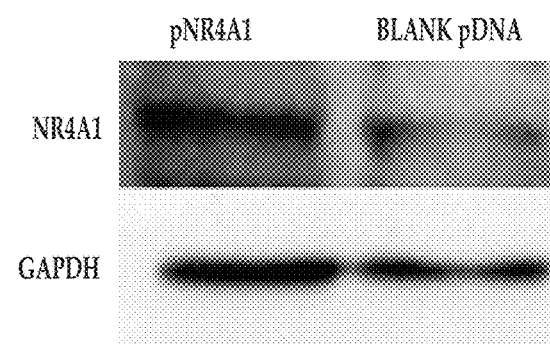
FIG. 26H is a graph depicting the western blot assay of NR4A1 expression in the NP cells after transfection.

To examine the transfection efficiency of the HP of this example for the NR4A1 gene, NP cells were transfected with polymer/NR4A1 polyplexes with an N/P ratio of 8. HP loading of a blank plasmid DNA without NR4A1 expression was used as a negative control. At 48 hours after transfection, a significantly stronger fluorescent staining for NR4A1 was found in the cells transfected with polymer/NR4A1 polyplexes as compared to that in the negative control (see FIGS. 26A-26F). Consistently, NP cells transfected with polymer/NR4A1 polyplexes expressed a significantly higher level of NR4A1 mRNA than control cells as detected by real time PCR (FIG. 26G). In parallel, these NP cells also expressed a significantly higher level of NR4A1 protein than control cells as detected by western blotting (FIG. 26H).

Antifibrotic Effect of NR4A1 in NP Cells

Figure 27:
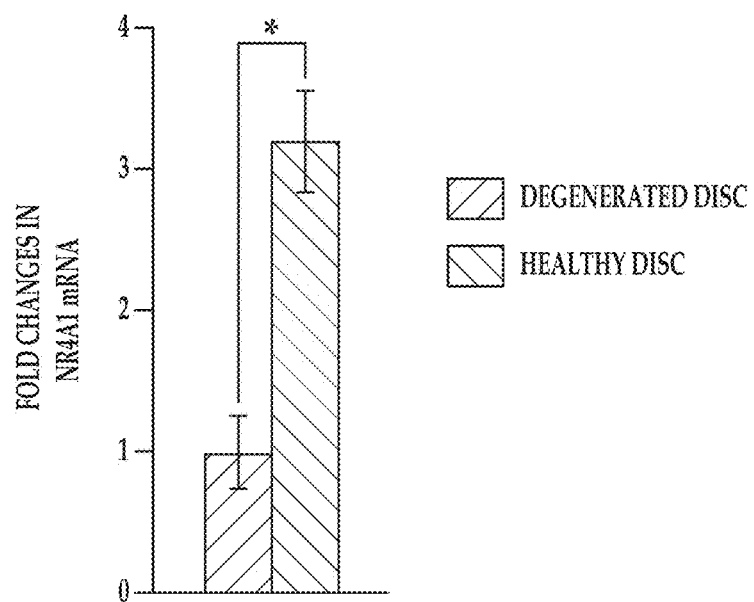
FIG. 27 is a graph depicting the fold changes in NR4A1 mRNA expression in healthy NP tissue and degenerated NP tissue.

Antibodies were used to stain NR4A1 protein and the fibrosis marker, α-smooth muscle actin (α-SMA, encoded by the gene ACTA2) in healthy and degenerated human NP tissue. While the staining results are not shown, it was found that the NR4A1 protein was highly expressed in healthy NP tissue, but was weakly expressed in degenerated NP tissue. Consistently, NR4A1 mRNA levels were found to be significantly higher in healthy NP tissue than in degenerated NP tissue, as shown in the graph of FIG. 27.

Figure 28A:
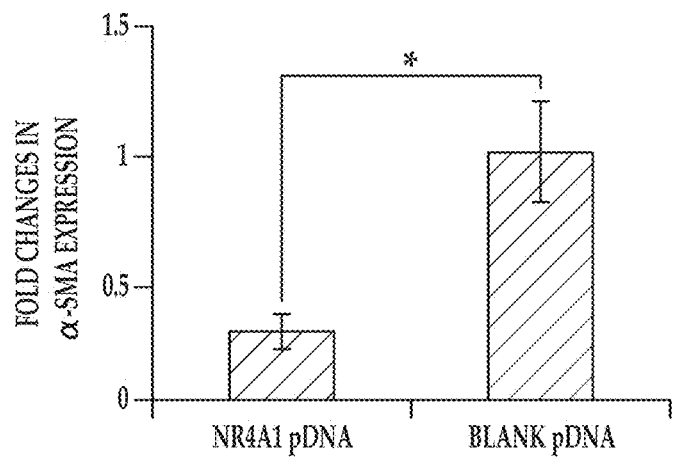
FIGS. 28A and 28B are graphs depicting the fold changes in α-smooth muscle actin expression and stress fiber formation, respectively, in human NP cells incubated with TGF-β1 (10 ng·ml$^{-1}$) and either polymer/NR4A1 polyplexes or blank vectors of the hyperbranched polymer.
Figure 28B:
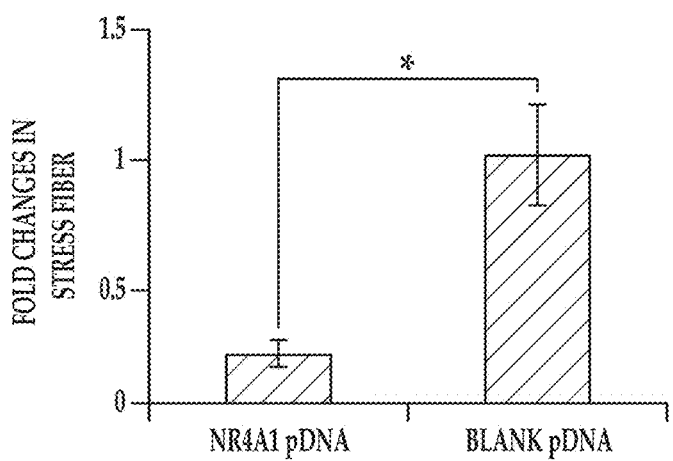

To verify that overexpression of NR4A1 could result in protective effects against a fibrotic response induced by the TGF-β signaling pathway, α-SMA expression and stress fiber formation were examined in human NP cells incubated with TGF-β1 (10 ng-ml$^{-1}$) and either polymer/NR4A1 polyplexes or blank vectors of the hyperbranched polymer. While the immunofluorescence staining results are not shown, it was found that the immunofluorescence staining for α-SMA and stress fibers was decreased dramatically in the polymer/NR4A1 polyplex transfected group (HP loaded with NR4A1 pDNA) compared to the blank pDNA group (HP loaded with blank plasmid DNA). The effect on α-SMA expression is shown in the graph in FIG. 28A and the effect on stress fiber formation is shown in the graph in FIG. 28B. These results indicated that the fibrotic effects of TGF-β were reduced by NR4A1 overexpression.

In Vivo Gene Therapy Efficacy

Needle puncture in rat tails was used to induce disc degeneration (disc fibrosis) in the caudal spines. One group was left untreated (referred to as the degeneration model group), another group was treated with the NS-incorporated NF-SMS (i.e., HP-NR4A1/NF-SMS), and still another group was treated with NF-SMS incorporated with blank vectors of the hyperbranched polymer (i.e., HP-blank/NF-SMS). The normal control group was not punctured or treated. More specifically, 4 weeks after the initial needle puncture, the treated groups had the NS-incorporated NF-SMS or the blank vector-incorporated NF-SMS injected into the rat tail near the original needle puncture. After injection, the holes were filled with granular gelatin foam to prevent extravasation of injected suspension.

Figure 29A:
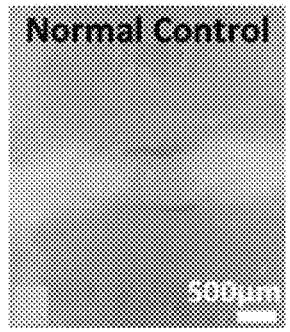
FIGS. 29A through 29D are representative gross appearances of (29A) a normal control rat caudal spine, (29B) a rat caudal spine punctured and not treated (degeneration model group), (29C) a rat caudal spine punctured and treated with NF-SMS attaching blank vectors of a hyperbranched polymer, and (29D) a rat caudal spine punctured and treated with NF-SMS attaching PLGA nanospheres having embedded therein polymer/NR4A1 polyplexes.
Figure 29B:
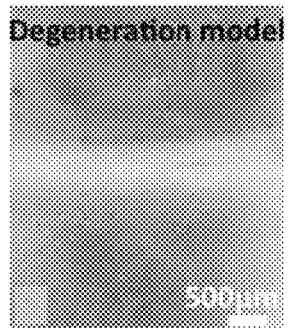
Figure 29C:
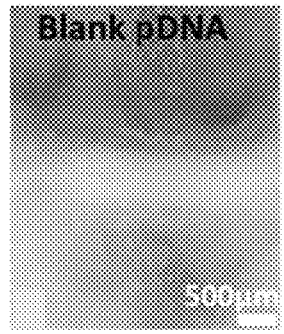
Figure 29D:
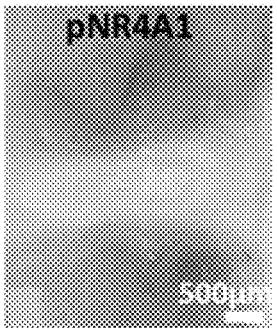
Figure 29E:
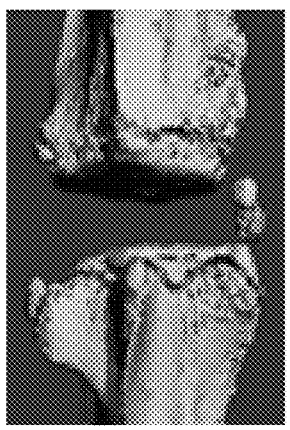
FIGS. 29E through 29H are micro computed tomography (PCT) images of (29E) the normal control rat caudal spine, (29F) the rat caudal spine punctured and not treated (degeneration model group), (29G) the rat caudal spine punctured and treated with NF-SMS attaching blank vectors of a hyperbranched polymer, and (29H) the rat caudal spine punctured and treated with NF-SMS attaching PLGA nanospheres having embedded therein polymer/NR4A1 polyplexes.
Figure 29F:
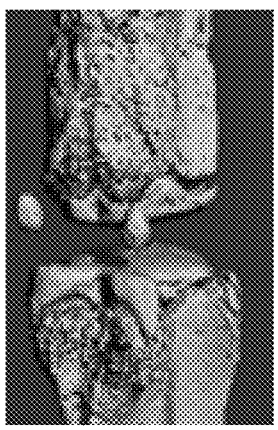
Figure 29G:
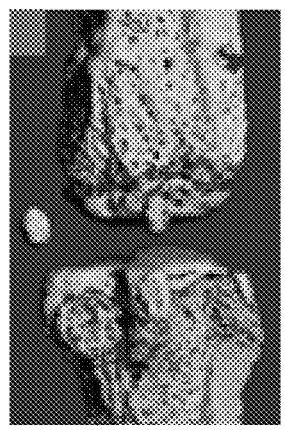
Figure 29H:
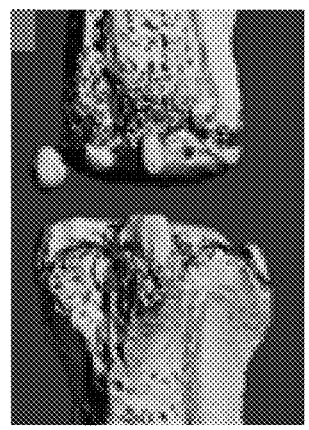

After treatment for 4 weeks or no treatment for 8 weeks, samples from the various groups were first evaluated in terms of gross appearance and using μCT imaging. These results are shown in FIGS. 29A-29H. As shown in FIGS. 29B and 29F, in the degeneration model group, the NP nearly completely disappeared and the most severe fibrosis occurred at the center area of the NP tissue. μCT images indicated characteristics of disc regeneration in the NS-incorporated NF-SMS treatment group (FIG. 29H) with a greater disc height as compared to the degeneration model group (FIG. 29F) and to the blank vector-incorporated NF-SMS group (FIG. 29G). Notably, the NS-incorporated NF-SMS group also showed a greater area of translucent disc matrix and less fibrous tissue in gross appearance (FIG. 29D). Based on the gross appearance and μCT imaging data, the discs in the blank vector-incorporated NF-SMS group were similar to the degeneration model group with narrow disc space and fibrous tissue invasion (comparing FIGS. 29C and 29G with FIGS. 29B and 29F).

The therapeutic efficacy was further evaluated using histological analysis at 4 weeks after injection of the NS-incorporated NF-SMS (see FIGS. 30A-30L). In the intact discs of the normal control group, the oval-shaped NP occupied a large volume of the disc space in the midsagittal cross-section as confirmed by HE staining (FIGS. 30A and 30E). The NP area was stained strongly by Safranin-O, indicating a high glycosaminoglycan (GAG) content (FIG. 30I). In the degeneration model group, the disc space collapsed, with evident fibrous tissue invasion (FIGS. 30B, 30F, and 30J). Although discs in the NS-incorporated NF-SMS (HP-NR4A1/NF-SMS) group still displayed a certain degree of degeneration features (FIGS. 30D, 30H, and 30L), there was clear therapeutic efficacy as compared to the degeneration model group (FIGS. 30B, 30F, and 30J) or the blank vector-incorporated NF-SMS (HP-blank/NF-SMS) group (FIGS. 30C, 30G, and 30K). The NP area in the NS-incorporated NF-SMS group was similar to the normal control and stained positively with Safranin-O (FIG. 30L). In the blank vector-incorporated NF-SMS group, inhomogeneous fibrous tissue was found, and the NP area was stained negatively for Safranin-O (FIGS. 30C, 30G, and 30K).

Masson's Trichrome staining for collagen in extracellular matrix and immunohistochemical staining for collagen type I and α-SMA were used to evaluate the fibrous tissue formation in vivo (FIGS. 31A-31P). In the intact discs of the normal control group, the NP area was stained negative for Masson's Trichrome (collagen), type I collagen, and α-SMA (FIGS. 31A, 31E, 31I, and 31M). In the degeneration model group, the NP area was stained positive for Masson Trichrome, type I collagen and α-SMA (FIGS. 31B, 31F, 31J, and 31N). The NP area was also stained positive for Masson Trichrome, collagen type I, and α-SMA in the blank vector-incorporated NF-SMS (HP-blank/NF-SMS) group (FIGS. 31C, 31G, 31K, and 31O). These fibrous tissue stains were weak in the NS-incorporated NF-SMS (HP-NR4A1/NF-SMS) group (FIGS. 3. 31D, 31H, 31L, and 31P).

The data in this example supports the conclusion that the injectable two-stage NR4A1 plasmid DNA (pDNA) delivery nanofibrous spongy microspheres (NF-SMS) reverse fibrotic degeneration and facilitate intervertebral disc regeneration.

Example 6

Preparation of Support Structures

Star-shaped poly(L-lactic acid)-co-polyHEMA (SS-PLLA-co-polyHEMA) was synthesized and assembled into nanofibrous spongy microspheres (NF-SMS) using emulsification and phase separation techniques. More specifically, the polymer (0.4 g) was dissolved in THF at 50° C. with a concentration of 2% w/v. Under rigorous mechanical stirring (Speed 9, Fisher Science Inc.), glycerol (50° C.) with three times the volume of star-shaped PLLA solution was gradually added into the polymer solution. After stirring for five minutes, the mixture was quickly poured into liquid nitrogen. After 10 minutes, a water-ice mixture (1 L) was added for solvent exchange for 24 hours. The microspheres were sieved and washed with distilled water eight times to remove residual glycerol on the sphere surfaces. The spheres were then lyophilized for three days.

Figure 32A:
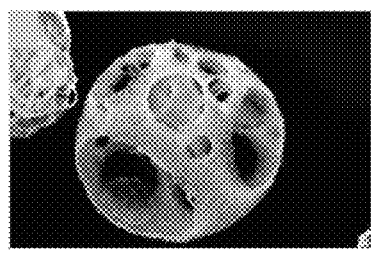
FIGS. 32A through 32F are SEM images of nanofibrous spongy microspheres before (FIG. 32A) and after (FIG. 32D) cell seeding for 24 hours; of nanofibrous microspheres before (FIG. 32B) and after (FIG. 32E) cell seeding for 24 hours; and solid microspheres before (FIG. 32C) and after (FIG. 32F) cell seeding for 24 hours (the diameter of spheres ranges from 30 to 60 m; scale bar: 32A-32C=20 µm and 32D-32F=10 µm)
Figure 32B:
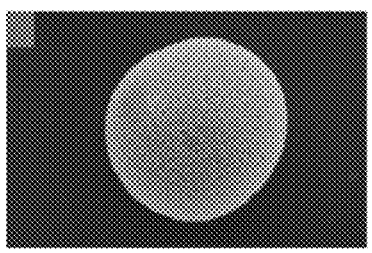
Figure 32C:
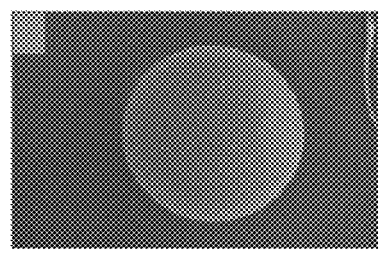

At the micro-scale, NF-SMS had an inter-connected pore structure throughout the entire microsphere (FIG. 32A). The pores in the NF-SMS had an average diameter of approximately 15 μm, which were highly interconnected (the inter-pore openings between the pores were about 10 μm in size). At the nano-scale, NF-SMS were composed entirely of ECM-mimicking nanofibers. Due to the co-presentation of biomimetic nanofibers and a highly porous structure, NF-SMS were hypothesized to simultaneously promote MSCs seeding and attachment. Nanofibrous microspheres without a porous structure (FIG. 32B) and conventional smooth microspheres (FIG. 32C) without the NF structure were used as controls to test this hypothesis.

Figure 32D:
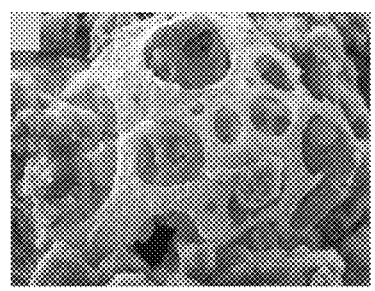
Figure 32E:
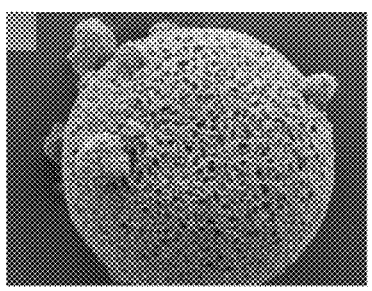
Figure 32F:
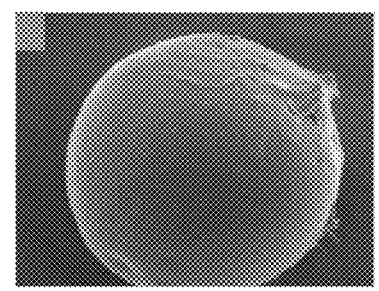

After 24 hours of cell seeding, rabbit mesenchymal stem cells (MSCs) attached to both the outer surfaces and the interior pores of the NF-SMS with a more spherical 3D morphology (FIG. 32D). The MSCs could only attach to the outer surfaces of the nanofibrous microspheres, also with a more spherical morphology (FIG. 32E). On the smooth microspheres, there seemed fewer but spread cells on the surfaces (FIG. 32F).

Preparation of Polymer/Anti-miR-199a Polyplexes

Hyperbranched polymers (HP) were formed in the same manner as described in Example 1. In this example, polyethyleneimine (PEI, Mw 800 Da), polyethylene glycol methyl ether (PEG, Mw 2000 Da), and hyperbranched bis-MPA polyester (H40: 64 hydroxyl) were used.

Designed H40 polymer solutions (1.0 mg/mL) were added slowly to RNA solutions containing 60 pmol of anti-miR-199a. The amount of polymer added was calculated on the basis of chosen N/P ratios of polymer/RNA (N nitrogen atoms of the polymer over P phosphates of RNA). The mixture was incubated at room temperature for 30 minutes for the polyplex formation.

The anti-miR-199a first complexed with the PEI on the outer shell of the hyperbranched polyester cores. The HP molecular cores and PEI/anti-miR-199a shells together assembled into the hydrophobic spherical shell sandwiched between the inner PEG core and the outer PEG chains of the 3-layer nanospheres.

Preparation of PLGA Nanospheres (NS) Containing Polymer/Anti-miR-199a Polyplexes PLGA (poly(lactide-co-glycolide), average molecular weight of 64,000 nanospheres (NS) containing the polymer/anti-miR-199a polyplex were fabricated using a modified water-in-oil-in-water (w/o/w) double emulsion method. Briefly, 30 mg of PLGA was dissolved in 1 mL of dichloromethane. 100 μL aqueous solution of polymer/anti-miR-199a polyplex with an N/P of 10 was added into the above solution and emulsified with a probe sonicator at 50 W (Virsonic 100, Gardiner, N.Y.). This primary w/o emulsion was then emulsified into 10 mL of PVA solution (1% wt/vol) under sonication at 90 W to form the w/o/w emulsion. The resulting secondary emulsion was magnetically stirred at room temperature for about 12 hours to evaporate the solvents. The PLGA (anti-miR-199a) NS (average diameter of 300 nm) were collected by centrifugation and washed three times with water and freeze dried.

Formation of Cell/PLGA (Anti-miR-199a) NS/NF-SMS Constructs

The PLGA (anti-miR-199a) NS (including the polymer/anti-miR-199a polyplexes embedded therein) were mixed with the NF-SMS having the rabbit mesenchymal stem cells (MSCs) attached thereto (as shown in FIG. 32D).

As a control for some of the tests, blank vectors of the hyperbranched polymer were mixed with the NF-SMS having the rabbit mesenchymal stem cells (MSCs) attached thereto (as shown in FIG. 32D). These constructs are referred to throughout this example as cell/blank HP/NF-SMS constructs.

Subcutaneous Implantation of Cell/PLGA (Anti-miR-199a) NS/NF-SMS Constructs

To investigate the long-term stability of engineered nucleus pulposus-like phenotype, the cell/PLGA (anti-miR-199a) NS/NF-SMS constructs were cultured in vitro with TGF-□1 for 3 weeks, and then were implanted into nude mice subcutaneously. The cell/PLGA (anti-miR-199a) NS/NF-SMS constructs without TGF-□1 induction were used as a first control, and the cell/blank HP/NF-SMS constructs with TGF-□1 induction were used as a second control.

Figure 33A:
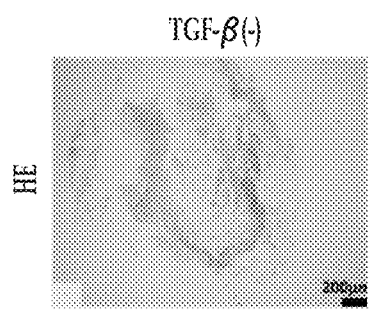
FIGS. 33A through 33I are H&E stained images (FIGS. 33A-33C), Safranin-O stained images (FIGS. 33D-33F), and VonKonssa stained images (FIGS. 33G-33I) of a first control group (FIGS. 33A, 33D, and 33G), a second control group (FIGS. 3313, 33E, and 33H), and cell/PLGA NS/NF-SMS constructs (FIGS. 33C, 33F, and 33I) after subcutaneous implantation for 8 weeks (scale bar: 50 µm)
Figure 33B:
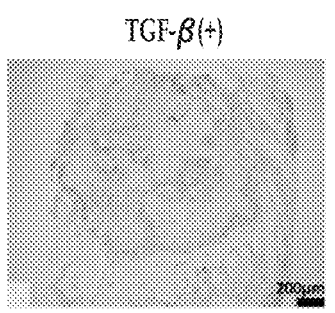
Figure 33C:
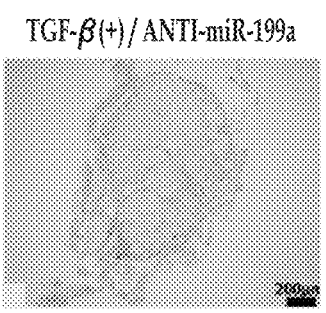
Figure 33D:
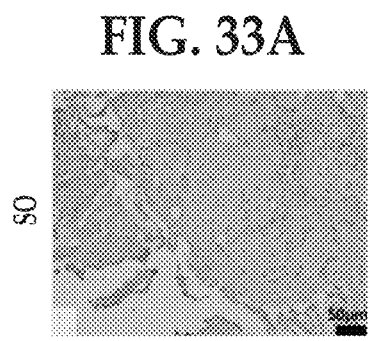
Figure 33E:
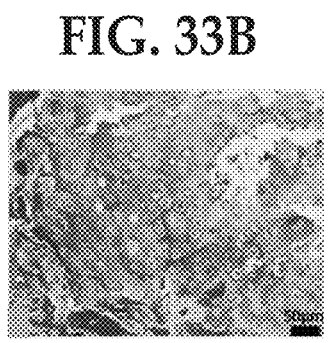

Eight weeks after the implantation, the various constructs were collected to examine the effect of anti-miR-199a on maintaining the nucleus pulposus-like phenotype in vivo. The various constructs were stained with H&E, Safranin-O, and Von Kossa. The results for the first control are shown in FIGS. 33A, 33D, and 33G. The results for the second control are shown in FIGS. 33B, 33E, and 33H. The results for the cell/PLGA (anti-miR-199a) NS/NF-SMS constructs are shown in FIGS. 33C, 33F, and 33I.

Figure 33F:
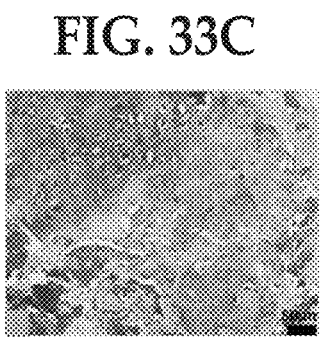
Figure 33G:
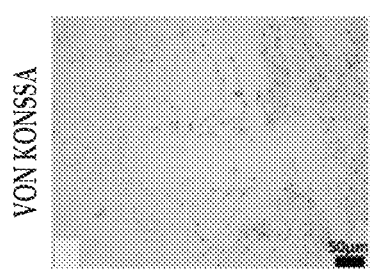
Figure 33H:
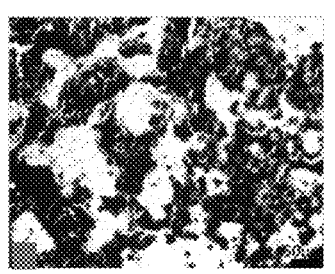
Figure 33I:
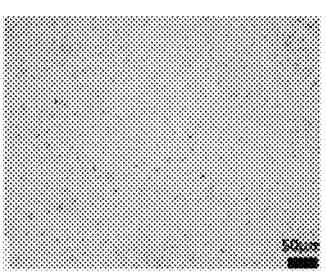

Strong positive staining for glycosaminoglycan (GAG) with Safranin-O was observed in the cell/PLGA (anti-miR-199a) NS/NF-SMS constructs with TGF-☐1 induction (FIG. 33F). These same constructs were stained negative for mineralization (by the Von Kossa method) (FIG. 33I). In contrast, implanted cell/blank HP/NF-SMS constructs with TGF-☐1 induction (second control) consisted of large areas of ossified tissue, and were stained positive for GAG and mineralization using Safranin-O (FIG. 33E) and the von Kossa method (FIG. 33H), respectively. Implanted cell/PLGA (anti-miR-199a) NS/NF-SMS constructs without TGF-☐1 induction (first control) were stained negative for GAG and mineralization using Safranin-O (FIG. 33D) and the von Kossa method (FIG. 33G). These results indicated that anti-miR-199a played an important role in maintaining the nucleus pulposus-like phenotype and preventing mineralization after subcutaneous implantation.

Degenerated Disc Model and miRNA (Anti-miR-199A) Delivery by Percutaneous Puncture After anesthesia, rabbits were placed in a lateral position on a fluoroscopy imaging table. Under C-arm image guidance, an 18-gauge spinal needle was inserted into the intervertebral disc (IVD) using a posterolateral approach at a point 1-2 cm lateral to the midline spinous process, and at an angle of 30-45 degrees to the spine. The needle was carefully advanced to the lateral margin of the IVD space without touching the vertebral body to avoid osteophyte formation. The needle was gently inserted into the disc space. Anteroposterior and lateral views from the C-arm projection were used to guide the placement of the needle into the center of the IVD. After verifying that the needle was in the IV), about 0.005 to 0.008 g nucleus pulposus was aspirated to induce disc degeneration model. Aspirated disc fragments were carefully examined under dissecting microscopy to confirm that only nucleus pulposus was aspirated.

4 weeks after the first surgery, the same approach was taken to insert a 25G needle into the same IVD on the opposite side. For one group, polyplexes (HP-anti-miR-199a) embedded in PLGA nanoparticles combined with NF-SMS and rabbit MSCs (i.e., the cell/PLGA (miRNA) NS/NF-SMS constructs) were injected to treat the needle puncture-induced lumbar disc degeneration. For another group, hyperbranched polymer embedded in PLGA nanoparticles combined with NF-SMS and rabbit MSCs (i.e., cell/blank HP/NF-SMS constructs) were injected. After these injections, the holes were filled with granular gelatin foam through the cannula to prevent extravasation of injection suspension. Fluoroscopy imaging was used to show that the needle was inserted into the IVD space via this percutaneous approach.

Still another group was left untreated (referred to as the sham group). The normal control group was not punctured or treated.

In Vivo Effect of Cell/PLGA (Anti-miR-199a) NS/NF-SMS Constructs Injection

Figures 34A, 34B, 34C, 34D:
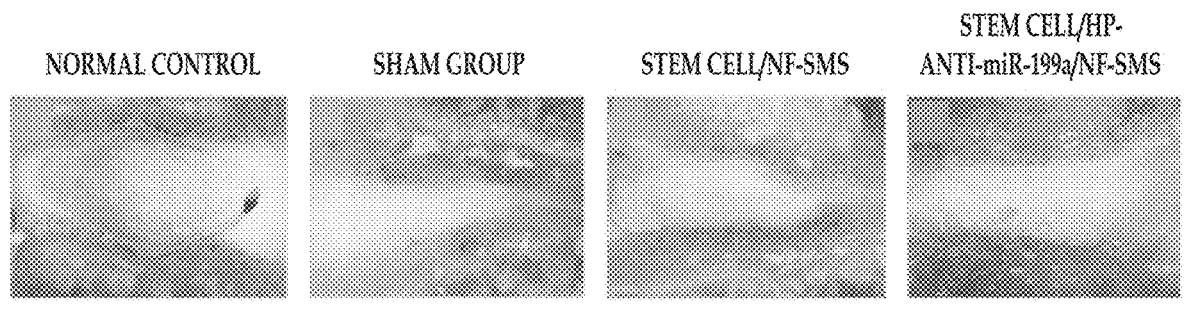
FIGS. 34A through 34D are representative gross appearances of (34A) a normal control rabbit lumbar spine, (34B) a rabbit lumbar spine punctured and not treated (sham group), (34C) a rabbit lumbar spine punctured and treated with NF-SMS and blank vectors of a hyperbranched polymer, and (34D) a rabbit lumbar spine punctured and treated with NF-SMS and PLGA nanospheres having embedded therein polymer/anti-miR199a polyplexes.
Figures 34E, 34F, 34G, 34H:
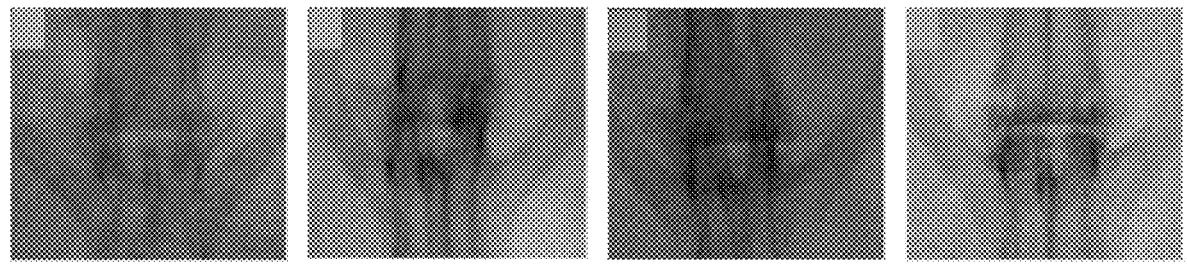
FIGS. 34E through 34H are micro computed tomography (pCT) images of (34E) the normal control rabbit lumbar spine, (34F) the rabbit lumbar spine punctured and not treated (sham group), (34G) the rabbit lumbar spine punctured and treated with NF-SMS and blank vectors of a hyperbranched polymer, and (34H) the rabbit lumbar spine punctured and treated with NF-SMS and PLGA nanospheres having embedded therein polymer/anti-miR199a polyplexes.

After treatment for 6 weeks, samples were collected from the normal control, the sham group, the group treated with cell/blank HP/NF-SMS constructs, and the group treated cell/PLGA (anti-miR-199a) NS/NF-SMS constructs. The gross appearance and fluoroscopy images were used to assess the therapeutic efficacy (see FIG. 34A-H). In the sham group (punctured without treatment), the NP nearly completely disappeared, but ectopic bone formation was found surrounding the IVD space (FIGS. 34B and 34F). Characteristics of disc regeneration were found in the cell/PLGA (anti-miR-199a) NS/NF-SMS constructs group with a greater disc height (FIG. 34H) as compared to the sham group (FIG. 34F). Notably, the cell/PLGA (anti-miR-199a) NS/NF-SMS constructs group showed more normal translucent disc matrix in gross appearance (FIG. 34D) and less ectopic bone formation in the fluoroscopy image (FIG. 34H). From the fluoroscopy images and gross appearance, the discs in the cell/blank HP/NF-SMS constructs group were similar to the cell/PLGA (anti-miR-199a) NS/NF-SMS constructs group. However, the disc space in the cell/blank HP/NF-SMS constructs group (FIG. 34G) was found to be narrower than that in the cell/PLGA (anti-miR-199a) NS/NF-SMS constructs group (FIG. 34H).

Figure 35:
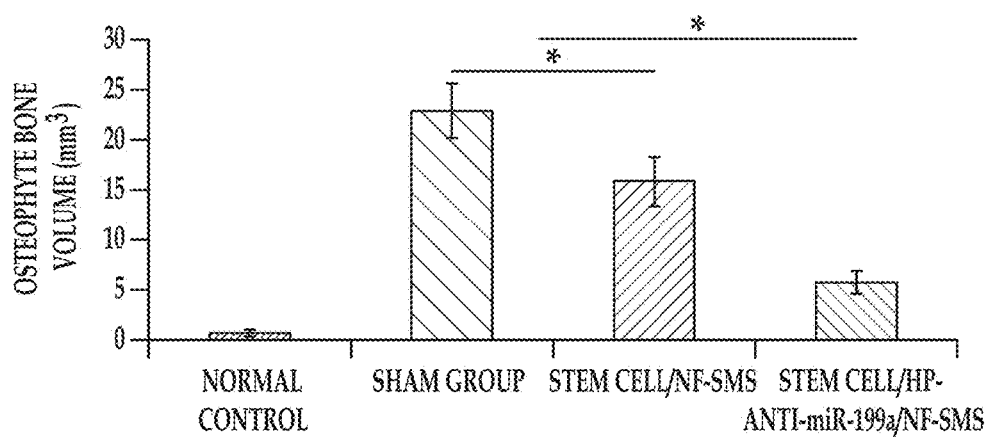
FIG. 35 is a graph depicting the osteophyte bone volume of the normal control rabbit lumbar spine, the rabbit lumbar spine punctured and not treated (sham group), the rabbit lumbar spine punctured and treated with NF-SMS and blank vectors of a hyperbranched polymer, and the rabbit lumbar spine punctured and treated with NF-SMS and PLGA nanospheres having embedded therein polymer/anti-miR199a polyplexes.

Three-dimensional (3D) reconstructions and cross-sections of μCT scans of the rabbit lumbar spines in the various groups were generated although the results are not shown. The osteophyte bone volume of each of the groups using the software of the μCT equipment, and the results are shown in FIG. 35. The results confirmed the complete absence of heterotopic ossification in the normal control group. The heterotopic ossification area in the cell/PLGA (anti-miR-199a) NS/NF-SMS constructs group was significantly smaller than those in the sham group and cell/blank HP/NF-SMS constructs group.

The therapeutic efficacy was evaluated using histological analysis at 6 weeks after injection of the constructs (see FIGS. 36A-36P). H&E and Safranin-O staining were performed on the various samples. In the intact disc (normal) control group (FIGS. 36A, 36E, 36I, and 36M), the oval-shaped NP occupied a large volume of the disc space in the midsagittal cross-section as revealed by HE staining (FIG. 36A). The NP area showed strong Safranin-O staining, indicating a high glycosaminoglycan (GAG) content (FIGS. 36E and 36I). In the sham group (FIGS. 36B, 36F, 36J, and 36N), the disc space collapsed, with evident fibrous tissue invasion. Although discs in the cell/PLGA (anti-miR-199a) NS/NF-SMS constructs group still displayed features of degeneration to a certain extent (FIGS. 36D, 36H, 36L, and 36P), the therapeutic efficacy was obvious as compared to the sham group (FIGS. 36B, 36F, 36J, and 36N). The NP area in the cell/PLGA (anti-miR-199a) NS/NF-SMS constructs group was similar to the normal control group, and stained positively with Safranin-O (FIGS. 36H and 36L). In the cell/blank HP/NF-SMS constructs group (FIGS. 36C, 36G, 36K, and 36O), the NP area was stained weaker by Safranin-0 as compared to the cell/PLGA (anti-miR-199a) NS/NF-SMS constructs group. The bony endplate (BEP) thickness and abnormal/endplate calcification were significantly higher in the sham group (FIG. 36N) and the cell/blank HP/NF-SMS constructs group (FIG. 36O) compared to the cell/PLGA (anti-miR-199a) NS/NF-SMS constructs group (FIG. 36P).

In conclusion, the sustained delivery of anti-miR-199A substantially suppressed the NP fibrosis and abnormal mineralization, and significantly reduced NP degeneration.

In Example 6, the PLGA NS (including the polymer/anti-miR-199a polyplexes embedded therein), cells and NF-SMS were mixed together. However, it is to be understood that the cells and the PLGA NS may be immobilized on the NF-SMS using a post seeding method. As an example, the rabbit MSCs and the PLGA (anti-miR-199a) NS may be dispersed in hexane and seeded onto NF-SMS dropwise. Then, the NF-SMS may be subject to vapor of a mixed solvent of hexane/THF (9:1 by volume) for 30 minutes. The NF-SMS may be dried under vacuum for 3 days to remove the solvents. As a result of this type of method, the cells and PLGA NS become immobilized on the NF-SMS.

In the examples disclosed herein, linear polyester based copolymers and hyperbranched polyester based copolymers have been developed. The hyperbranched copolymers exhibit a very high miRNA or pDNA binding affinity and a very low toxicity. The hyperbranched dendritic polyester core provides hydrophobicity and contributes to the copolymer's high molecular weight. In the copolymer, the low molecular weight PEI (low toxicity) is grafted on the surface of the dendritic hyperbranched polyester core to distribute its positive charge. The low molecular weight PEI is also sheathed by grafted long PEG chains.

As illustrated throughout the examples, the HP/miRNA polyplexes self-assembled into 3-layer nanoparticles, where the HP/miRNA polyplexes form a nano-sized spherical shell sandwiched between the inner PEG core/section and the outer PEG layer/section. The double shell-like charge distribution was found to be very stable even under rigorous sonication, negligible in cytotoxicity, and highly efficient in transfecting cells.

In addition, the examples herein demonstrate that these polyplexes can be stably encapsulated into biodegradable PLGA microspheres and can be controllably released for a long duration. Even when encapsulated, the polyplexes retain the particular nanostructure and retain their biological activity. The polyplex-embedded microspheres can also be attached onto PLLA nanofibrous scaffolds (or other support structures), where the released HP/miRNA polyplexes can locally activate endogenous cells to completely regenerate a critical-sized bone defect without any externally introduced cells.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 30% to about 70% should be interpreted to include not only the explicitly recited limits of about 30% to about 70%, but also to include individual values, such as 32%, 44.5%, 68%, etc., and sub-ranges, such as from about 35% to about 65%, from about 40% to about 60%, etc. Furthermore, when "about" is utilized to describe a value, this is meant to encompass minor variations (up to +/−10%) from the stated value.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:

1. A hyperbranched polyplex, comprising:
    a plurality of self-assembled hyperbranched polymers, each hyperbranched polymer including:
        a hyperbranched, hydrophobic molecular core;
        respective low molecular weight polyethyleneimine chains attached to two or more branches of the hyperbranched, hydrophobic molecular core; and
        respective polyethylene glycol chains attached to two or more other branches of the hyperbranched, hydrophobic molecular core;
    wherein the hyperbranched polyplex is a 3-layer nanosphere or nanoparticle in which:
        a first plurality of the polyethylene glycol chains forms a hydrophilic inner section of the polyplex;
        a second plurality of the polyethylene glycol chains forms a hydrophilic outer section of the polyplex;
        the hyperbranched, hydrophobic molecular cores and the low molecular weight polyethyleneimine chains form a central section positioned between the hydrophilic inner and outer sections; and
        the central section further includes DNA or RNA biomolecules complexed with the low molecular weight polyethyleneimine chains.

2. The hyperbranched polyplex as defined in claim 1 wherein the RNA biomolecules are complexed with the low molecular weight polyethyleneimine chains, and wherein the RNA biomolecules are selected from the group consisting of miRNA, mRNA, and siRNA.

3. The hyperbranched polyplex as defined in claim 1 wherein each of the hyperbranched, hydrophobic molecular cores is a hyperbranched polyester including at least 4 terminal hydroxyl groups.

4. The hyperbranched polyplex as defined in claim 1 wherein the low molecular weight polyethyleneimine chains each have a molecular weight ranging from about 400 g/mol to about 5,000 g/mol.

5. The hyperbranched polyplex as defined in claim 1 wherein the DNA biomolecules are complexed with the low molecular weight polyethyleneimine chains, and wherein the DNA biomolecules are selected from the group consisting of pDNA, cDNA, cpDNA, gDNA, msDNA, mtDNA, and rDNA.

6. A biodegradable sphere, comprising;
    a biodegradable polymer matrix; and
    a plurality of the hyperbranched polyplexes of claim 1 embedded in the biodegradable polymer matrix.

7. A biodegradable or erodible structure, comprising:
    a scaffold or hydrogel; and
    a plurality of the biodegradable spheres of claim 6 attached to the scaffold or hydrogel.

8. The biodegradable or erodible structure as defined in claim 7 wherein the scaffold is formed of a porous material including a plurality of nano-fibers aggregated together and pores defined between at least some of the plurality of nano-fibers.

9. A method for making the hyperbranched polyplex of claim 1, the method comprising:
    forming the hyperbranched polymer by:
        converting hydroxyl groups of a hyperbranched polyester to carboxyl groups, thereby forming a first modified hyperbranched polyester;
        introducing polyethylene glycol chains and azido groups onto the first modified hyperbranched polyester to form a second modified hyperbranched polyester; and
        covalently attaching respective low molecular weight polyethyleneimine chains to two or more branches of the second modified hyperbranched polyester;

forming a solution of the hyperbranched polymer;

mixing the solution of the hyperbranched polymer with any of a DNA solution or an RNA solution to form a mixture; and incubating the mixture, thereby forming the hyperbranched polyplex which is a 3-layer nanosphere or nanoparticle.

10. The hyperbranched polyplex as defined in claim 1, wherein a respective triazole attaches each of the respective low molecular weight polyethyleneimine chains to each of the two or more branches.

11. The hyperbranched polyplex as defined in claim 2, wherein:

the RNA biomolecules are miRNA; and the hyperbranched polymer of the plurality of self-assembled hyperbranched polymers and the miRNA are present at an N/P ratio, wherein the N/P ratio is 10, and wherein N/P in the N/P ratio is N nitrogen atoms of the hyperbranched polymer per P phosphates of miRNA.

* * * * *